US008278422B2

(12) United States Patent
Paszty

(10) Patent No.: US 8,278,422 B2
(45) Date of Patent: Oct. 2, 2012

(54) ANTIBODIES THAT SPECIFICALLY BIND BETA-LIKE GLYCOPROTEIN HORMONE POLYPEPTIDES AND HETERODIMERS THEREOF

(76) Inventor: Christopher J. R. Paszty, Ventura, CA (US)

(*) Notice: Subject to any disclaimer, the term of this patent is extended or adjusted under 35 U.S.C. 154(b) by 3 days.

(21) Appl. No.: 12/816,475

(22) Filed: Jun. 16, 2010

(65) Prior Publication Data

US 2010/0255537 A1 Oct. 7, 2010

Related U.S. Application Data

(60) Division of application No. 12/072,822, filed on Feb. 27, 2008, now Pat. No. 7,883,868, which is a continuation of application No. 09/818,954, filed on Mar. 27, 2001, now Pat. No. 7,514,239, which is a continuation-in-part of application No. 09/723,970, filed on Nov. 27, 2000, now abandoned.

(60) Provisional application No. 60/199,211, filed on Apr. 24, 2000, provisional application No. 60/192,654, filed on Mar. 28, 2000.

(51) Int. Cl.
*C07K 16/26* (2006.01)
*C07K 14/59* (2006.01)
(52) U.S. Cl. ............... 530/387.1; 530/387.3; 530/387.9; 530/388.15; 530/350; 435/326; 435/328; 435/331; 435/336
(58) Field of Classification Search ........................ None
See application file for complete search history.

(56) References Cited

U.S. PATENT DOCUMENTS

| 5,116,964 | A | 5/1992 | Capon et al. |
| 5,194,596 | A | 3/1993 | Tischer et al. |
| 5,705,478 | A | 1/1998 | Boime |
| 5,712,122 | A | 1/1998 | Boime et al. |
| 5,770,577 | A | 6/1998 | Kinstler et al. |
| 6,552,170 | B1 | 4/2003 | Thompson et al. |
| 6,673,344 | B1 | 1/2004 | Li et al. |
| 7,358,341 | B2 | 4/2008 | Paszty et al. |
| 7,514,239 | B2 | 4/2009 | Paszty et al. |
| 2002/0068279 | A1* | 6/2002 | Burgess et al. .................. 435/6 |
| 2003/0059877 | A1 | 3/2003 | Mosselman et al. |
| 2003/0207403 | A1 | 11/2003 | Paszty et al. |
| 2008/0166768 | A1 | 7/2008 | Paszty et al. |
| 2008/0188417 | A1 | 8/2008 | Paszty et al. |

FOREIGN PATENT DOCUMENTS

| CA | 2394420 A1 | 6/2002 |
| EP | 1239039 A | 9/2002 |
| JP | 01/44475 | 6/2001 |
| WO | 94/01548 A2 | 1/1994 |
| WO | WO94/01548 * | 1/1994 |
| WO | 99/41377 A1 | 8/1999 |
| WO | 00/78964 A1 | 12/2000 |
| WO | 01/40291 A2 | 6/2001 |
| WO | 01/53346 A1 | 7/2001 |
| WO | 01/60850 A1 | 8/2001 |

OTHER PUBLICATIONS

Mahairas et al., Database EMBL Online:, accession No. AQ495547, (1999).*
Page 2 of U.S. Appl. No. 60/175,740, filed Jan. 12, 2000.*
Thotakura et al., "Glycoprotein hormones: glycobiology of gonadotropins," Glycobiology, vol. 5(1), pp. 3-10 (1995).
Wondisford, et al., "Thyroid-stimulating hormone in health and disease," Endocrinology, vol. 1, Third Edition (edited by L. DeGroot, et al.), pp. 208-217, published by W.B. Saunders Company, Philadelphia, PA (1995).
Moyle, et al., "Gonadotropins," Endocrinology, vol. 1, Third Edition (edited by L. DeGroot et al.), pp. 230-241, published by W.B. Saunders Company, Philadelphia, PA (1995).
Bo, et al., "Identification of the transcriptionally active genes of the chorionic gonadotropin beta gene cluster in vivo," J. Bio. Chem. vol. 267(5), pp. 3179-3184 (1992).
Begeot, et al., "Induction of pituitary lactotrope differentiation by luteinizing hormone alpha subunit," Science, vol. 226, pp. 566-568 (1984).
Moy et al., "Glycoprotein hormone alpha-subunit functions synergistically with progesterone to stimulate differentiation of cultured human endometrial stromal cells to decidualized cells: a novel role for free alpha-subunit in reproduction," Endocrinology, vol. 137(4), pp. 1332-1339 (1996).
Blithe, et al., "Free alpha molecules from pregnancy stimulate secretion of prolactin from human decidual cells: a novel function for free alpha in pregnancy," Endocrinology, vol. 129(4), pp. 2257-2259 (1991).
Hall, et al., Gonadotropins and the gonad: normal physiology and their disturbances in clinical endocrine diseases, Endocrinology, vol. 1, Third Edition (edited by L. DeGroot et al.), pp, 242-258, published by W.B. Saunders Company, Philadelphia, PA (1995).
AHFS Drug Information, "Thyroid Function," Edited by McEvoy, et al., pp. 2041-2042, American Society of Health-System Pharmacists, Inc., Bethesda, MD (1998).
AHFS Drug Information, "Gonadotropin, Chorionic," Edited by McEvoy, et al., pp. 2564-2567, American Society of Health-System Pharmacists, Inc., Bethesda, MD (1998).
Lapthorn, et al., "Crystal structure of human chorionic gonadotropin," Nature, vol. 369, pp. 455-461 (1994).
Isaacs, "Cystine knots," Current Opinion in Structural Biology, vol. 5, pp. 391-395 (1995).
Van Bael, et al., "Evidence for a trophic action of the glycoprotein hormone alpha-subunit in rat pituitary," J. Neuroendocrinology, vol. 8, pp. 99-102 (1996).

(Continued)

Primary Examiner — Bridget E Bunner
Assistant Examiner — Christina Borgeest
(74) Attorney, Agent, or Firm — John A. Lamerdin

(57) ABSTRACT

Novel β10 polypeptides and heterodimers thereof, and nucleic acid molecules encoding the same are disclosed. The invention also provides vectors, host cells, selective binding agents, and methods for producing β10 polypeptides and heterodimeric forms thereof, specifically α2/β10. Also provided for are methods for the treatment, diagnosis, amelioration, or prevention of diseases with β10 polypeptides and α2/β10 heterodimers or their respective binding agents.

8 Claims, 7 Drawing Sheets

OTHER PUBLICATIONS

Sun & Davies, "The Cysteine-knot growth factor superfamily," Annu. Rev. Biophys. Biomol. Struct. vol. 24, pp. 269-291 (1995).

Database EMBL Online: CNS0000U, accession No. AL049871 (1999).

Database EMBL Online: CNS01DRS, accession No. AL118555 (1999).

Database EMBL Online: accession No. AQ495547 (1999).

Nakabayashi, et al., "Thyrostimulin, a heterodimer of two new human glycoprotein hormone subunits, activates the thyroid-stimulating hormone receptor," J. Clinical Invest. vol. 109(11), pp. 1445-1452 (2002).

L.E. Benjamin, et al., "A plasticity window for blood vessel remodeling is defined by pericyte coverage of the preformed endothelial network and is regulated by PDGF-B and VEGF," Development, vol. 125, pp. 1591-1598 (1998).

S. Vukicevic et al., "Induction of nephrogenic mesenchyme by osteogenic protein 1 (bone morphogenic protein 7)," PNAS vol. 93, pp. 9021-9026 (1996).

J. Massague, "The TGF-Beta family of growth and differentiation factors," Cell, vol. 49, pp. 437-438 (1987).

T.F. Smith et al., "The challenges of genome sequence annotation or "the devil is in the details"", Nature Biotechnology, vol. 15, pp. 1222-1223 (1997).

J. Skolnick et al., "From genes to protein structure and function: novel applications of computational approaches in the genomic era," Trends in Biotech., vol. 18(1), pp. 34-39 (2000).

NCBI Locus AQ495547, Mahairas et al., U. Wash., (1999), Accessed Jul. 6, 2002.

R.A. Lerner, "Tapping the immunological repertoire to produce antibodies of predetermined specificity." Nature, vol. 299, pp. 592-596 (1982).

R.A. Lerner, "Antibodies of predetermined specificity in biology and medicine," Advances in Immunology, vol. 36, pp. 1-44, Academic Press (1984).

Hirotani et al., "Complement permeability in bio-artificial endocrine pancreas using a diffusion chamber," Cell Transplanation, vol. 7(4), pp. 407-410 (1998).

* cited by examiner

FIG. 1

Human glycoprotein hormone β10 polypeptide:

MRLAFLFLGFMALLLLAGYGCVLGASSQNLRTPVGCAVREFTFLAKKPGCRGLRITTDACWGRCET

WEKPILEPPYIEAHHRVCTYNETKQVTVKLENCAPGVDPFTYTYPVAIRCDCGACSTATTECETI

Nucleic acid encoding human glycoprotein hormone β10 polypeptide:

ATGAAGCTGGCATTCCTCTTCCTTGGCTTCATGGCCCTCCTCCTTCTGGC
TGGCTACTGGCCTGTGTCCTCGGCCAGTGGGCAGAACCTGCGCACCCTTTG
TGGGCTGTGCGTGAGGGAGTTCACTTTCCTGGCCAAGAAGCCAGGCTGC
AGGGGCCTTCGCATCACCACGGATGCCTGCTGGGGTCGCTGTGAGACCTG
GGAGAAACCCATTCTGGAACCATACATTGAAGCCCATCATCGAGTCT
GTACCTACAACGAGACCAAACAGGTGACTGTCAAGCTGGAAACTGTGCC
CCGGAGTCGACCTGCACCCTCTACACCTACACGGAGTCTGAGATCGTGACTG
CGGAGCCTGCTCCAGTGCACCACGGAGTGTGAGACCATCTGAGGCCGCT
AGCTGCTCTCTGCAGACCCACCTGTGTGAGCAGCACATGC

FIG. 2A

```
GAP OF: HUMAN TSH-β   CHECK: 4247   FROM: 1   TO: 118

TO: HUMAN β10    CHECK: 6611   FROM: 1   TO: 106

SYMBOL COMPARISON TABLE:
/GCGDISK/GCG10/GCGCORE/DATA/RUNDATA/BLOSUM62.CMP
 COMPCHECK: 6430

GAP WEIGHT:        8      AVERAGE MATCH:   2.912
   LENGTH WEIGHT:        2      AVERAGE MISMATCH: -2.003

QUALITY:      140            LENGTH:     129
           RATIO:    1.321              GAPS:       4
PERCENT SIMILARITY: 47.368    PERCENT IDENTITY: 36.842

MATCH DISPLAY THRESHOLDS FOR THE ALIGNMENT(S):
                     | = IDENTITY
                     : = 2
                     . = 1

HUMAN TSH-β   X   HUMAN β10

1 ..........FCIPTEYTMHIERRECAYCLTINTTICAGYCMTRDINGKL  40
             | |:|  .:  |  ||||  ||||   |  | :    :
 1 ASSGNLRTFVGCAVREFTFLAKKPGCR.GLRITTDACWGRCETWE..KPI  47

41 FLPKYALSQD.VCTYRDFIYRTVEIPGCPLHVAPYFSYPVALSCKCGKCN  89
   ||  | .   ||||  :    ||.:|   |   |::.||||: || |.
48 LEPPYIEAHHRVCTYNETKQVTVKLPNCAPGVDPFYTYPVAIRCDCGACS  97

90 TDYSDCIHEAIKTNYCTKPQKSYLVGFSV 118
   |  .: ||
98 TATTEC..ETI................. 106
```

FIG. 2B

```
GAP OF: HUMAN FSH-β    CHECK: 8841   FROM: 1  TO: 111

TO: HUMAN β10        CHECK: 6611   FROM: 1  TO: 106

SYMBOL COMPARISON TABLE:
/GCGDISK/GCG10/GCGCORE/DATA/RUNDATA/BLOSUM62.CMP
 COMPCHECK: 6430

GAP WEIGHT:       8       AVERAGE MATCH:     2.912
     LENGTH WEIGHT:       2    AVERAGE MISMATCH:    -2.003

QUALITY:     156              LENGTH:       122
             RATIO:   1.472                GAPS:         3
 PERCENT SIMILARITY: 44.211     PERCENT IDENTITY:    35.789

MATCH DISPLAY THRESHOLDS FOR THE ALIGNMENT(S):
                      | = IDENTITY
                      : = 2
                      . = 1

HUMAN FSH-β  X  HUMAN β10

1 ........NSCELTNITIAIEKEECRFCISINTTWCAGYCYTRDL.VYK  40
             |.  |  .| :  ||   ||  ||| |     :  :.
   1 ASSGNLRTPVGCAVREFTPLAKKPGCR.GLRITTDACWGRCETWEKPILE 49

41 DPARPKIQKTCTFKELVYETVRVPGCAHHADSLYTYPVATQCHCGKCDSD 90
     |    : ||: |    ||:.|| |     ||||||.|||  |.
  50 PPYIEAHHRVCTYNETKQVTVKLPNCAPGVDPFYTYPVAIRCDCGACSTA 99

91 STDC.TVRGLGPSYCSFGEMKE 111
     .|:.| |:
 100 TTECETI............... 106
```

FIG. 2C

```
GAP OF: HUMAN LH-β  CHECK: 5679  FROM: 1  TO: 121

TO: HUMAN β10  CHECK: 6611  FROM: 1  TO: 106

SYMBOL COMPARISON TABLE:
/GCGDISK/GCG10/GCGCORE/DATA/RUNDATA/BLOSUM62.CMP
  COMPCHECK: 6430

GAP WEIGHT:       8      AVERAGE MATCH:    2.912
     LENGTH WEIGHT:       2      AVERAGE MISMATCH: -2.003

QUALITY:      140            LENGTH:       125
            RATIO:    1.321              GAPS:         3
PERCENT SIMILARITY:  44.118   PERCENT IDENTITY:    32.353

MATCH DISPLAY THRESHOLDS FOR THE ALIGNMENT(S):
                   | = IDENTITY
                   : = 2
                   . = 1

HUMAN LH-β   X   HUMAN β10

1 .SREPLRPW..CHPINAILAVEKEGCPVCITVNTTICAGYCPTMMR.VLQ 46
    .|||.|    .||    .|| :;| ||||    ;|;
  1 ASSGNLRTFVGCAVREFTFLAKKPGCR.GLRITTDACWGRCETWEKPILE 49

47 AVLPPLPQVVCTYRDVRFESIRLPGCPRGVDPVVSFPVALSCRCGPCRRS 96
    ||| : . .:;|| | ||| .:|||: |||| .
 50 PPYIEAHHRVCTYNETKQVTVKLPNCAPGVDPFYTYPVAIRCDCGACSTA 99

97 TSDCGGPKDHPLTCDHPQLSGLLFL 121
    |.:|
100 TTECETI.................. 106
```

FIG. 2D

```
GAP OF: HUMAN CG-β   CHECK: 2358   FROM: 1 TO: 145

TO: HUMAN β10      CHECK: 6611   FROM: 1 TO: 106

SYMBOL COMPARISON TABLE:
/GCGDISK/GCG10/GCGCORE/DATA/RUNDATA/BLOSUM62.CMP
  COMPCHECK: 6430

GAP WEIGHT:      8      AVERAGE MATCH:   2.912
      LENGTH WEIGHT:      2      AVERAGE MISMATCH: -2.003

QUALITY:    131            LENGTH:    149
              RATIO:  1.236              GAPS:      3
  PERCENT SIMILARITY: 42.157    PERCENT IDENTITY: 31.373

MATCH DISPLAY THRESHOLDS FOR THE ALIGNMENT(S):
                      | = IDENTITY
                      : = 2
                      . = 1

HUMAN CG-β   X   HUMAN β10

1 .SKEPLRP..RCRPINATLAVEKEGCPVCITVNTTICAGYCPTMTR.VLQ 46
    .|  ||    |   |      .|  |    : :  |  | ||   ; ;|:
  1 ASSGNLRTFVGCAVREFTFLAKKPGCR.GLRITTDACWGRCETWEKPILE 49

47 GVLPALPQVVCNYRDVRFESIRLPGCPRGVNPVVSYAVALSCQCALCRRS 96
    ||   |  ;    .::||  |   ||.  .| ||: | | |        .
 50 PPYIEAHHRVCTYNETKQVTVKLPNCAPGVDPFYTYPVAIRCDCGACSTA 99

97 TTDCGSPKDHPLTCDDPRFQDSSSSKAPPPSLPSPSRLPGPSDTPILPQ 145
    || :|
100 TTECETI......................................... 106
```

FIG. 4

```
BESTFIT of: human β10    check: 6611  from: 1  to: 106 to: mouse β10   check: 7740  from: 1  to: 106

Symbol comparison table: blosum62.cmp CompCheck: 6430
BLOSUM62 amino acid substitution matrix.
Reference: Henikoff, S. and Henikoff, J. G. (1992). Amino acid
           substitution matrices from protein blocks. Proc. Natl. Acad.
           Sci. USA 89: 10915-10919.

Gap Weight:       8      Average Match:    2.912
      Length Weight:       2      Average Mismatch: -2.003

Quality:     577             Length:     106
              Ratio:   5.443               Gaps:       0
 Percent Similarity:  97.170    Percent Identity:  93.396

Match display thresholds for the alignment(s):
                    | = IDENTITY
                    : = 2
                    . = 1 human β10  x  mouse β10

1 ASSGNLRTFVGCAVREFTFLAKKPGCRGLRITTDACWGRCETWEKPILEP  50
       .||||||||||||||||||| |||||||||||||||||||||||||||||
     1 SSSGNLRTFVGCAVREFTFMAKKPGCRGLRITTDACWGRCETWEKPILEP  50

51 PYIEAHHRVCTYNETKQVTVKLPNCAPGVDPFYTYPVAIRCDCGACSTAT 100
       |||||:|||||||||||:|||||||||||||||||| .|:||||||||||
    51 PYIEAYHRVCTYNETRQVTVKLPNCAPGVDPFYTYPMAVRCDCGACSTAT 100

101 TECETI 106
       ||||||
   101 TECETI 106
```

ANTIBODIES THAT SPECIFICALLY BIND BETA-LIKE GLYCOPROTEIN HORMONE POLYPEPTIDES AND HETERODIMERS THEREOF

This application is a divisional of U.S. application Ser. No. 12/072,822 filed Feb. 27, 2008 now U.S. Pat. No. 7,883,868, which is a continuation of 09/818,954 filed Mar. 27, 2001, now U.S. Pat. No. 7,514,239, which is a continuation-in-part of U.S. application Ser. No. 09/723,970, filed Nov. 27, 2000 now abandoned, which claims the benefit of U.S. Provisional Application Ser. No. 60/199,211, filed Apr. 24, 2000, and U.S. Provisional Application Ser. No. 60/192,654, filed Mar. 28, 2000, which are hereby incorporated by reference.

FIELD OF THE INVENTION

The present invention relates to a novel beta-like member (referred to herein as "beta-10" or "β10") of the glycoprotein hormone family and nucleic acid molecules encoding same. The invention also relates to a novel heterodimeric glycoprotein hormone comprising beta-10 and alpha-2 as the subunits. The invention also relates to vectors, host cells, selective binding agents, such as antibodies, and methods for producing beta-10 polypeptides and the disclosed beta-10 heterodimer. Also provided for are methods for the use of beta-10 and the beta-10 heterodimer and selective beta-10 and beta-10 heterodimer binding agents, including methods for the diagnosis and treatment of disorders associated with beta-10 or the beta-10 heterodimer.

BACKGROUND OF THE INVENTION

As generally accepted in the art, there are currently five known glycoprotein hormone polypeptides produced in humans: alpha-subunit, TSH-(thyroid stimulating hormone)-β-subunit, FSH-(follicle stimulating hormone)-β-subunit, LH-(luteinizing hormone)-β-subunit, and CG-(chorionic gonadotropin)-β-subunit; Thotakura and Blithe, Glycobiology, Volume 5, pages 3-10 (1995); Wondisford et al. in Volume 1, Endocrinology (edited by L. DeGroot), pages 208-217, W. B. Saunders Company, Philadelphia, Pa. (1995); Moyle and Campbell, in Volume 1, Endocrinology (edited by L. DeGroot), pages 230-241, W. B. Saunders Company, Philadelphia, Pa. (1995). These polypeptides are produced by single genes, with the exception of the CG-β-subunit which is encoded by a multigene cluster composed of six homologous sequences linked to the single LH-β-subunit gene on chromosome 19; Bo and Boime, Journal of Biological Chemistry, vol. 267, pp. 3179-3184 (1992).

Monomeric alpha-subunit (FAS, or free alpha-subunit) has hormonal activity and is secreted by the pituitary gland and the placenta. FAS has been found to play a role in the differentiation of prolactin producing cells in the pituitary and placenta; see Begeot et al., Science, vol. 226, pp. 566-568 (1984), Van-Bael and Denef, Journal of Neuroendocrinology, vol. 8, pp. 99-102 (1996), and Moy et al., Endocrinology, vol. 137, pp. 1332-1339 (1996); and also to stimulate placental prolactin secretion; see Blithe et al., Endocrinology, vol. 129, pp. 2257-2259 (1991).

Alpha-subunit also heterodimerizes with each of the four beta-subunits to form four heterodimeric hormones (TSH, FSH, LH and CG). TSH, FSH and LH are produced in the pituitary, stored in secretion granules, and secreted when the appropriate releasing hormone is produced by the hypothalamus. CG is produced in the placenta and appears to be secreted constitutively (it is not stored in secretion granules); see Wondisford et al. in Volume 1, Endocrinology (ed. L. DeGroot), pp. 208-217, above, and Hall and Crowley, Jr. in Volume 1, Endocrinology (ed. L. DeGroot), pp. 242-258, W. B. Saunders Company, Philadelphia, Pa. (1995).

TSH influences basal metabolism by regulating the production of thyroid hormones and is used clinically for enhancing the detection and treatment of thyroid carcinoma; see McEvoy, G. (ed.), AHFS Drug Information, pp. 2041-2042, American Society of Health-System Pharmacists, Inc., Bethesda, Md. (1998). In addition, diagnostic tests for measuring TSH levels in the blood are commonly used for determining the functional status of the thyroid gland when thyroid gland disorder is suspected.

FSH and LH play important roles in the maintenance of reproductive function in males and females (i.e., gonadal maturation and gonadal steroid production). CG is involved in the maintenance of pregnancy by stimulating the corpus luteum to produce steroid hormones during the first trimester. FSH, LH and CG are used clinically to treat infertility and also as reagents in assisted reproduction procedures such as in vitro fertilization (IVF); see McEvoy, G. (ed.), AHFS Drug Information, pp. 2564-2567, American Society of Health-System Pharmacists, Inc., Bethesda, Md. (1998). Diagnostic tests for measuring FSH, LH and CG levels are used for the diagnosis of fertility disorders, as well as to test for pregnancy.

Naturally occurring metabolites of the above mentioned glycoprotein hormone polypeptides have been described, such as the β-core fragment which is derived from the beta subunit of CG, but no function has yet been assigned to these metabolites; Moyle and Campbell in Volume 1 Endocrinology (ed. L. DeGroot) pp. 230-241, above.

In 1994, the five known glycoprotein hormone polypeptides were placed into the cystine-knot growth factor structural superfamily, based on the crystal structure of human CG; Lapthorn et al., Nature, vol. 369, pp. 455-61 (1994). This superfamily includes the TGF-β (transforming growth factor beta), NGF (nerve growth factor) and PDGF (platelet-derived growth factor) gene families. The cystine-knot is formed by three intramolecular disulfide bonds, has a very characteristic structure, and is responsible for the overall three-dimensional structure of all of the members of the superfamily; Isaacs, Current Opinion in Structural Biology, vol. 5, pp. 391-395 (1995). A recently published patent application describes a novel member of the cystine-knot family (zsig51); Sheppard and Lok, (1999) WIPO patent application WO99/41377. zsig51 has in fact been determined to be a new, alpha-like, member of the glycoprotein hormone family and will thus be referred to here as "α2" or "alpha-2" [Paszty et al. (2000) WIPO patent application WO 00/78964].

SUMMARY OF THE INVENTION

The present invention provides, in part, an isolated secretable human polypeptide (SEQ ID NO: 1) which is a novel beta-like member of the glycoprotein hormone family and is herein designated as "beta-10" or "β10".

The full length amino acid sequence of human β10 in accordance with this invention is shown in FIG. 1. The N-terminal signal peptide predicted for the β10 polypeptide is shown underlined. The asparagine (N) at position 87 of SEQ ID NO: 1 is located within a classic NxT glycosylation motif (where x denotes any amino acid except for proline and T denotes threonine) and is likely to be glycosylated. The signal peptide cleavage site in the β10 amino acid sequence is expected to be within the region of eight amino acids shown boxed in FIG. 1. Signal peptide cleavage at the site which is most likely to be the authentic in vivo cleavage site is reflected in the sequence of the "mature" β10 polypeptide (SEQ ID NO: 3).

The most likely "mature" form (i.e., processed in situ to remove the signal peptide) of β10 polypeptide was run against the NonRedundant Protein database using the computer analysis program known as BLAST to examine homologies (specifically, commonly occurring or "conserved" amino acid residues) to known proteins. The top 112 "hits" were found to be various glycoprotein hormone β-subunits from various mammalian, bird and fish species. These homologies clearly indicated that β10 is a new β-like member of the glycoprotein hormone family.

Further, GAP analysis indicated that the homology of β10 to the four known human glycoprotein hormone β-subunits (mentioned above) was 31-37% identity and 42-48% similarity (see FIG. 2A-D, referred to hereinbelow). The mature forms of the four known human β glycoprotein hormone polypeptides contain twelve cysteine residues, which form six intramolecular disulfide bonds. The mature form of the human β10 polypeptide of the present invention contains ten cysteine residues, which are likely to form five intramolecular disulfide bonds. Using the disulfide bond cysteine pairing of CG-β as a model, the most likely disulfide bond cysteine pairing for the five putative disulfide bonds in the β10 polypeptide of this invention is as follows: C12-C60, C26-C75, C36-C91, C40-C93 and C96-C103 of SEQ ID NO: 3 (see also FIG. 3).

The full length amino acid sequence of mouse β10 polypeptide is set forth in SEQ ID NO: 11 and the nucleotide sequence of the full coding region of the mouse β10 cDNA is set forth in SEQ ID NO: 12. Signal peptide cleavage at the site which is most likely to be the authentic in vivo cleavage site is reflected in the sequence of the "mature" form mouse β10 polypeptide (SEQ ID NO: 13). BestFit analysis indicated that the amino acid homology of mature form human β10 polypeptide as compared to mature form mouse β10 polypeptide was 93.4% identity and 97.2% similarity (see FIG. 4, referred to herein below).

Based on the logical inclusion of the β10 polypeptide of this invention in the glycoprotein hormone family, this polypeptide could be a monomer (analogous to FAS and β-core fragment) and/or could form a heterodimer with one or more glycoprotein hormone family polypeptides (for example heterodimers α/β10, β10/TSH-β, β10/LH-β). The β10 polypeptide could also form heterodimers with polypeptides which are distinct from the known glycoprotein hormone polypeptides. Based on these various possibilities, the β10 polypeptide may form more than one hormone (i.e., the β10 hormones).

A heterodimerization assay was used to determine that human β10 forms a heterodimer with human α2 polypeptide, described in the above mentioned WO99/41377 and WO 00/78964 patent applications, thus discovering and defining a novel heterodimeric glycoprotein hormone, α2/β10.

The general principle of the heterodimerization assay for secreted proteins, such as the glycoprotein hormones, is co-transfection of the two distinct genes into mammalian cells, collection of conditioned media, immunoprecipitation with an antibody that specifically binds to one of the gene products and Western blotting of the immunoprecipitate with an antibody that specifically binds to the other gene product. With the proper control experiments in place, the presence of a band of the correct size on the Western would indicate heterodimerization of the two gene products under the experimental conditions of the assay, whereas the absence of a band of the correct size on the Western would indicate that the two gene products did not heterodimerize under the experimental conditions of the assay. Because the known heterodimeric glycoprotein hormones (LH, FSH, TSH and CG) can readily be produced by co-transfection of mammalian cells with the appropriate genes, this type of mammalian cell based co-transfection heterodimerization assay is relevant for members of the glycoprotein hormone family.

A human α2-polyHis-tag mammalian expression vector and a human β10-FLAG-tag mammalian expression vector were co-transfected into 293 cells and serum free conditioned media was harvested after 72 hours. Immunoprecipitation was done using anti-FLAG M2-Agarose affinity beads (Cat# A1205, Sigma, St. Louis, Mo.). A Western blot of this immunoprecipitate was probed with affinity purified anti-α2 rabbit polyclonal antibodies (example 4) that had been conjugated to Horse Radish Peroxidase (Linx HRP Rapid Protein Conjugation Kit, cat# K8050-01, Invitrogen Corp., Carlsbad, Calif.). A strong α2-polyHis-tag band was observed using the ECL Western Blot detection kit (cat#RPN 2106, Amersham Pharmacia Biotech, Piscataway, N.J.). Control experiments showed that the presence of the strong α2-polyHis-tag band on the Western blot was entirely dependent on co-transfection with the human β10-FLAG-tag mammalian expression vector and the use of anti-FLAG M2-Agarose affinity beads. No α2-polyHis-tag band was observed if either of these 2 components was left out of the experiment or if plain agarose beads (i.e. without anti-FLAG antibodies) were used for the immunoprecipitation step.

Similar to the known heterodimeric glycoprotein hormones (TSH, FSH, LH and CG) α2/β10 is a heterodimer of an alpha-like glycoprotein hormone polypeptide and a beta-like glycoprotein hormone polypeptide.

These data also indicate that recombinant, secreted α2/β10 heterodimer (without polyHis and FLAG affinity tags) can be produced in mammalian cells for various therapeutic and diagnostic utilities as described further below.

Heterodimeric glycoprotein hormones such as CG can also be assembled in vitro upon co-incubation of, for example, isolated alpha-subunit and isolated CG-β subunit under suitable conditions [see Blithe and Iles, Endocrinology, volume 136, pages 903-910 (1995)]. α2/β10 heterodimer could similarly be assembled in vitro upon co-incubation of isolated α2 polypeptide and isolated β10 polypeptide. Such assembled α2/β10 heterodimer could be used for various therapeutic and diagnostic utilities as described further below.

Transgenic mice were made that over expressed mouse α2 alone, mouse β10 alone or the mouse α2/β10 heterodimer (see example 6). Only those transgenics over expressing the α2/β10 heterodimer showed distinct phenotypic differences as compared to control mice. The α2/β10 overexpressor transgenic mice exhibited a phenotype characterized by bilateral thyroid enlargement with multiple follicular papillary adenomas and resulting hyperthyroidism, as indicated by elevated serum T4 levels. Other phenotypic changes were felt to be related to the systemic hyperthyroid state, and included moderate hepatomegaly, hepatocellular hyperplasia, and slightly decreased serum cholesterol levels, bilateral renal hypertrophy, and a mild to moderate leukocytosis with a predominance of lymphocytes (see example 6). Thus in a normal mouse setting α2/β10 clearly has a thyroid stimulating hormone (TSH) like activity. Due to the high level of amino acid conservation between mouse α2 and human α2 [88.5% identity and 90.4% similarity for the predicted mature forms (i.e. without signal peptide)], the high level of amino acid conservation between mouse β10 and human β10 [93.4% identity and 97.2% similarity for the predicted mature forms (i.e. without signal peptide)], and the very high level of similarity between mouse thyroid gland biology and human thyroid gland biology, it is anticipated that human α2/β10 heterodimer has the same thyroid stimulating hormone (TSH) like activity as that found for the mouse α2/β10 heterodimer. In addition to TSH-like activity, α2/β10 may have other, distinct, biological effects in different physiological settings (i.e., disease conditions), as described in greater detail further herein.

TSH influences basal metabolism by regulating the production of thyroid hormones and is used clinically for enhancing the detection and treatment of thyroid carcinoma; see McEvoy, G. (ed.), *AHFS Drug Information*, pp. 2041-2042, American Society of Health-System Pharmacists, Inc., Bethesda, Md. (1998). In addition, diagnostic tests for measuring TSH levels in the blood are commonly used for determining the functional status of the thyroid gland when thyroid gland disorder is suspected. It is likely that human α2/β10 will have similar clinical utilities as TSH and will be useful for the treatment and diagnosis of thyroid gland related diseases and disorders. In addition, human α2/β10 may have other therapeutic and diagnostic uses which are described herein. It is reasonable to surmise that human α2/β10 selective binding agents, for example, antibodies, will have similar clinical utilities to TSH selective binding agents and will therefore be useful for the treatment and diagnosis of thyroid gland related diseases and disorders. In addition, human α2/β10 selective binding agents may have other therapeutic and diagnostic uses as described herein.

This invention also provides for an isolated nucleic acid molecule comprising a nucleotide sequence selected from the group consisting of:

(a) the nucleotide sequence set forth in SEQ ID NO: 2;

(b) a nucleotide sequence encoding the polypeptide set forth in SEQ ID NO: 1;

(c) a nucleotide sequence which hybridizes under moderately or highly stringent conditions to the complement of (a) or (b), wherein the encoded polypeptide, when heterodimerized to human α2 polypeptide, has an activity of the human α2/β10 heterodimer; and (d) a nucleotide sequence complementary to any of (a)-(c).

The invention also provides for an isolated nucleic acid molecule comprising a nucleotide sequence selected from the group consisting of:

(a) a nucleotide sequence encoding a polypeptide that is at least about 70, 75, 80, 85, 90, 95, 96, 97, 98, or 99 percent identical to the polypeptide as set forth in SEQ ID NO: 1, wherein the polypeptide, when heterodimerized to human α2 polypeptide, has an activity of the human α2/β10 heterodimer;

(b) a nucleotide sequence encoding an allelic variant or splice variant of the nucleotide sequence set forth in SEQ ID NO: 2, wherein the encoded polypeptide, when heterodimerized to human α2 polypeptide, has an activity of the human α2/β10 heterodimer;

(c) a nucleotide sequence of SEQ ID NO: 2, (a), or (b) encoding a polypeptide fragment of at least about 25 amino acid residues, wherein the polypeptide, when heterodimerized to human α2 polypeptide, has an activity of the human α2/β10 heterodimer;

(d) a nucleotide sequence of SEQ ID NO: 2 or (a)-(c) comprising a fragment of at least about 16 nucleotides;

(e) a nucleotide sequence which hybridizes under moderately or highly stringent conditions to the complement of any of (a)-(d), wherein the encoded polypeptide, when heterodimerized to human α2 polypeptide, has an activity of the human α2/β10 heterodimer; and (f) a nucleotide sequence complementary to any of (a)-(d).

The invention further provides for an isolated nucleic acid molecule comprising a nucleotide sequence selected from the group consisting of:

(a) a nucleotide sequence encoding a polypeptide as set forth in SEQ ID NO: 1 with at least one conservative amino acid substitution, wherein the polypeptide, when heterodimerized to human α2 polypeptide, has an activity of the human α2/β10 heterodimer;

(b) a nucleotide sequence encoding a polypeptide as set forth in SEQ ID NO: 1 with at least one amino acid insertion, wherein the polypeptide, when heterodimerized to human α2 polypeptide, has an activity of the human α2/β10 heterodimer;

(c) a nucleotide sequence encoding a polypeptide as set forth in SEQ ID NO: 1 with at least one amino acid deletion, wherein the polypeptide, when heterodimerized to human α2 polypeptide, has an activity of the human α2/β10 heterodimer;

(d) a nucleotide sequence encoding a polypeptide as set forth in SEQ ID NO: 1 which has a C- and/or N-terminal truncation, wherein the polypeptide, when heterodimerized to human α2 polypeptide, has an activity of the human α2/β10 heterodimer;

(e) a nucleotide sequence encoding a polypeptide as set forth in SEQ ID NO: 1 with at least one modification selected from the group consisting of amino acid substitutions, amino acid insertions, amino acid deletions, C-terminal truncation, and N-terminal truncation, wherein the polypeptide, when heterodimerized to human α2 polypeptide, has an activity of the human α2/β10 heterodimer;

(f) a nucleotide sequence of (a)-(e) comprising a fragment of at least about 16 nucleotides;

(g) a nucleotide sequence which hybridizes under moderately or highly stringent conditions to the complement of any of (a)-(f), wherein the encoded polypeptide, when heterodimerized to human α2 polypeptide, has an activity of the human α2/β10 heterodimer; and (h) a nucleotide sequence complementary to any of (a)-(e).

The invention also provides for an isolated polypeptide comprising the amino acid sequence selected from the group consisting of:

(a) the mature amino acid sequence set forth in SEQ ID NO: 3, and optionally further comprising an amino-terminal methionine;

(b) an amino acid sequence for an ortholog of SEQ ID NO: 3, wherein the encoded polypeptide, when heterodimerized to human α2 polypeptide, has an activity of the human α2/β10 heterodimer;

(c) an amino acid sequence that is at least about 70, 75, 80, 85, 90, 95, 96, 97, 98, or 99 percent identical to the amino acid sequence of SEQ ID NO: 3, wherein the polypeptide, when heterodimerized to human α2 polypeptide, has an activity of the human α2/β10 heterodimer;

(d) a fragment of the amino acid sequence set forth in SEQ ID NO: 3 comprising at least about 25 amino acid residues, wherein the polypeptide, when heterodimerized to human α2 polypeptide, has an activity of the human α2/β10 heterodimer;

(e) an amino acid sequence for an allelic variant or splice variant of either the amino acid sequence as set forth in SEQ ID NO: 3, or at least one of (a)-(c) wherein the polypeptide, when heterodimerized to human α2 polypeptide, has an activity of the human α2/β10 heterodimer.

The invention further provides for an isolated polypeptide comprising the amino acid sequence selected from the group consisting of:

(a) the amino acid sequence as set forth in SEQ ID NO: 3 with at least one conservative amino acid substitution, wherein the polypeptide, when heterodimerized to human α2 polypeptide, has an activity of the human α2/β10 heterodimer;

(b) the amino acid sequence as set forth in SEQ ID NO: 3 with at least one amino acid insertion, wherein the polypeptide, when heterodimerized to human α2 polypeptide, has an activity of the human α2/β10 heterodimer;

(c) the amino acid sequence as set forth in SEQ ID NO: 3 with at least one amino acid deletion, wherein the polypeptide, when heterodimerized to human α2 polypeptide, has an activity of the human α2/β10 heterodimer;

(d) the amino acid sequence as set forth in SEQ ID NO: 3 which has a C- and/or N-terminal truncation, wherein the polypeptide, when heterodimerized to human α2 polypeptide, has an activity of the human α2/β10 heterodimer; and (e) the amino acid sequence as set forth in SEQ ID NO: 3, with at least one modification selected from the group consisting of amino acid substitutions, amino acid insertions, amino acid deletions, C-terminal truncation, and N-terminal truncation, wherein the polypeptide, when heterodimerized to human α2 polypeptide, has an activity of the human α2/β10 heterodimer.

Also provided are fusion polypeptides comprising the amino acid sequences of (a)-(e) above.

The present invention also provides for an expression vector comprising the isolated nucleic acid molecules as set forth herein, recombinant host cells comprising recombinant nucleic acid molecules as set forth herein, and a method of producing a β10 polypeptide or an α2/β10 heterodimer of this invention comprising culturing the host cells and optionally isolating the β10 polypeptide or α2/β10 heterodimer so produced.

A transgenic non-human animal comprising a nucleic acid molecule(s) encoding a β10 polypeptide or α2/β10 heterodimer of this invention is also encompassed by the invention. The nucleic acid molecules are introduced into the animal in a manner that allows expression and increased levels of β10 polypeptide or α2/β10 heterodimer, which may include increased circulating levels. The transgenic non-human animal is preferably a mammal.

Also provided are derivatives of the β10 polypeptide or α2/β10 heterodimer of the present invention.

Additionally provided are selective binding agents such as antibodies and peptides capable of specifically binding the β10 polypeptide or α2/β10 heterodimer of the invention. Such antibodies and peptides may be agonistic or antagonistic to an activity of the β10 polypeptide or α2/β10 heterodimer.

Pharmaceutical compositions comprising the nucleotides, β10 polypeptide or α2/β10 heterodimer, or selective binding agents of the present invention and one or more pharmaceutically acceptable formulation agents are also encompassed by the invention. The pharmaceutical compositions are used to provide therapeutically effective amounts of the nucleotides or polypeptides of the present invention. The invention is also directed to methods of using the nucleic acid molecules, β10 polypeptide, α2/β10 heterodimer and selective binding agents.

The nucleic acid molecules, β10 polypeptide, α2/β10 heterodimer and selective binding agents of the present invention may be used to treat, prevent, ameliorate, and/or detect diseases and disorders, including those recited herein.

The present invention also provides a method of assaying test molecules to identify a test molecule which binds to a β10 polypeptide or α2/β10 heterodimer. The method comprises contacting the β10 polypeptide or α2/β10 heterodimer with a test molecule and determining the extent of binding of the test molecule to the β10 polypeptide or α2/β10 heterodimer. The method further comprises determining whether such test molecules are agonists or antagonists of the β10 polypeptide or α2/β10 heterodimer. The present invention further provides a method of testing the impact of molecules on the expression of the β10 polypeptide or α2/β10 heterodimer or on the activity of the β10 polypeptide or α2/β10 heterodimer.

Methods of regulating expression and modulating (i.e., increasing or decreasing) levels of a β10 polypeptide or α2/β10 heterodimer of this invention are also encompassed by the invention. One method comprises administering to an animal a nucleic acid molecule(s) encoding such a β10 polypeptide or α2/β10 heterodimer. In another method, a nucleic acid molecule comprising elements that regulate or modulate expression of the β10 polypeptide or α2/β10 heterodimer of this invention may be administered. Examples of these methods include gene therapy, cell therapy, and antisense therapy as further described herein.

BRIEF DESCRIPTION OF THE FIGURES

FIG. 1 depicts in linear array the full coding region of human β10 polypeptide in accordance with this invention (SEQ ID NO: 1). The predicted signal peptide region is underlined and the region containing the predicted signal peptide cleavage site is boxed. The asparagine (N) residue that is located within the classic NxT glycosylation motif, and which is very likely to be glycosylated, is shown in larger font. The corresponding nucleic acid sequence which encodes this polypeptide (SEQ ID NO: 2) comprises nucleotides 1-390, inclusive, of the nucleic acid sequence shown in this Figure.

FIG. 2A-2D illustrates the relatedness of the known human glycoprotein hormone β-subunit polypeptides (prior art) and the β10 polypeptide of this invention. The mature form of β10 used for these comparisons (SEQ ID NO: 3) most likely represents the authentic in vivo form of β10 polypeptide. FIGS. 2A-D comprise the GAP output showing the amino acid homology between the mature form of β10 and respectively, TSH-(thyroid stimulating hormone)-β-subunit, FSH-(follicle stimulating hormone)-β-subunit, LH-(luteinizing hormone)-β-subunit, and CG-(chorionic gonadotropin)-β-subunit.

FIG. 4 is the BestFit output showing the amino acid homology between the mature form of human β10 and the mature form of mouse β10 The mature form of human β10 used for this comparison (SEQ ID NO: 3) most likely represents the authentic in vivo form of human β10 polypeptide. The mature form of mouse β10 used for this comparison (SEQ ID NO: 13) most likely represents the authentic in vivo form of mouse β10 polypeptide.

DETAILED DESCRIPTION OF THE INVENTION

Figure 3:
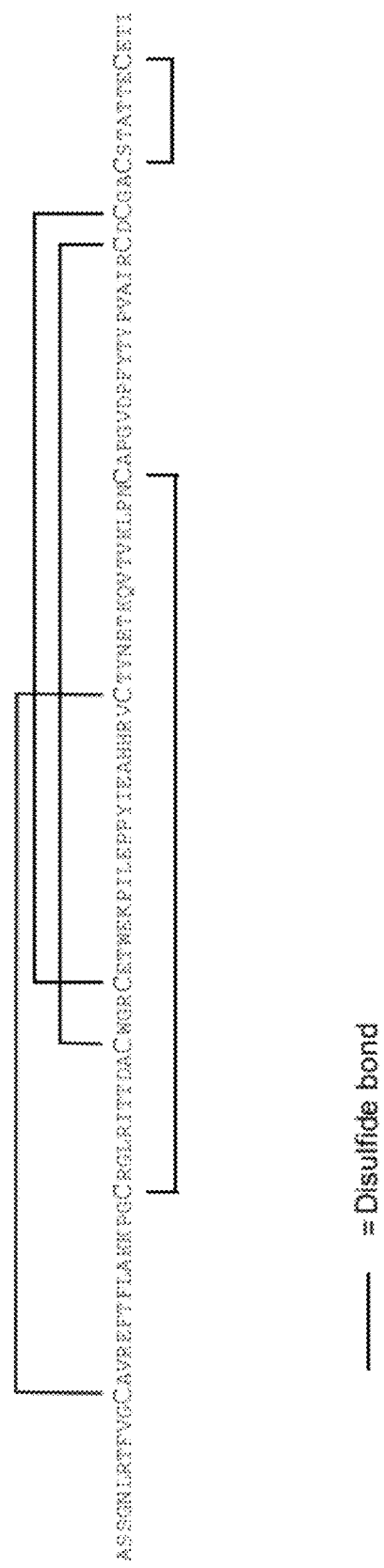
FIG. 3 shows the likely disulfide bond cysteine (C) pairs of the five putative disulfide bonds in the most likely mature form of human β10 (SEQ ID NO: 3). The ten cysteine residues are shown in large font and the disulfide bonds are drawn as solid lines. The three disulfide bonds (C12-C60, C36-C91, C40-C93) that form the cystine-knot are drawn above the amino acid sequence, and the two additional disulfide bonds (C26-C75, C96-C103) are drawn below the amino acid sequence.

The section headings used herein are for organizational purposes only and are not to be construed as limiting the subject matter described. All references cited in this application are expressly incorporated by reference herein.

Definitions

The terms "β10 gene" or "β10 nucleic acid molecule" or "polynucleotide" refers to a nucleic acid molecule comprising or consisting of a nucleotide sequence as set forth in SEQ ID NO: 2, a nucleotide sequence encoding the polypeptide as set forth in SEQ ID NO: 1, a nucleotide of the DNA insert in ATCC deposit no. PTA-1210, and nucleic acid molecules as defined herein.

The term "β10 polypeptide" refers to a polypeptide comprising the amino acid sequence of SEQ ID NO: 3, and related polypeptides. Related polypeptides include: β10 polypeptide allelic variants, β10 polypeptide orthologs, β10 polypeptide splice variants, β10 polypeptide variants and β10 polypeptide derivatives. β10 polypeptides may be mature polypeptides, as defined herein, and may or may not have an amino terminal methionine residue, depending on the method by which they are prepared.

The term "β10 polypeptide allelic variant" refers to one of several possible naturally occurring alternate forms of a gene occupying a given locus on a chromosome of an organism or a population of organisms.

The term "β10 polypeptide derivatives" refers to the polypeptide set forth in SEQ ID NO: 3, polypeptide allelic variants thereof, polypeptide orthologs thereof, polypeptide splice variants thereof, or polypeptide variants thereof, as defined herein, that have been chemically modified.

The term "β10 polypeptide fragment" refers to a polypeptide that comprises a truncation at the amino terminus (with or without a leader sequence) and/or a truncation at the carboxy terminus of the polypeptide set forth in SEQ ID NO: 3, polypeptide allelic variants thereof, polypeptide orthologs thereof, polypeptide splice variants thereof and/or a polypeptide variant thereof having one or more amino acid additions or substitutions or internal deletions (wherein the resulting polypeptide is at least 6 amino acids or more in length) as compared to the β10 polypeptide amino acid sequence set forth in SEQ ID NO: 3. Polypeptide fragments may result from alternative RNA splicing or from in vivo protease activity. In preferred embodiments, truncations comprise about 10 amino acids, or about 20 amino acids, or about 50 amino acids, or about 75 amino acids, or about 100 amino acids, or more than about 100 amino acids. The polypeptide fragments so produced will comprise about 25 contiguous amino acids, or about 50 amino acids, or about 75 amino acids, or about 100 amino acids, or about 150 amino acids, or about 200 amino acids. Such polypeptide fragments may optionally comprise an amino terminal methionine residue. It will be appreciated that such fragments can be used, for example, to generate antibodies to β10 polypeptide or α2/β10 heterodimer.

The term "β10 fusion polypeptide" refers to a fusion of one or more amino acids (such as a heterologous peptide or polypeptide) at the amino or carboxy terminus of the polypeptide set forth in SEQ ID NO: 3, polypeptide allelic variants, polypeptide orthologs, polypeptide splice variants, or polypeptide variants having one or more amino acid deletions, substitutions or internal additions as compared to the β10 polypeptide amino acid sequence set forth in SEQ ID NO: 3.

The term "β10 polypeptide ortholog" refers to a polypeptide from another species that corresponds to the β10 polypeptide amino acid sequence set forth in SEQ ID NO: 3. For example, mouse and human β10 polypeptides are considered orthologs of each other.

The term "β10 polypeptide splice variant" refers to a nucleic acid molecule, usually RNA, which is generated by alternative processing of intron sequences in an RNA transcript of the β10 polypeptide amino acid sequence set forth in SEQ ID NO: 3.

The term "β10 polypeptide variants" refers to β10-like polypeptides comprising amino acid sequences having one or more amino acid sequence substitutions, deletions (such as internal deletions and/or polypeptide fragments), and/or additions (such as internal additions and/or fusion polypeptides) as compared to the β10 polypeptide amino acid sequence set forth in SEQ ID NO: 3. Variants may be naturally occurring (e.g., β10-like polypeptide allelic variants, polypeptide orthologs and polypeptide splice variants) or artificially constructed. Such polypeptide variants may be prepared from the corresponding nucleic acid molecules having a DNA sequence that varies accordingly from the DNA sequence set forth in SEQ ID NO: 2. In preferred embodiments, the variants have from 1 to 3, or from 1 to 5, or from 1 to 10, or from 1 to 15, or from 1 to 20, or from 1 to 25, or from 1 to 50, or from 1 to 75, or from 1 to 100, or more than 100 amino acid substitutions, insertions, additions and/or deletions, wherein the substitutions may be conservative, or non-conservative, or any combination thereof.

The term "α2/β10 heterodimer" refers to a heterodimer of the β10 polypeptide and the α2 polypeptide.

The term "antigen" refers to a molecule or a portion of a molecule capable of being bound by a selective binding agent, such as an antibody, and additionally capable of being used in an animal to produce antibodies capable of binding to an epitope of that antigen. An antigen may have one or more epitopes.

The term "biologically active β10 polypeptides" refers to β10-like polypeptides that, when heterodimerized to human α2 polypeptide, have an activity of the human α2/β10 heterodimer.

The terms "effective amount" and "therapeutically effective amount" each refer to the amount of a β10 nucleic acid molecule or a β10 polypeptide or α2/β10 heterodimer of this invention used to support an observable level of one or more biological activities of the α2/β10 heterodimer described herein.

The term "expression vector" refers to a vector which is suitable for use in a host cell and contains nucleic acid sequences which direct and/or control the expression of heterologous nucleic acid sequences. Expression includes, but is not limited to, processes such as transcription, translation, and RNA splicing, if introns are present.

The term "host cell" is used to refer to a cell which has been transformed, or is capable of being transformed with a nucleic acid sequence and then of expressing a selected gene of interest. The term includes the progeny of the parent cell, whether or not the progeny is identical in morphology or in genetic make-up to the original parent, so long as the selected gene is present.

The term "identity" as known in the art, refers to a relationship between the sequences of two or more polypeptide molecules or two or more nucleic acid molecules, as determined by comparing the sequences. In the art, "identity" also means the degree of sequence relatedness between nucleic acid molecules or polypeptides, as the case may be, as determined by the match between strings of two or more nucleotide or two or more amino acid sequences. "Identity" measures the percent of identical matches between the smaller of two or more sequences with gap alignments (if any) addressed by a particular mathematical model or computer program (i.e., "algorithms").

The term "similarity" is a related concept, but in contrast to "identity", refers to a measure of similarity which includes both identical matches and conservative substitution matches. If two polypeptide sequences have, for example, 10/20 identical amino acids, and the remainder are all non-conservative substitutions, then the percent identity and similarity would both be 50%. If in the same example, there are 5 more positions where there are conservative substitutions, then the percent identity remains 50%, but the percent similarity would be 75% (15/20). Therefore, in cases where there are conservative substitutions, the degree of similarity between two polypeptides will be higher than the percent identity between those two polypeptides.

The term "isolated nucleic acid molecule" refers to a nucleic acid molecule of the invention that is free from at least one contaminating nucleic acid molecule with which it is naturally associated. Preferably, the isolated nucleic acid molecule of the present invention is substantially free from any other contaminating nucleic acid molecule(s) or other contaminants that are found in its natural environment which would interfere with its use in polypeptide production or its therapeutic, diagnostic, prophylactic or research use.

The term "isolated polypeptide" refers to a polypeptide of the present invention that is free from at least one contaminating polypeptide or other contaminants that are found in its natural environment. Preferably, the isolated polypeptide is substantially free from any other contaminating polypeptides or other contaminants that are found in its natural environment which would interfere with its therapeutic, diagnostic, prophylactic or research use.

The term "mature β10 polypeptide" refers to a β10 polypeptide lacking a leader sequence. A mature β10 polypeptide may also include other modifications such as proteolytic processing of the amino terminus (with or without a leader sequence) and/or the carboxy terminus, cleavage of a smaller polypeptide from a larger precursor, N-linked and/or O-linked glycosylation, and the like.

The term "nucleic acid sequence" or "nucleic acid molecule" refers to a DNA or RNA sequence. The term encompasses molecules formed from any of the known base analogs of DNA and RNA such as, but not limited to 4-acetylcytosine, 8-hydroxy-N6-methyladenosine, aziridinyl-cytosine, pseudoisocytosine, 5-(carboxyhydroxylmethyl)uracil, 5-fluorouracil, 5-bromouracil, 5-carboxymethylaminomethyl-2-thiouracil, 5-carboxy-methylaminomethyluracil, dihydrouracil, inosine, N6-iso-pentenyladenine, 1-methyladenine, 1-methylpseudouracil, 1-methylguanine, 1-methylinosine, 2,2-dimethyl-guanine, 2-methyladenine, 2-methylguanine, 3-methylcytosine, 5-methylcytosine, N6-methyladenine, 7-methylguanine, 5-methylaminomethyluracil, 5-methoxyamino-methyl-2-thiouracil, beta-D-mannosylqueosine, 5'-methoxycarbonyl-methyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

The term "naturally occurring" or "native" when used in connection with biological materials such as nucleic acid molecules, polypeptides, host cells, and the like, refers to materials which are found in nature and are not manipulated by man. Similarly, "non-naturally occurring" or "non-native" as used herein refers to a material that is not found in nature or that has been structurally modified or synthesized by man.

The term "operably linked" is used herein to refer to an arrangement of flanking sequences wherein the flanking sequences so described are configured or assembled so as to perform their usual function. Thus, a flanking sequence operably linked to a coding sequence may be capable of effecting the replication, transcription and/or translation of the coding sequence. For example, a coding sequence is operably linked to a promoter when the promoter is capable of directing transcription of that coding sequence. A flanking sequence need not be contiguous with the coding sequence, so long as it functions correctly. Thus, for example, intervening untranslated yet transcribed sequences can be present between a promoter sequence and the coding sequence and the promoter sequence can still be considered "operably linked" to the coding sequence.

The term "pharmaceutically acceptable carrier" or "physiologically acceptable carrier" as used herein refers to one or more formulation materials suitable for accomplishing or enhancing the delivery of a β10 nucleic acid molecule, β10 polypeptide, α2/β10 heterodimer or selective binding agents of the present invention as a pharmaceutical composition.

The term "selective binding agent" refers to a molecule or molecules having specificity for the β10 polypeptide and/or α2/β10 heterodimer of this invention. As used herein, the terms, "specific" and "specificity" refer to the ability of the selective binding agents to bind to human β10 polypeptide and/or α2/β10 heterodimer and not to bind to human non-β10 polypeptide and/or non-α2/β10 heterodimer. It will be appreciated, however, that the selective binding agents may also bind orthologs of the polypeptide set forth in SEQ ID NO: 3, and/or orthologs of human α2/β10 heterodimer, that is, interspecies versions thereof, such as mouse and rat polypeptides.

The term "transduction" is used to refer to the transfer of genes from one bacterium to another, usually by a phage. "Transduction" also refers to the acquisition and transfer of eukaryotic cellular sequences by retroviruses.

The term "transfection" is used to refer to the uptake of foreign or exogenous DNA by a cell, and a cell has been "transfected" when the exogenous DNA has been introduced inside the cell membrane. A number of transfection techniques are well known in the art and are disclosed herein. See, for example, Graham et al., *Virology*, 52:456 (1973); Sambrook et al., *Molecular Cloning, a laboratory Manual*, Cold Spring Harbor Laboratories (New York, 1989); Davis et al., *Basic Methods in Molecular Biology*, Elsevier, 1986; and Chu et al., *Gene*, 13:197 (1981). Such techniques can be used to introduce one or more exogenous DNA moieties into suitable host cells.

The term "transformation" as used herein refers to a change in a cell's genetic characteristics, and a cell has been transformed when it has been modified to contain a new DNA. For example, a cell is transformed where it is genetically modified from its native state. Following transfection or transduction, the transforming DNA may recombine with that of the cell by physically integrating into a chromosome of the cell, may be maintained transiently as an episomal element without being replicated, or may replicate independently as a plasmid. A cell is considered to have been stably transformed when the DNA is replicated with the division of the cell.

The term "vector" is used to refer to any molecule (e.g., nucleic acid, plasmid, or virus) used to transfer coding information to a host cell.

Relatedness of Nucleic Acid Molecules and/or Polypeptides

It is understood that related nucleic acid molecules include allelic or splice variants of the nucleic acid molecule of SEQ ID NO: 2, and include sequences which are complementary to any of the above nucleotide sequences. Related nucleic acid molecules also include a nucleotide sequence encoding a polypeptide comprising or consisting essentially of a substitution, modification, addition and/or a deletion of one or more amino acid residues compared to the polypeptide in SEQ ID NO: 1.

Fragments include nucleic acid molecules which encode a polypeptide of at least about 25 amino acid residues, or about 50, or about 75, or about 100, or greater than about 100 amino acid residues of the polypeptide of SEQ ID NO: 1.

In addition, related β10 nucleic acid molecules include those molecules which comprise nucleotide sequences which hybridize under moderately or highly stringent conditions as defined herein with the fully complementary sequence of the nucleic acid molecule of SEQ ID NO: 2, or of a molecule encoding a polypeptide, which polypeptide comprises the amino acid sequence of SEQ ID NO: 1, or of a nucleic acid fragment as defined herein, or of a nucleic acid fragment encoding a polypeptide as defined herein. Hybridization probes may be prepared using the β10 sequences provided herein to screen cDNA, genomic or synthetic DNA libraries for related sequences. Regions of the DNA and/or amino acid sequence of the β10 polypeptide that exhibit significant identity to known sequences are readily determined using sequence alignment algorithms as described herein and those regions may be used to design probes for screening.

The term "highly stringent conditions" refers to those conditions that are designed to permit hybridization of DNA strands whose sequences are highly complementary, and to exclude hybridization of significantly mismatched DNAs. Hybridization stringency is principally determined by temperature, ionic strength, and the concentration of denaturing agents such as formamide. Examples of "highly stringent conditions" for hybridization and washing are 0.015M sodium chloride, 0.0015M sodium citrate at 65-68° C. or 0.015M sodium chloride, 0.0015M sodium citrate, and 50% formamide at 42° C. See Sambrook, Fritsch & Maniatis, Molecular Cloning: A Laboratory Manual, 2$^{nd}$ Ed., Cold Spring Harbor Laboratory, (Cold Spring Harbor, N.Y. 1989); Anderson et al., Nucleic Acid Hybridisation: a practical approach, Ch. 4, IRL Press Limited (Oxford, England).

More stringent conditions (such as higher temperature, lower ionic strength, higher formamide, or other denaturing agent) may also be used, however, the rate of hybridization will be affected. Other agents may be included in the hybridization and washing buffers for the purpose of reducing non-specific and/or background hybridization. Examples are 0.1% bovine serum albumin, 0.1% polyvinyl-pyrrolidone, 0.1% sodium pyrophosphate, 0.1% sodium dodecylsulfate (NaDodSO$_4$ or SDS), ficoll, Denhardt's solution, sonicated salmon sperm DNA (or other non-complementary DNA), and dextran sulfate, although other suitable agents can also be used. The concentration and types of these additives can be changed without substantially affecting the stringency of the hybridization conditions. Hybridization experiments are usually carried out at pH 6.8-7.4, however, at typical ionic strength conditions, the rate of hybridization is nearly independent of pH. See Anderson et al., Nucleic Acid Hybridisation: a Practical Approach, Ch. 4, IRL Press Limited (Oxford, England).

Factors affecting the stability of a DNA duplex include base composition, length, and degree of base pair mismatch. Hybridization conditions can be adjusted by one skilled in the art in order to accommodate these variables and allow DNAs of different sequence relatedness to form hybrids. The melting temperature of a perfectly matched DNA duplex can be estimated by the following equation:

$$T_m(° C.)=81.5+16.6(\log [Na+])+0.41(\% G+C)-600/N-0.72(\% \text{ formamide})$$

where N is the length of the duplex formed, [Na+] is the molar concentration of the sodium ion in the hybridization or washing solution, % G+C is the percentage of (guanine+cytosine) bases in the hybrid. For imperfectly matched hybrids, the melting temperature is reduced by approximately 1° C. for each 1% mismatch.

The term "moderately stringent conditions" refers to conditions under which a DNA duplex with a greater degree of base pair mismatching than could occur under "highly stringent conditions" is able to form. Examples of typical "moderately stringent conditions" are 0.015M sodium chloride, 0.0015M sodium citrate at 50-65° C. or 0.015M sodium chloride, 0.0015M sodium citrate, and 20% formamide at 37-50° C. By way of example, a "moderately stringent" condition of 50° C. in 0.015 M sodium ion will allow about a 21% mismatch.

It will be appreciated by those skilled in the art that there is no absolute distinction between "highly" and "moderately" stringent conditions. For example, at 0.015M sodium ion (no formamide), the melting temperature of perfectly matched long DNA is about 71° C. With a wash at 65° C. (at the same ionic strength), this would allow for approximately a 6% mismatch. To capture more distantly related sequences, one skilled in the art can simply lower the temperature or raise the ionic strength.

A good estimate of the melting temperature in 1M NaCl* for oligonucleotide probes up to about 20 nucleotides is given by:

$$Tm=2° C. \text{ per } A-T \text{ base pair}+4° C. \text{ per } G-C \text{ base pair}$$

*The sodium ion concentration in 6× salt sodium citrate (SSC) is 1M. See Suggs et al., Developmental Biology Using Purified Genes, p. 683, Brown and Fox (eds.) (1981).

High stringency washing conditions for oligonucleotides are usually at a temperature of 0-5° C. below the Tm of the oligonucleotide in 6×SSC, 0.1% SDS.

In another embodiment, related nucleic acid molecules comprise or consist of a nucleotide sequence that is about 70 percent identical to the nucleotide sequence of SEQ ID NO: 2, or comprise or consist essentially of a nucleotide sequence encoding a polypeptide that is about 70 percent identical to the polypeptide of SEQ ID NO: 1. In preferred embodiments, the nucleotide sequences are about 70 percent, 75 percent, 80 percent, or about 85 percent, or about 90 percent, or about 95, 96, 97, 98, or 99 percent identical to the nucleotide sequence as shown in SEQ ID NO: 2, or the nucleotide sequences encode a polypeptide that is about 70 percent, 75 percent, 80 percent, or about 85 percent, or about 90 percent, or about 95, 96, 97, 98, or 99 percent identical to the polypeptide sequence as set forth in SEQ ID NO: 1.

Differences in the nucleic acid sequence may result in conservative and/or non-conservative modifications of the amino acid sequence relative to the amino acid sequence of SEQ ID NO: 1.

Conservative modifications to the amino acid sequence of SEQ ID NO: 1 (and the corresponding modifications to the encoding nucleotides) will produce β10-like polypeptides in accordance with this invention having functional and chemical characteristics similar to those of the naturally occurring β10 polypeptide hereof. In contrast, substantial modifications in the functional and/or chemical characteristics of the β10 polypeptide may be accomplished by selecting substitutions in the amino acid sequence of SEQ ID NO: 1 that differ significantly in their effect on maintaining (a) the structure of the molecular backbone in the area of the substitution, for example, as a sheet or helical conformation, (b) the charge or hydrophobicity of the molecule at the target site, or (c) the bulk of the side chain.

For example, a "conservative amino acid substitution" may involve a substitution of a native amino acid residue with a nonnative residue such that there is little or no effect on the polarity or charge of the amino acid residue at that position. Furthermore, any native residue in the polypeptide may also be substituted with alanine, as has been previously described for "alanine scanning mutagenesis."

Conservative amino acid substitutions also encompass non-naturally occurring amino acid residues which are typically incorporated by chemical peptide synthesis rather than by synthesis in biological systems. These include peptidomimetics, and other reversed or inverted forms of amino acid moieties.

Naturally occurring residues may be divided into classes based on common side chain properties:
1) hydrophobic: norleucine, Met, Ala, Val, Leu, Ile;
2) neutral hydrophilic: Cys, Ser, Thr, Asn, Gln;
3) acidic: Asp, Glu;
4) basic: His, Lys, Arg;
5) residues that influence chain orientation: Gly, Pro; and
6) aromatic: Trp, Tyr, Phe.

For example, non-conservative substitutions may involve the exchange of a member of one of these classes for a member from another class. Such substituted residues may be introduced into regions of the human β10 polypeptide that are homologous with non-human β10 polypeptide orthologs, or into the non-homologous regions of the molecule.

In making such changes, the hydropathic index of amino acids may be considered. Each amino acid has been assigned a hydropathic index on the basis of their hydrophobicity and charge characteristics, these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is understood in the art. Kyte et al., *J. Mol. Biol.*, 157:105-131 (1982). It is known that certain amino acids may be substituted for other amino acids having a similar hydropathic index or score and still retain a similar biological activity. In making changes based upon the hydropathic index, the substitution of amino acids whose hydropathic indices are within ±2 is preferred, those which are within ±1 are particularly preferred, and those within ±0.5 are even more particularly preferred.

It is also understood in the art that the substitution of like amino acids can be made effectively on the basis of hydrophilicity, particularly where the biologically functionally equivalent protein or peptide thereby created is intended for use in immunological embodiments, as in the present case. The greatest local average hydrophilicity of a protein, as governed by the hydrophilicity of its adjacent amino acids, correlates with its immunogenicity and antigenicity, i.e., with a biological property of the protein.

The following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0);

methionine (−1.3); valine (−1.5); leucine (−1.8); isoleucine (−1.8); tyrosine (−2.3); phenylalanine (−2.5); tryptophan (−3.4). In making changes based upon similar hydrophilicity values, the substitution of amino acids whose hydrophilicity values are within ±2 is preferred, those which are within ±1 are particularly preferred, and those within ±0.5 are even more particularly preferred. One may also identify epitopes from primary amino acid sequences on the basis of hydrophilicity. These regions are also referred to as "epitopic core regions."

Desired amino acid substitutions (whether conservative or non-conservative) can be determined by those skilled in the art at the time such substitutions are desired. For example, amino acid substitutions can be used to identify important residues of the β10 polypeptide or to increase or decrease the affinity of the β10 polypeptides or the α2/β10 heterodimers described herein.

Exemplary amino acid substitutions are set forth in Table I.

TABLE I

Amino Acid Substitutions

| Original Residues | Exemplary Substitutions | Preferred Substitutions |
| --- | --- | --- |
| Ala | Val, Leu, Ile | Val |
| Arg | Lys, Gln, Asn | Lys |
| Asn | Gln | Gln |
| Asp | Glu | Glu |
| Cys | Ser, Ala | Ser |
| Gln | Asn | Asn |
| Glu | Asp | Asp |
| Gly | Pro, Ala | Ala |
| His | Asn, Gln, Lys, Arg | Arg |
| Ile | Leu, Val, Met, Ala, Phe, Norleucine | Leu |
| Leu | Norleucine, Ile, Val, Met, Ala, Phe | Ile |
| Lys | Arg, 1,4 Diaminobutyric Acid, Gln, Asn | Arg |
| Met | Leu, Phe, Ile | Leu |
| Phe | Leu, Val, Ile, Ala, Tyr | Leu |
| Pro | Ala | Gly |
| Ser | Thr, Ala, Cys | Thr |
| Thr | Ser | Ser |
| Trp | Tyr, Phe | Tyr |
| Tyr | Trp, Phe, Thr, Ser | Phe |
| Val | Ile, Met, Leu, Phe, Ala, Norleucine | Leu |

A skilled artisan will be able to determine suitable variants of the polypeptides of SEQ ID NOs: 1 or 3 using well known techniques. For identifying suitable areas of the molecule that may be changed without destroying activity, one skilled in the art may target areas not believed to be important for activity. For example, when similar polypeptides with similar activities from the same species or from other species are known, one skilled in the art may compare the amino acid sequence of a β10 polypeptide to such similar polypeptides. With such a comparison, one can identify residues and portions of the molecules that are conserved among similar polypeptides. It will be appreciated that changes in areas of a β10 polypeptide that are not conserved relative to such similar polypeptides would be less likely to adversely affect the biological activity and/or structure of the β10 polypeptide or the α2/β10 heterodimer. One skilled in the art would also know that, even in relatively conserved regions, one may substitute chemically similar amino acids for the naturally occurring residues while retaining activity (conservative amino acid residue substitutions). Therefore, even areas that may be important for biological activity or for structure may be subject to conservative amino acid substitutions without destroying the biological activity or without adversely affecting the polypeptide structure.

Additionally, one skilled in the art can review structure-function studies identifying residues in similar polypeptides that are important for activity or structure. In view of such a comparison, one can predict the importance of amino acid residues in a β10 polypeptide that correspond to amino acid residues that are important for activity or structure in similar polypeptides. One skilled in the art may opt for chemically similar amino acid substitutions for such predicted important amino acid residues of the β10 polypeptide.

One skilled in the art can also analyze the three-dimensional structure and amino acid sequence in relation to that structure in similar polypeptides. In view of that information, one skilled in the art may predict the alignment of amino acid residues of a β10 polypeptide with respect to its three dimensional structure. One skilled in the art may choose not to make radical changes to amino acid residues predicted to be on the surface of the protein, since such residues may be involved in important interactions with other molecules. Moreover, one skilled in the art may generate test variants containing a single amino acid substitution at each desired amino acid residue. The variants can then be screened using activity assays know to those skilled in the art. Such variants could be used to gather information about suitable variants. For example, if one discovered that a change to a particular amino acid residue resulted in destroyed, undesirably reduced, or unsuitable activity, variants with such a change would be avoided. In other words, based on information gathered from such routine experiments, one skilled in the art can readily determine the amino acids where further substitutions should be avoided either alone or in combination with other mutations.

A number of scientific publications have been devoted to the prediction of secondary structure. See Moult J., *Curr. Op. in Biotech.*, 7(4):422-427 (1996), Chou et al., *Biochemistry*, 13(2):222-245 (1974); Chou et al., *Biochemistry*, 113(2):211-222 (1974); Chou et al., *Adv. Enzymol. Relat. Areas Mol. Biol.*, 47:45-148 (1978); Chou et al., *Ann. Rev. Biochem.*, 47:251-276 and Chou et al., *Biophys. J.*, 26:367-384 (1979). Moreover, computer programs are currently available to assist with predicting secondary structure. One method of predicting secondary structure is based upon homology modeling. For example, two polypeptides or proteins which have a sequence identity of greater than 30%, or similarity greater than 40% often have similar structural topologies. The recent growth of the protein structural data base (PDB) has provided enhanced predictability of secondary structure, including the potential number of folds within a polypeptide's or protein's structure. See Holm et al., *Nucl. Acid. Res.*, 27(1):244-247 (1999). It has been suggested (Brenner et al., *Curr. Op. Struct. Biol.*, 7(3):369-376 (1997)) that there are a limited number of folds in a given polypeptide or protein and that once a critical number of structures have been resolved, structural prediction will gain dramatically in accuracy.

Additional methods of predicting secondary structure include "threading" (Jones, D., *Curr. Opin. Struct. Biol.*, 7(3): 377-87 (1997); Sippl et al., *Structure*, 4(1):15-9 (1996)), "profile analysis" (Bowie et al., *Science*, 253:164-170 (1991); Gribskov et al., *Meth. Enzym.*, 183:146-159 (1990); Gribskov et al., *Proc. Nat. Acad. Sci.*, 84(13):4355-4358 (1987)), and "evolutionary linkage" (See Home, supra, and Brenner, supra).

Preferred β10 polypeptide or α2/β10 heterodimer variants in accordance with this invention include glycosylation variants wherein the number and/or type of glycosylation sites has been altered compared to the amino acid sequence set forth in SEQ ID NO: 1. In one embodiment, β10 polypeptide or α2/β10 heterodimer variants according to this invention comprise a greater or a lesser number of N-linked glycosylation sites than the amino acid sequence set forth in SEQ ID NO: 1. An N-linked glycosylation site is characterized by the sequence: Asn-X-Ser or Asn-X-Thr, wherein the amino acid residue designated as X may be any amino acid residue except proline. The substitution(s) of amino acid residues to create this sequence provides a potential new site for the addition of an N-linked carbohydrate chain. Alternatively, substitutions which eliminate this sequence will remove an existing N-linked carbohydrate chain. Also provided is a rearrangement of N-linked carbohydrate chains wherein one or more N-linked glycosylation sites (typically those that are naturally occurring) are eliminated and one or more new N-linked sites are created. Additional preferred β10 polypeptide or α2/β10 heterodimer variants include cysteine variants, wherein one or more cysteine residues are deleted from or substituted for another amino acid (e.g., serine) as compared to the amino acid sequence set forth in SEQ ID NO: 1. Cysteine variants are useful when the β10 polypeptide or α2/β10 heterodimer must be refolded into a biologically active conformation such as after the isolation of insoluble inclusion bodies. Cysteine variants generally have fewer cysteine residues than the native protein, and typically have an even number to minimize interactions resulting from unpaired cysteines.

In addition, the polypeptide comprising the amino acid sequence of SEQ ID NO: 3 or a polypeptide variant thereof may be fused to a heterologous polypeptide, such as but not limited to α2, to form a heterodimer. Heterologous peptides and polypeptides include, but are not limited to: an epitope to allow for the detection and/or isolation of a β10 fusion polypeptide or an α2/β10 heterodimer; a transmembrane receptor protein or a portion thereof, such as an extracellular domain, or a transmembrane and intracellular domain; a ligand or a portion thereof which binds to a transmembrane receptor protein; an enzyme or portion thereof which is catalytically active; a polypeptide or peptide which promotes oligomerization, such as a leucine zipper domain; a polypeptide with which β10 normally dimerizes, such as α2; a polypeptide or peptide which increases stability, such as an immunoglobulin constant region; and a polypeptide which has a therapeutic activity different from the polypeptide comprising the amino acid sequence set forth in SEQ ID NO: 3 or a polypeptide variant thereof.

Fusions can be made either at the amino terminus or at the carboxy terminus of the polypeptide comprising the amino acid sequence set forth in SEQ ID NO: 3 or a polypeptide variant. Fusions may be direct with no linker or adapter molecule or indirect using a linker or adapter molecule. A linker or adapter molecule may be one or more amino acid residues, typically up to about 20 to about 50 amino acid residues. A linker or adapter molecule may also be designed with a cleavage site for a DNA restriction endonuclease or for a protease to allow for the separation of the fused moieties. It will be appreciated that once constructed, the fusion polypeptides can be derivatized according to the methods described herein.

In a further embodiment of the invention, the polypeptide comprising the amino acid sequence of SEQ ID NO: 3 or a polypeptide variant is fused to one or more domains of an Fc region of human IgG. Antibodies comprise two functionally independent parts, a variable domain known as "Fab", which binds antigen, and a constant domain known as "Fc", which is involved in effector functions such as complement activation and attack by phagocytic cells. An Fc has a long serum half-life, whereas an Fab is short-lived. Capon et al., *Nature*, 337:525-31 (1989). When constructed together with a therapeutic protein, an Fc domain can provide longer half-life or incorporate such functions as Fc receptor binding, protein A binding, complement fixation and perhaps even placental transfer. Id. Table II summarizes the use of certain Fc fusions known in the art.

TABLE II

Fc Fusion with Therapeutic Proteins

| Form of Fc | Fusion partner | Therapeutic implications | Reference |
|---|---|---|---|
| IgG1 | N-terminus of CD30-L | Hodgkin's disease; anaplastic lymphoma; T-cell leukemia | U.S. Pat. No. 5,480,981 |
| Murine Fcγ2a | IL-10 | anti-inflammatory; transplant rejection | Zheng et al. (1995), J. Immunol., 154: 5590-5600 |
| IgG1 | TNF receptor | septic shock | Fisher et al. (1996), N. Engl. J. Med., 334: 1697-1702; Van Zee et al., (1996), J. Immunol., 156: 2221-2230 |
| IgG, IgA, IgM, or IgE (excluding the first domain) | TNF receptor | inflammation, autoimmune disorders | U.S. Pat. No. 5,808,029, issued Sep. 15, 1998 |
| IgG1 | CD4 receptor | AIDS | Capon et al. (1989), Nature 337: 525-531 |
| IgG1, IgG3 | N-terminus of IL-2 | anti-cancer, antiviral | Harvill et al. (1995), Immunotech., 1: 95-105 |
| IgG1 | C-terminus of OPG | osteoarthritis; bone density | WO 97/23614, published Jul. 3, 1997 |
| IgG1 | N-terminus of leptin | anti-obesity | PCT/US 97/23183, filed Dec. 11, 1997 |
| Human Ig Cγ1 | CTLA-4 | autoimmune disorders | Linsley (1991), J. Exp. Med., 174: 561-569 |

In one example, all or a portion of the human IgG hinge, CH2 and CH3 regions may be fused at either the N-terminus or C-terminus of a β10 polypeptide of this invention using methods known to the skilled artisan. The resulting β10-fusion polypeptide or α2/β10-fusion polypeptide may be purified by use of a Protein A affinity column. Peptides and proteins fused to an Fc region have been found to exhibit a substantially greater half-life in vivo than the unfused counterpart. Also, a fusion to an Fc region allows for dimerization/multimerization of the fusion polypeptide. The Fc region may be a naturally occurring Fc region, or may be altered to improve certain qualities, such as therapeutic qualities, circulation time, reduce aggregation, etc.

Identity and similarity of related nucleic acid molecules and polypeptides can be readily calculated by known methods. Such methods include, but are not limited to, those described in Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; Sequence Analysis Primer, Gribskov, M. and Devereux, J., eds., M. Stockton Press, New York, 1991; and Carillo et al., *SIAM J. Applied Math.*, 48:1073 (1988).

Preferred methods to determine identity and/or similarity are designed to give the largest match between the sequences tested. Methods to determine identity and similarity are described in publicly available computer programs. Preferred computer program methods to determine identity and similarity between two sequences include, but are not limited to, the GCG program package, including GAP (Devereux et al., *Nucl. Acid. Res.*, 12:387 (1984); Genetics Computer Group, University of Wisconsin, Madison, Wis.), BLASTP, BLASTN, and FASTA (Altschul et al., *J. Mol. Biol.*, 215:403-410 (1990)). The BLASTX program is publicly available from the National Center for Biotechnology Information (NCBI) and other sources (*BLAST Manual*, Altschul et al. NCB/NLM/NIH Bethesda, Md. 20894; Altschul et al., supra). The well known Smith Waterman algorithm may also be used to determine identity.

Certain alignment schemes for aligning two amino acid sequences may result in the matching of only a short region of the two sequences, and this small aligned region may have very high sequence identity even though there is no significant relationship between the two full length sequences. Accordingly, in a preferred embodiment, the selected alignment method (GAP program) will result in an alignment that spans at least fifty (50) contiguous amino acids of the target polypeptide.

For example, using the computer algorithm GAP (Genetics Computer Group, University of Wisconsin, Madison, Wis.), two polypeptides for which the percent sequence identity is to be determined are aligned for optimal matching of their respective amino acids (the "matched span", as determined by the algorithm). A gap opening penalty (which is calculated as 3× the average diagonal; the "average diagonal" is the average of the diagonal of the comparison matrix being used; the "diagonal" is the score or number assigned to each perfect amino acid match by the particular comparison matrix) and a gap extension penalty (which is usually $\frac{1}{10}$ times the gap opening penalty), as well as a comparison matrix such as PAM 250 or BLOSUM 62 are used in conjunction with the algorithm. A standard comparison matrix (see Dayhoff et al., Atlas of Protein Sequence and Structure, vol. 5, supp.3 (1978) for the PAM 250 comparison matrix; Henikoff et al., *Proc. Natl. Acad. Sci* USA, 89:10915-10919 (1992) for the BLOSUM 62 comparison matrix) is also used by the algorithm.

Preferred parameters for a polypeptide sequence comparison include the following:

Algorithm: Needleman et al., *J. Mol. Biol.*, 48:443-453 (1970);

Comparison matrix: BLOSUM 62 from Henikoff et al., *Proc. Natl. Acad. Sci.* USA, 89:10915-10919 (1992);

Gap Penalty: 12

Gap Length Penalty: 4

Threshold of Similarity: 0

The GAP program is useful with the above parameters. The aforementioned parameters are the default parameters for polypeptide comparisons (along with no penalty for end gaps) using the GAP algorithm.

Preferred parameters for nucleic acid molecule sequence comparisons include the following:

Algorithm: Needleman et al., *J. Mol Biol.*, 48:443-453 (1970);

Comparison matrix: matches=+10, mismatch=0

Gap Penalty: 50

Gap Length Penalty: 3

The GAP program is also useful with the above parameters. The aforementioned parameters are the default parameters for nucleic acid molecule comparisons.

Other exemplary algorithms, gap opening penalties, gap extension penalties, comparison matrices, thresholds of similarity, etc. may be used, including those set forth in the Program Manual, Wisconsin Package, Version 9, September, 1997. The particular choices to be made will be apparent to those of skill in the art and will depend on the specific comparison to be made, such as DNA to DNA, protein to protein, protein to DNA; and additionally, whether the comparison is between given pairs of sequences (in which case GAP or BestFit are generally preferred) or between one sequence and a large database of sequences (in which case FASTA or BLASTA are preferred).

Synthesis

It will be appreciated by those skilled in the art the nucleic acid and polypeptide molecules described herein may be produced by recombinant and other means.

Nucleic Acid Molecules

The nucleic acid molecules encode a polypeptide comprising the amino acid sequence of a β10 polypeptide of this invention can readily be obtained in a variety of ways including, without limitation, chemical synthesis, cDNA or genomic library screening, expression library screening and/ or PCR amplification of cDNA.

Recombinant DNA methods used herein are generally those set forth in Sambrook et al., *Molecular Cloning: A Laboratory Manual*, Cold Spring Harbor Laboratory Press, Cold Spring Harbor, N.Y. (1989), and/or Ausubel et al., eds., *Current Protocols in Molecular Biology*, Green Publishers Inc. and Wiley and Sons, NY (1994). The present invention provides for nucleic acid molecules as described herein and methods for obtaining the molecules.

Where a gene encoding the amino acid sequence of a β10 polypeptide has been identified from one species, all or a portion of that gene may be used as a probe to identify orthologs or related genes from the same species. The probes or primers may be used to screen cDNA libraries from various tissue sources believed to express the β10 polypeptide. In addition, part or all of a nucleic acid molecule having the sequence set forth in SEQ ID NO: 2 may be used to screen a genomic library to identify and isolate a gene encoding the amino acid sequence of a β10 polypeptide. Typically, conditions of moderate or high stringency will be employed for screening to minimize the number of false positives obtained from the screen.

Nucleic acid molecules encoding the amino acid sequence of a β10 polypeptide may also be identified by expression cloning which employs the detection of positive clones based upon a property of the expressed protein. Typically, nucleic acid libraries are screened by the binding of an antibody or other binding partner (e.g., receptor or ligand) to cloned proteins which are expressed and displayed on a host cell surface. The antibody or binding partner is modified with a detectable label to identify those cells expressing the desired clone.

Recombinant expression techniques conducted in accordance with the descriptions set forth below may be followed to produce these polynucleotides and to express the encoded polypeptides. For example, by inserting a nucleic acid sequence which encodes the amino acid sequence of a β10 polypeptide into an appropriate vector, one skilled in the art can readily produce large quantities of the desired nucleotide sequence. The sequences can then be used to generate detection probes or amplification primers. Alternatively, a polynucleotide encoding the amino acid sequence of a β10 polypeptide can be inserted into an expression vector. By introducing the expression vector into an appropriate host, the encoded β10 polypeptide may be produced in large amounts.

Another method for obtaining a suitable nucleic acid sequence is the polymerase chain reaction (PCR). In this method, cDNA is prepared from poly(A)+RNA or total RNA using the enzyme reverse transcriptase. Two primers, typically complementary to two separate regions of cDNA (oligonucleotides) encoding the amino acid sequence of a β10 polypeptide, are then added to the cDNA along with a polymerase such as Tag-polymerase, and the polymerase amplifies the cDNA region between the two primers.

Another means of preparing a nucleic acid molecule encoding the amino acid sequence of a β10 polypeptide is chemical synthesis using methods well known to the skilled artisan such as those described by Engels et al., *Angew. Chem. Intl. Ed.*, 28:716-734 (1989). These methods include, inter alia, the phosphotriester, phosphoramidite, and H-phosphonate methods for nucleic acid synthesis. A preferred method for such chemical synthesis is polymer-supported synthesis using standard phosphoramidite chemistry. Typically, the DNA encoding the amino acid sequence of a β10 polypeptide will be several hundred nucleotides in length. Nucleic acids larger than about 100 nucleotides can be synthesized as several fragments using these methods. The fragments can then be ligated together to form the full length nucleotide sequence of a β10 polypeptide. Usually, the DNA fragment encoding the amino terminus of the polypeptide will have an ATG, which encodes a methionine residue. This methionine may or may not be present on the mature form of the β10 polypeptide, depending on whether the polypeptide produced in the host cell is designed to be secreted from that cell. Other methods known to the skilled artisan may be used as well.

In certain embodiments, nucleic acid variants contain codons which have been altered for the optimal expression of β10 polypeptide or α2/β10 heterodimer in a given host cell. Particular codon alterations will depend upon the β10 polypeptide(s) and host cell(s) selected for expression. Such "codon optimization" can be carried out by a variety of methods, for example, by selecting codons which are preferred for use in highly expressed genes in a given host cell. Computer algorithms which incorporate codon frequency tables such as "Ecohigh.cod" for codon preference of highly expressed bacterial genes may be used and are provided by the University of Wisconsin Package Version 9.0, Genetics Computer Group, Madison, Wis. Other useful codon frequency tables include "C elegans_high.cod", "C elegans_low.cod", "Drosophila_high.cod", "Human_high.cod", "Maize_high.cod", and "Yeast_high.cod".

Vectors and Host Cells

When contemplating expression of an α2/β10 heterodimer, it should be understood that the β10 polypeptide expression vector as well as an expression vector encoding α2 polypeptide can both be introduced (for example, transformed, co-transformed, transfected, co-transfected, transduced, co-transduced) into a host cell, cell line, tissue, organ, animal or plant. It is also understood that introduction of a β10 polypeptide expression vector alone into a host cell, cell line, tissue, organ, animal or plant that already produces α2 polypeptide can result in de novo or enhanced production of an α2/β10 heterodimer. As described above in the heterodimerization assay recombinant polyHis and FLAG tagged α2/β10 heterodimer was produced by co-transfection of mammalian cells. Heterodimeric glycoprotein hormones such as CG can also be assembled in vitro upon co-incubation of, for example, isolated alpha-subunit and isolated CG-β subunit under suitable conditions [see Blithe and Iles, Endocrinology, volume 136, pages 903-910 (1995)]. α2/β10 heterodimer could similarly be assembled in vitro upon incubation of isolated α2 polypeptide and isolated β10 polypeptide. The result might be a mixture of α2 polypeptide, β10 polypeptide and α2/β10 heterodimer. Each of these products could be isolated in purified form using conventional methods such as size exclusion chromatography and/or immunoaffinity chromatography. In this regard α2 polypeptide alone and β10 polypeptide alone can be separately produced and secreted from mammalian cells as described below. A human α2-polyHis-tag mammalian expression vector was transfected into 293 cells and serum free conditioned media was harvested after 72 hours. Western blot of this conditioned media was probed with affinity purified anti-α2 rabbit polyclonal antibodies (example 4) that had been conjugated to Horse Radish Peroxidase (Linx HRP Rapid Protein Conjugation Kit, cat# K8050-01, Invitrogen Corp., Carlsbad, Calif.). A strong band was observed using the ECL Western Blot detection kit (cat #RPN 2106, Amersham Pharmacia Biotech, Piscataway, N.J.) demonstrating that a human α2 polypeptide could be secreted in the absence of β10 polypeptide. A human β10-FLAG-tag mammalian expression vector was transfected into 293 cells and serum free conditioned media was harvested after 72 hours. Western blot of this conditioned media was probed with a biotinylated anti-FLAG M2 monoclonal antibody (cat# F9291, Sigma, St. Louis, Mo.) and then probed with Streptavidin linked Horse Radish Peroxidase (RPN 1231, Amersham Life Sciences). A strong band was observed using the ECL Western Blot detection kit (cat#RPN 2106, Amersham Pharmacia Biotech, Piscataway, N.J.) demonstrating that a human β10 polypeptide could be secreted in the absence of α2 polypeptide.

A nucleic acid molecule encoding the amino acid sequence of a β10 polypeptide may be inserted into an appropriate expression vector using standard ligation techniques. The vector is typically selected to be functional in the particular host cell employed (i.e., the vector is compatible with the host cell machinery such that amplification of the gene and/or expression of the gene can occur). A nucleic acid molecule encoding the amino acid sequence of a β10 polypeptide according to this invention may be amplified/expressed in prokaryotic, yeast, insect (baculovirus systems), and/or eukaryotic host cells. Selection of the host cell will depend in part on whether the β10 polypeptide or α2/β10 heterodimer is to be post-translationally modified (e.g., glycosylated and/or phosphorylated). If so, yeast, insect, or mammalian host cells are preferable. For a review of expression vectors, see *Meth. Enz.*, v. 185, D. V. Goeddel, ed. Academic Press Inc., San Diego, Calif. (1990).

Typically, expression vectors used in any of the host cells will contain sequences for plasmid maintenance and for cloning and expression of exogenous nucleotide sequences. Such sequences, collectively referred to as "flanking sequences" in certain embodiments will typically include one or more of the following nucleotide sequences: a promoter, one or more enhancer sequences, an origin of replication, a transcriptional termination sequence, a complete intron sequence containing a donor and acceptor splice site, a sequence encoding a leader sequence for polypeptide secretion, a ribosome binding site, a polyadenylation sequence, a polylinker region for inserting the nucleic acid encoding the polypeptide to be expressed, and a selectable marker element. Each of these sequences is discussed below.

Optionally, the vector may contain a "tag"-encoding sequence, i.e., an oligonucleotide molecule located at the 5' or 3' end of the β10 polypeptide coding sequence; the oligonucleotide sequence encodes polyHis (such as hexaHis), or other "tag" such as FLAG, HA (hemaglutinin Influenza virus) or myc for which commercially available antibodies exist. This tag is typically fused to the polypeptide upon expression of the polypeptide, and can serve as a means for affinity purification of the β10 polypeptide or α2/β10 heterodimer from the host cell. Affinity purification can be accomplished, for example, by column chromatography using antibodies against the tag as an affinity matrix. Optionally, the tag can subsequently be removed from the purified β10 polypeptide or α2/β10 heterodimer by various means such as using certain peptidases for cleavage.

Flanking sequences may be homologous (i.e., from the same species and/or strain as the host cell), heterologous (i.e., from a species other than the host cell species or strain), hybrid (i.e., a combination of flanking sequences from more than one source) or synthetic, or the flanking sequences may be native sequences which normally function to regulate β10 polypeptide expression. As such, the source of a flanking sequence may be any prokaryotic or eukaryotic organism, any vertebrate or invertebrate organism, or any plant, provided that the flanking sequence is functional in, and can be activated by, the host cell machinery.

The flanking sequences useful in the vectors of this invention may be obtained by any of several methods well known in the art. Typically, flanking sequences useful herein other than the β10 gene flanking sequences will have been previously identified by mapping and/or by restriction endonuclease digestion and can thus be isolated from the proper tissue source using the appropriate restriction endonucleases. In some cases, the full nucleotide sequence of a flanking sequence may be known. Here, the flanking sequence may be synthesized using the methods described herein for nucleic acid synthesis or cloning.

Where all or only a portion of the flanking sequence is known, it may be obtained using PCR and/or by screening a genomic library with suitable oligonucleotide and/or flanking sequence fragments from the same or another species. Where the flanking sequence is not known, a fragment of DNA containing a flanking sequence may be isolated from a larger piece of DNA that may contain, for example, a coding sequence or even another gene or genes. Isolation may be accomplished by restriction endonuclease digestion to produce the proper DNA fragment followed by isolation using agarose gel purification, Qiagen® column chromatography (Chatsworth, Calif.), or other methods known to the skilled artisan. The selection of suitable enzymes to accomplish this purpose will be readily apparent to one of ordinary skill in the art.

An origin of replication is typically a part of those prokaryotic expression vectors purchased commercially, and the origin aids in the amplification of the vector in a host cell. Amplification of the vector to a certain copy number can, in some cases, be important for the optimal expression of β10 polypeptide or α2/β10 heterodimer. If the vector of choice does not contain an origin of replication site, one may be chemically synthesized based on a known sequence, and ligated into the vector. For example, the origin of replication from the plasmid pBR322 (Product No. 303-3s, New England Biolabs, Beverly, Mass.) is suitable for most Gram-negative bacteria and various origins (e.g., SV40, polyoma, adenovirus, vesicular stomatitus virus (VSV) or papillomaviruses such as HPV or BPV) are useful for cloning vectors in mammalian cells. Generally, the origin of replication component is not needed for mammalian expression vectors (for example, the SV40 origin is often used only because it contains the early promoter).

A transcription termination sequence is typically located 3' of the end of a polypeptide coding region and serves to terminate transcription. Usually, a transcription termination sequence in prokaryotic cells is a G–C rich fragment followed by a poly T sequence. While the sequence is easily cloned from a library or even purchased commercially as part of a vector, it can also be readily synthesized using methods for nucleic acid synthesis such as those described herein.

A selectable marker gene element encodes a protein necessary for the survival and growth of a host cell grown in a selective culture medium. Typical selection marker genes encode proteins that (a) confer resistance to antibiotics or other toxins, e.g., ampicillin, tetracycline, or kanamycin for prokaryotic host cells, (b) complement auxotrophic deficiencies of the cell; or (c) supply critical nutrients not available from complex media. Preferred selectable markers are the kanamycin resistance gene, the ampicillin resistance gene, and the tetracycline resistance gene. A neomycin resistance gene may also be used for selection in prokaryotic and eukaryotic host cells.

Other selection genes may be used to amplify the gene which will be expressed. Amplification is the process wherein genes which are in greater demand for the production of a protein critical for growth are reiterated in tandem within the chromosomes of successive generations of recombinant cells. Examples of suitable selectable markers for mammalian cells include dihydrofolate reductase (DHFR) and thymidine kinase. The mammalian cell transformants are placed under selection pressure which only the transformants are uniquely adapted to survive by virtue of the selection gene present in the vector. Selection pressure is imposed by culturing the transformed cells under conditions in which the concentration of selection agent in the medium is successively changed, thereby leading to the amplification of both the selection gene and the DNA that encodes a β10 polypeptide of this invention. As a result, increased quantities of the β10 polypeptide or α2/β10 heterodimer are synthesized from the amplified DNA.

A ribosome binding site is usually necessary for translation initiation of mRNA and is characterized by a Shine-Dalgarno sequence (prokaryotes) or a Kozak sequence (eukaryotes). The element is typically located 3' to the promoter and 5' to the coding sequence of the β10 polypeptide to be expressed. The Shine-Dalgarno sequence is varied but is typically a polypurine (i.e., having a high A-G content). Many Shine-Dalgarno sequences have been identified, each of which can be readily synthesized using methods set forth herein and used in a prokaryotic vector.

A leader, or signal, sequence may be used to direct the β10 polypeptide or α2/β10 heterodimer out of the host cell. Typically, a nucleotide sequence encoding the signal sequence is positioned in the coding region of a β10 nucleic acid molecule, or directly at the 5' end of a β10 polypeptide coding region. Many signal sequences have been identified, and any of those that are functional in the selected host cell may be used in conjunction with a β10 nucleic acid molecule. Therefore, a signal sequence may be homologous (naturally occurring) or heterologous to a β10 gene or cDNA. Additionally, a signal sequence may be chemically synthesized using methods described herein. In most cases, the secretion of a β10 polypeptide or α2/β10 heterodimer from the host cell via the presence of a signal peptide will result in the removal of the signal peptide from the secreted β10 polypeptide or α2/β10 heterodimer. The signal sequence may be a component of the vector, or it may be a part of a β10 nucleic acid molecule that is inserted into the vector.

Included within the scope of this invention is the use of either a nucleotide sequence encoding a native β10 polypeptide signal sequence joined to a β10 polypeptide coding region or a nucleotide sequence encoding a heterologous signal sequence joined to an β10 polypeptide coding region. The heterologous signal sequence selected should be one that is recognized and processed, i.e., cleaved by a signal peptidase, by the host cell. For prokaryotic host cells that do not recognize and process the native β10 polypeptide signal sequence, the signal sequence is substituted by a prokaryotic signal sequence selected, for example, from the group of the alkaline phosphatase, penicillinase, or heat-stable enterotoxin II leaders. For yeast secretion, the native β10 polypeptide signal sequence may be substituted by the yeast invertase, alpha factor, or acid phosphatase leaders. In mammalian cell expression the native signal sequence is satisfactory, although other mammalian signal sequences may be suitable.

In some cases, such as where glycosylation is desired in a eukaryotic host cell expression system, one may manipulate the various presequences to improve glycosylation or yield. For example, one may alter the peptidase cleavage site of a particular signal peptide, or add presequences, which also may affect glycosylation. The final protein product may have, in the −1 position (relative to the first amino acid of the mature protein) one or more additional amino acids incident to expression, which may not have been totally removed. For example, the final protein product may have one or two amino acid residues found in the peptidase cleavage site, attached to the N-terminus. Alternatively, use of some enzyme cleavage sites may result in a slightly truncated form of the desired β10 polypeptide or α2/β10 heterodimer if the enzyme cuts at such area within the mature polypeptide.

In many cases, transcription of a nucleic acid molecule is increased by the presence of one or more introns in the vector; this is particularly true where a polypeptide is produced in eukaryotic host cells, especially mammalian host cells. The introns used may be naturally occurring within the β10 gene, especially where the gene used is a full length genomic sequence or a fragment thereof. Where the intron is not naturally occurring within the gene (as for most cDNAs), the intron(s) may be obtained from another source. The position of the intron with respect to flanking sequences and the β10 gene is generally important, as the intron must be transcribed to be effective. Thus, when a β10 cDNA molecule is being transcribed, the preferred position for the intron is 3' to the transcription start site, and 5' to the polyA transcription termination sequence. Preferably, the intron or introns will be located on one side or the other (i.e., 5' or 3') of the cDNA such that it does not interrupt the coding sequence. Any intron from any source, including any viral, prokaryotic and eukaryotic (plant or animal) organisms, may be used to practice this invention, provided that it is compatible with the host cell(s) into which it is inserted. Also included herein are synthetic introns. Optionally, more than one intron may be used in the vector.

The expression and cloning vectors of the present invention will each typically contain a promoter that is recognized by the host organism and operably linked to the molecule encoding a β10 polypeptide. Promoters are untranscribed sequences located upstream (5') to the start codon of a structural gene (generally within about 100 to 1000 base pairs) that control the transcription of the structural gene. Promoters are conventionally grouped into one of two classes, inducible promoters and constitutive promoters. Inducible promoters initiate increased levels of transcription from DNA under their control in response to some change in culture conditions, such as the presence or absence of a nutrient or a change in temperature. Constitutive promoters, on the other hand, initiate continual gene product production; that is, there is little or no control over gene expression. A large number of promoters, recognized by a variety of potential host cells, are well known. A suitable promoter is operably linked to the DNA encoding a β10 polypeptide by removing the promoter from the source DNA by restriction enzyme digestion and inserting the desired promoter sequence into the vector. The native β10 gene promoter sequence may be used to direct amplification and/or expression of a β10 nucleic acid molecule. A heterologous promoter is preferred, however, if it permits greater transcription and higher yields of the expressed protein as compared to the native promoter, and if it is compatible with the host cell system that has been selected for use.

Promoters suitable for use with prokaryotic hosts include the beta-lactamase and lactose promoter systems; alkaline phosphatase, a tryptophan (trp) promoter system; and hybrid promoters such as the tac promoter. Other known bacterial promoters are also suitable. Their sequences have been published, thereby enabling one skilled in the art to ligate them to the desired DNA sequence(s), using linkers or adapters as needed to supply any useful restriction sites.

Suitable promoters for use with yeast hosts are also well known in the art. Yeast enhancers are advantageously used with yeast promoters. Suitable promoters for use with mammalian host cells are well known and include, but are not limited to, those obtained from the genomes of viruses such as polyoma virus, fowlpox virus, adenovirus (such as Adenovirus 2), bovine papilloma virus, avian sarcoma virus, cytomegalovirus (CMV), a retrovirus, hepatitis-B virus and most preferably Simian Virus 40 (SV40). Other suitable mammalian promoters include heterologous mammalian promoters, e.g., heat-shock promoters and the actin promoter.

Additional promoters which may be of interest in controlling β10 gene transcription include, but are not limited to: the SV40 early promoter region (Bernoist and Chambon, *Nature*, 290:304-310, 1981); the CMV promoter; the promoter contained in the 3' long terminal repeat of Rous sarcoma virus (Yamamoto et al., *Cell*, 22:787-797, 1980); the herpes thymidine kinase promoter (Wagner et al., *Proc. Natl. Acad. Sci. USA*, 78:144-1445, 1981); the regulatory sequences of the metallothionine gene (Brinster et al., *Nature*, 296:39-42, 1982); prokaryotic expression vectors such as the beta-lactamase promoter (Villa-Kamaroff, et al., *Proc. Natl. Acad. Sci. USA*, 75:3727-3731, 1978); or the tac promoter (DeBoer, et al., *Proc. Natl. Acad. Sci. USA*, 80:21-25, 1983). Also of interest are the following animal transcriptional control regions, which exhibit tissue specificity and have been utilized in transgenic animals: the elastase I gene control region which is active in pancreatic acinar cells (Swift et al., *Cell*, 38:639-646, 1984; Ornitz et al., *Cold Spring Harbor Symp. Quant. Biol.*, 50:399-409 (1986); MacDonald, *Hepatology*, 7:425-515, 1987); the insulin gene control region which is active in pancreatic beta cells (Hanahan, *Nature*, 315:115-122, 1985); the immunoglobulin gene control region which is active in lymphoid cells (Grosschedl et al., *Cell*, 38:647-658 (1984); Adames et al., *Nature*, 318:533-538 (1985); Alexander et al., *Mol. Cell. Biol.*, 7:1436-1444, 1987); the mouse mammary tumor virus control region which is active in testicular, breast, lymphoid and mast cells (Leder et al., *Cell*, 45:485-495, 1986); the albumin gene control region which is active in liver (Pinkert et al., *Genes and Devel.*, 1:268-276, 1987); the alphafetoprotein gene control region which is active in liver (Krumlauf et al., *Mol. Cell. Biol.*, 5:1639-1648, 1985; Hammer et al., *Science*, 235:53-58, 1987); the alpha 1-antitrypsin gene control region which is active in the liver (Kelsey et al., *Genes and Devel.*, 1:161-171, 1987); the beta-globin gene control region which is active in myeloid cells (Mogram et al., *Nature*, 315:338-340, 1985; Kollias et al., *Cell*, 46:89-94, 1986); the myelin basic protein gene control region which is active in oligodendrocyte cells in the brain (Readhead et al., *Cell*, 48:703-712, 1987); the myosin light chain-2 gene control region which is active in skeletal muscle (Sani, *Nature*, 314:283-286, 1985); and the gonadotropic releasing hormone gene control region which is active in the hypothalamus (Mason et al., *Science*, 234:1372-1378, 1986).

An enhancer sequence may be inserted into the vector to increase the transcription of a DNA encoding a β10 polypeptide of the present invention by higher eukaryotes. Enhancers are cis-acting elements of DNA, usually about 10-300 by in length, that act on the promoter to increase transcription. Enhancers are relatively orientation and position independent. They have been found 5' and 3' to the transcription unit. Several enhancer sequences available from mammalian genes are known (e.g., globin, elastase, albumin, alpha-fetoprotein and insulin). Typically, however, an enhancer from a virus will be used. The SV40 enhancer, the cytomegalovirus early promoter enhancer, the polyoma enhancer, and adenovirus enhancers are exemplary enhancing elements for the activation of eukaryotic promoters. While an enhancer may be spliced into the vector at a position 5' or 3' to a β10 nucleic acid molecule, it is typically located at a site 5' from the promoter.

Expression vectors of the invention may be constructed from a starting vector such as a commercially available vector. Such vectors may or may not contain all of the desired flanking sequences. Where one or more of the desired flanking sequences are not already present in the vector, they may be individually obtained and ligated into the vector. Methods used for obtaining each of the flanking sequences are well known to one skilled in the art.

Preferred vectors for practicing this invention are those which are compatible with bacterial, insect, and mammalian host cells. Such vectors include, inter alia, pCRII, pCR3, and pcDNA3.1 (Invitrogen Company, Carlsbad, Calif.), pBSII (Stratagene Company, La Jolla, Calif.), pET15 (Novagen, Madison, Wis.), pGEX (Pharmacia Biotech, Piscataway, N.J.), pEGFP-N2 (Clontech, Palo Alto, Calif.), pETL (BlueBacII; Invitrogen), pDSR-alpha (PCT Publication No. WO90/14363) and pFastBacDual (Gibco/BRL, Grand Island, N.Y.).

Additional suitable vectors include, but are not limited to, cosmids, plasmids or modified viruses, but it will be appreciated that the vector system must be compatible with the selected host cell. Such vectors include, but are not limited to plasmids such as Bluescript® plasmid derivatives (a high copy number ColE1-based phagemid, Stratagene Cloning Systems Inc., La Jolla Calif.), PCR cloning plasmids designed for cloning Taq-amplified PCR products (e.g., TOPO™ TA Cloning® Kit, PCR2.1® plasmid derivatives, Invitrogen, Carlsbad, Calif.), and mammalian, yeast, or virus vectors such as a baculovirus expression system (pBacPAK plasmid derivatives, Clontech, Palo Alto, Calif.).

After the vector has been constructed and a nucleic acid molecule encoding a β10 polypeptide has been inserted into the proper site of the vector, the completed vector may be inserted into a suitable host cell for amplification and/or polypeptide expression. The transformation of an expression vector for a β10 polypeptide into a selected host cell may be accomplished by well known methods including methods such as transfection, infection, calcium chloride, electroporation, microinjection, lipofection or the DEAE-dextran method or other known techniques. The method selected will in part be a function of the type of host cell to be used. These methods and other suitable methods are well known to the skilled artisan, and are set forth, for example, in Sambrook et al., supra.

Host cells may be prokaryotic host cells (such as *E. coli*) or eukaryotic host cells (such as a yeast cell, an insect cell or a vertebrate cell). The host cell, when cultured under appropriate conditions, synthesizes a β10 polypeptide or α2/β10 heterodimer which can subsequently be collected from the culture medium (if the host cell secretes it into the medium) or directly from the host cell producing it (if it is not secreted). The selection of an appropriate host cell will depend upon various factors, such as desired expression levels, polypeptide modifications that are desirable or necessary for activity, such as glycosylation or phosphorylation, and ease of folding into a biologically active molecule.

A number of suitable host cells are known in the art and many are available from the American Type Culture Collection (ATCC), 10801 University Boulevard, Manassas, Va. 20110-2209. Examples include, but are not limited to, mammalian cells, such as Chinese hamster ovary cells (CHO) (ATCC No. CCL61) CHO DHFR-cells (Urlaub et al., *Proc. Natl. Acad. Sci. USA*, 97:4216-4220 (1980)), human embryonic kidney (HEK) 293 or 293T cells (ATCC No. CRL1573), or 3T3 cells (ATCC No. CCL92). The selection of suitable mammalian host cells and methods for transformation, culture, amplification, screening and product production and purification are known in the art. Other suitable mammalian cell lines, are the monkey COS-1 (ATCC No. CRL1650) and COS-7 cell lines (ATCC No. CRL1651), and the CV-1 cell line (ATCC No. CCL70). Further exemplary mammalian host cells include primate cell lines and rodent cell lines, including transformed cell lines. Normal diploid cells, cell strains derived from in vitro culture of primary tissue, as well as primary explants, are also suitable. Candidate cells may be genotypically deficient in the selection gene, or may contain a dominantly acting selection gene. Other suitable mammalian cell lines include but are not limited to, mouse neuroblastoma N2A cells, HeLa, mouse L-929 cells, 3T3 lines derived from Swiss, Balb-c or NIH mice, BHK or HaK hamster cell lines, which are available from the ATCC. Each of these cell lines is known by and available to those skilled in the art of protein expression.

Similarly useful as host cells suitable for the present invention are bacterial cells. For example, the various strains of *E. coli* (e.g., HB101, (ATCC No. 33694) DH5α, DH10, and MC1061 (ATCC No. 53338)) are well-known as host cells in the field of biotechnology. Various strains of *B. subtilis*, *Pseudomonas* spp., other *Bacillus* spp., *Streptomyces* spp., and the like may also be employed in this method.

Many strains of yeast cells known to those skilled in the art are also available as host cells for the expression of the β10 polypeptides or α2/β10 heterodimers of the present invention. Preferred yeast cells include, for example, *Saccharomyces cerivisae* and *Pichia pastoris*.

Additionally, where desired, insect cell systems may be utilized in the methods of the present invention. Such systems are described for example in Kitts et al., *Biotechniques*, 14:810-817 (1993); Lucklow, *Curr. Opin. Biotechnol.*, 4:564-572 (1993); and Lucklow et al. (*J. Virol.*, 67:4566-4579 (1993). Preferred insect cells are Sf-9 and Hi5 (Invitrogen, Carlsbad, Calif.).

One may also use transgenic animals to express glycosylated β10 polypeptide or α2/β10 heterodimer. For example, one may use a transgenic milk-producing animal (a cow or goat, for example) and obtain glycosylated β10 polypeptide or α2/β10 heterodimer in the animal milk. One may also use plants to produce β10 polypeptide or α2/β10 heterodimer however, in general, the glycosylation occurring in plants is different from that produced in mammalian cells, and may result in a glycosylated product which is not suitable for human therapeutic use.

Polypeptide Production

Host cells comprising a β10 polypeptide or α2/β10 heterodimer expression vector may be cultured using standard media well known to the skilled artisan. The media will usually contain all nutrients necessary for the growth and survival of the cells. Suitable media for culturing *E. coli* cells include, for example, Luria Broth (LB) and/or Terrific Broth (TB). Suitable media for culturing eukaryotic cells include Roswell Park Memorial Institute medium 1640 (RPMI 1640), Minimal Essential Medium (MEM) and/or Dulbecco's Modified Eagle Medium (DMEM), all of which may be supplemented with serum and/or growth factors as indicated by the particular cell line being cultured. A suitable medium for insect cultures is Grace's medium supplemented with yeastolate, lactalbumin hydrolysate and/or fetal calf serum, as necessary.

Typically, an antibiotic or other compound useful for selective growth of transformed cells is added as a supplement to the media. The compound to be used will be dictated by the selectable marker element present on the plasmid with which the host cell was transformed. For example, where the selectable marker element is kanamycin resistance, the compound added to the culture medium will be kanamycin. Other compounds for selective growth include ampicillin, tetracycline, and neomycin.

The amount of β10 polypeptide or α2/β10 heterodimer produced by a host cell can be evaluated using standard methods known in the art. Such methods include, without limitation, Western blot analysis, SDS-polyacrylamide gel electrophoresis, non-denaturing gel electrophoresis, HPLC separation, immunoprecipitation, and/or activity assays such as DNA binding gel shift assays.

If a β10 polypeptide or α2/β10 heterodimer has been designed to be secreted from the host cells, the majority of β10 polypeptide or α2/β10 heterodimer may be found in the cell culture medium. If however, the β10 polypeptide or α2/β10 heterodimer is not secreted from the host cells, it will be present in the cytoplasm and/or the nucleus (for eukaryotic host cells) or in the cytosol (for bacterial host cells).

For β10 polypeptide or α2/β10 heterodimer situated in the host cell cytoplasm and/or the nucleus (for eukaryotic host cells) or in the cytosol (for bacterial host cells), intracellular material (including inclusion bodies for gram-negative bacteria) can be extracted from the host cell using any standard technique known to the skilled artisan. For example, the host cells can be lysed to release the contents of the periplasm/cytoplasm by French press, homogenization, and/or sonication followed by centrifugation.

If the β10 polypeptide or α2/β10 heterodimer has formed inclusion bodies in the cytosol, the inclusion bodies can often bind to the inner and/or outer cellular membranes and thus will be found primarily in the pellet material after centrifugation. The pellet material can then be treated at pH extremes or with a chaotropic agent such as a detergent, guanidine, guanidine derivatives, urea, or urea derivatives in the presence of a reducing agent such as dithiothreitol at alkaline pH or tris carboxyethyl phosphine at acid pH to release, break apart, and solubilize the inclusion bodies. The β10 polypeptide or α2/β10 heterodimer in its now soluble form can then be analyzed using gel electrophoresis, immuno-precipitation or the like. If it is desired to isolate the β10 polypeptide or α2/β10 heterodimer, isolation may be accomplished using standard methods such as those described herein and in Marston et al., *Meth. Enz.*, 182:264-275 (1990).

In some cases, the β10 polypeptide or α2/β10 heterodimer may not be biologically active upon isolation. Various methods for "refolding" or converting the β10 polypeptide or α2/β10 heterodimer to its tertiary structure and generating disulfide linkages can be used to restore biological activity. Such methods include exposing the solubilized β10 polypeptide or α2/β10 heterodimer to a pH usually above 7 and in the presence of a particular concentration of a chaotrope. The selection of chaotrope is very similar to the choices used for inclusion body solubilization, but usually the chaotrope is used at a lower concentration and is not necessarily the same as chaotropes used for the solubilization. In most cases the refolding/oxidation solution will also contain a reducing agent or the reducing agent plus its oxidized form in a specific ratio to generate a particular redox potential allowing for disulfide shuffling to occur in the formation of the protein's cysteine bridge(s). Some of the commonly used redox couples include cysteine/cystamine, glutathione (GSH)/dithiobis GSH, cupric chloride, dithiothreitol(DTT)/dithiane DTT, and 2-2mercaptoethanol(bME)/dithio-b(ME). A cosolvent may be used to increase the efficiency of the refolding, and the more common reagents used for this purpose include glycerol, polyethylene glycol of various molecular weights, arginine and the like.

If inclusion bodies are not formed to a significant degree upon expression of β10 polypeptide or α2/β10 heterodimer then the β10 polypeptide or α2/β10 heterodimer will be found primarily in the supernatant after centrifugation of the cell homogenate. The β10 polypeptide or α2/β10 heterodimer may be further isolated from the supernatant using methods such as those described herein.

The purification of β10 polypeptide or α2/β10 heterodimer from solution can be accomplished using a variety of techniques. If the β10 polypeptide or α2/β10 heterodimer has been synthesized such that it contains a tag such as Hexahistidine (β10 polypeptide-hexaHis, α2/β10-hexaHis heterodimer) or other small peptide such as FLAG (Eastman Kodak Co., New Haven, Conn.) or myc (Invitrogen, Carlsbad, Calif.) at either its carboxyl or amino terminus, it may be purified in a one-step process by passing the solution through an affinity column where the column matrix has a high affinity for the tag.

For example, polyhistidine binds with great affinity and specificity to nickel, thus an affinity column of nickel (such as the Qiagen® nickel columns) can be used for purification of β10 polypeptide-polyHis or α2/β10-hexaHis heterodimer. See for example, Ausubel et al., eds., *Current Protocols in Molecular Biology*, Section 10.11.8, John Wiley & Sons, New York (1993).

Additionally, the β10 polypeptide or α2/β10 heterodimer may be purified through the use of a monoclonal antibody which is capable of specifically recognizing and binding to the β10 polypeptide or α2/β10 heterodimer.

Suitable procedures for purification thus include, without limitation, affinity chromatography, immunoaffinity chromatography, ion exchange chromatography, molecular sieve chromatography, High Performance Liquid Chromatography (HPLC), electrophoresis (including native gel electrophoresis) followed by gel elution, and preparative isoelectric focusing ("Isoprime" machine/technique, Hoefer Scientific, San Francisco, Calif.). In some cases, two or more purification techniques may be combined to achieve increased purity.

β10 polypeptides or α2/β10 heterodimers may also be prepared by chemical synthesis methods (such as solid phase peptide synthesis) using techniques known in the art, such as those set forth by Merrifield et al., *J. Am. Chem. Soc.*, 85:2149 (1963), Houghten et al., *Proc Natl Acad. Sci. USA*, 82:5132 (1985), and Stewart and Young, Solid Phase Peptide Synthesis, Pierce Chemical Co., Rockford, Ill. (1984). Such β10 polypeptides or α2/β10 heterodimers may be synthesized with or without a methionine on the amino terminus. Chemically synthesized β10 polypeptides or α2/β10 heterodimers may be oxidized using methods set forth in these references to form disulfide bridges. Chemically synthesized β10 polypeptides or α2/β10 heterodimers are expected to have comparable biological activity to the corresponding β10 polypeptides (when heterodimerized to α2) or α2/β10 heterodimers produced recombinantly or purified from natural sources, and thus may be used interchangeably with a recombinant or natural β10 polypeptide or α2/β10 heterodimer.

Another means of obtaining a β10 polypeptide or α2/β10 heterodimer according to this invention is via purification from biological samples such as source tissues and/or fluids in which the β10 polypeptide or α2/β10 heterodimer is naturally found. Such purification can be conducted using methods for protein purification as described herein. The presence of the β10 polypeptide or α2/β10 heterodimer during purification may be monitored using, for example, a corresponding antibody prepared against recombinantly produced β10 polypeptide or peptide fragment thereof, or prepared against recombinantly produced α2/β10 heterodimer or peptide fragment.

A number of additional methods for producing nucleic acids and polypeptides are known in the art, and can be used to produce polypeptides having specificity for β10 polypeptides or α2/β10 heterodimers of this invention. See for example, Roberts, et al., *Proc. Natl. Acad. Sci.*, 94:12297-12303 (1997), which describes the production of fusion proteins between an mRNA and its encoded peptide. See also U.S. Pat. No. 5,824,469, which describes methods of obtaining oligonucleotides capable of carrying out a specific biological function. The procedure involves generating a heterogeneous pool of oligonucleotides, each having a 5' randomized sequence, a central preselected sequence, and a 3' randomized sequence. The resulting heterogeneous pool is introduced into a population of cells that do not exhibit the desired biological function. Subpopulations of the cells are then screened for those which exhibit a predetermined biological function. From that subpopulation, oligonucleotides capable of carrying out the desired biological function are isolated.

U.S. Pat. Nos. 5,763,192, 5,814,476, 5,723,323, and 5,817,483 describe processes for producing peptides or polypeptides. This is done by producing stochastic genes or fragments thereof, and then introducing these genes into host cells which produce one or more proteins encoded by the stochastic genes. The host cells are then screened to identify those clones producing peptides or polypeptides having the desired activity.

Chemical Derivatives

Chemically modified derivatives of the β10 polypeptides or α2/β10 heterodimers of this invention may be prepared by one skilled in the art, given the disclosures set forth hereinbelow. Such β10 polypeptide or α2/β10 heterodimer derivatives are modified in a manner that is different, either in the type or location of the molecules naturally attached to the β10 polypeptide or α2/β10 heterodimer. Derivatives may include molecules formed by the deletion of one or more naturally-attached chemical groups. The polypeptide comprising the amino acid sequence of SEQ ID NO: 3, a β10-like polypeptide variant thereof or a α2/β10 heterodimer may be modified by the covalent attachment of one or more polymers. For example, the polymer selected is typically water soluble so that the protein to which it is attached does not precipitate in an aqueous environment, such as a physiological environment. Included within the scope of suitable polymers is a mixture of polymers. Preferably, for therapeutic use of the end-product preparation, the polymer will be pharmaceutically acceptable.

The polymers each may be of any molecular weight and may be branched or unbranched. The polymers each typically have an average molecular weight of between about 2 kDa to about 100 kDa (the term "about" indicating that in preparations of a water soluble polymer, some molecules will weigh more, some less, than the stated molecular weight). The average molecular weight of each polymer preferably is between about 5 kDa and about 50 kDa, more preferably between about 12 kDa and about 40 kDa and most preferably between about 20 kDa and about 35 kDa.

Suitable water soluble polymers or mixtures thereof include, but are not limited to, N-linked or O-linked carbohydrates, sugars, phosphates, polyethylene glycol (PEG) (including the forms of PEG that have been used to derivatize proteins, including mono-($C_1$-$C_{10}$)alkoxy- or aryloxy-polyethylene glycol), monomethoxy-polyethylene glycol, dextran (such as low molecular weight dextran, of, for example about 6 kD), cellulose, or other carbohydrate based polymers, poly-(N-vinyl pyrrolidone)polyethylene glycol, propylene glycol homopolymers, a polypropylene oxide/ethylene oxide co-polymer, polyoxyethylated polyols (e.g., glycerol) and polyvinyl alcohol. Also encompassed by the present invention are bifunctional crosslinking molecules which may be used to prepare covalently attached multimers of the polypeptide comprising the amino acid sequence of SEQ ID NO: 3, a polypeptide variant thereof or a α2/β10 heterodimer.

In general, chemical derivatization may be performed under any suitable condition used to react a protein with an activated polymer molecule. Methods for preparing chemical derivatives of polypeptides or heterodimers will generally comprise the steps of (a) reacting the polypeptide or heterodimer with the activated polymer molecule (such as a reactive ester or aldehyde derivative of the polymer molecule) under conditions whereby the polypeptide comprising the amino acid sequence of SEQ ID NO: 3, or a polypeptide variant thereof or an α2/β10 heterodimer becomes attached to one or more polymer molecules, and (b) obtaining the reaction product(s). The optimal reaction conditions will be determined based on known parameters and the desired result. For example, the larger the ratio of polymer molecules:protein, the greater the percentage of attached polymer molecule. In one embodiment, the β10 polypeptide or α2/β10 heterodimer derivative may have a single polymer molecule moiety at the amino terminus. See, for example, U.S. Pat. No. 5,234,784.

The pegylation of the polypeptide or heterodimer specifically may be carried out by any of the pegylation reactions known in the art, as described for example in the following references: Francis et al., *Focus on Growth Factors*, 3:4-10 (1992); EP 0154316; EP 0401384 and U.S. Pat. No. 4,179,337. For example, pegylation may be carried out via an acylation reaction or an alkylation reaction with a reactive polyethylene glycol molecule (or an analogous reactive water-soluble polymer) as described herein. For the acylation reactions, the polymer(s) selected should have a single reactive ester group. For reductive alkylation, the polymer(s) selected should have a single reactive aldehyde group. A reactive aldehyde is, for example, polyethylene glycol propionaldehyde, which is water stable, or mono $C_1$-$C_{10}$ alkoxy or aryloxy derivatives thereof (see U.S. Pat. No. 5,252,714).

In another embodiment, a β10 polypeptide or α2/β10 heterodimer may be chemically coupled to biotin, and the biotin-β10 polypeptide or biotin-α2/β10 heterodimer molecules which are conjugated are then allowed to bind to avidin, resulting in tetravalent avidin/biotin/β10 polypeptide molecules or avidin/biotin/α2/β10 heterodimer molecules. β10 polypeptides or α2/β10 heterodimers may also be covalently coupled to dinitrophenol (DNP) or trinitrophenol (TNP) and the resulting conjugates precipitated with anti-DNP or anti-TNP-IgM to form decameric conjugates with a valency of 10.

Generally, conditions which may be alleviated or modulated by the administration of the present β10 polypeptide or α2/β10 heterodimer derivatives include those described herein for β10 polypeptides or α2/β10 heterodimers. However, the β10 polypeptide or α2/β10 heterodimer derivatives disclosed herein may have additional activities, enhanced or reduced biological activity, or other characteristics, such as increased or decreased half-life, as compared to the non-derivatized molecules.

Genetically Engineered Non-Human Animals

Additionally included within the scope of the present invention are non-human animals such as mice, rats, or other rodents, rabbits, goats, or sheep, or other farm animals, in which the gene (or genes) encoding the native β10 polypeptide has (have) been disrupted ("knocked out") such that the level of expression of this gene or genes is (are) significantly decreased or completely abolished. Such animals may be prepared using techniques and methods such as those described in U.S. Pat. No. 5,557,032.

The present invention further includes non-human animals such as mice, rats, or other rodents, rabbits, goats, sheep, or other farm animals, in which either the native form of the β10 gene(s) for that animal or a heterologous β10 gene(s) is (are) over-expressed by the animal, thereby creating a "transgenic" animal. Such transgenic animals may be prepared using well known methods such as those described in U.S. Pat. No. 5,489,743 and PCT application No. WO94/28122.

The present invention further includes non-human animals in which the promoter for one or more of the β10 polypeptides is/are either activated or inactivated (e.g., by using homologous recombination methods) to alter the level of expression of native β10 polypeptide.

These non-human animals may be used for drug candidate screening. In such screening, the impact of a drug candidate on the animal may be measured. For example, drug candidates may decrease or increase the expression of the β10 gene. In certain embodiments, the amount of β10 polypeptide that is produced may be measured after the exposure of the animal to the drug candidate. Additionally, in certain embodiments, one may detect the actual impact of the drug candidate on the animal. For example, the overexpression of a particular gene may result in, or be associated with, a disease or pathological condition. In such cases, one may test a drug candidate's ability to decrease expression of the gene or its ability to prevent or inhibit a pathological condition. In other examples, the production of a particular metabolic product such as a fragment of a polypeptide, may result in, or be associated with, a disease or pathological condition. In such cases, one may test a drug candidate's ability to decrease the production of such a metabolic product or its ability to prevent or inhibit a pathological condition.

Microarray

It will be appreciated that DNA microarray technology can be utilized in accordance with the present invention. DNA microarrays are miniature, high density arrays of nucleic acids positioned on a solid support, such as glass. Each cell or element within the array has numerous copies of a single species of DNA which acts as a target for hybridization for its cognate mRNA. In expression profiling using DNA microarray technology, mRNA is first extracted from a cell or tissue sample and then converted enzymatically to fluorescently labeled cDNA. This material is hybridized to the microarray and unbound cDNA is removed by washing. The expression of discrete genes represented on the array is then visualized by quantitating the amount of labeled cDNA which is specifically bound to each target DNA. In this way, the expression of thousands of genes can be quantitated in a high throughput, parallel manner from a single sample of biological material.

This high throughput expression profiling has a broad range of applications with respect to the β10 molecules of the invention, including, but not limited to: the identification and validation of β10 disease-related genes as targets for therapeutics; molecular toxicology of β10 molecules and inhibitors thereof; stratification of populations and generation of surrogate markers for clinical trials; and enhancing β10 related small molecule drug discovery by aiding in the identification of selective compounds in high throughput screens (HTS).

Selective Binding Agents

As used herein, the term "selective binding agent" refers to a molecule which has specificity for one or more β10 polypeptides or α2/β10 heterodimers. Suitable selective binding agents include, but are not limited to, antibodies and derivatives thereof, polypeptides, and small molecules. Suitable selective binding agents may be prepared using methods known in the art. An exemplary β10 polypeptide or α2/β10 heterodimer selective binding agent of the present invention is capable of binding a certain portion of the β10 polypeptide or α2/β10 heterodimer thereby inhibiting the binding of the β10 polypeptide or α2/β10 heterodimer to the β10 polypeptide or α2/β10 heterodimer receptor(s).

Selective binding agents such as antibodies and antibody fragments that bind β10 polypeptides or α2/β10 heterodimers are within the scope of the present invention. The antibodies may be polyclonal including monospecific polyclonal, monoclonal (MAbs), recombinant, chimeric, humanized such as CDR-grafted, human, single chain, and/or bispecific, as well as fragments, variants or derivatives thereof. Antibody fragments include those portions of the antibody which bind to an epitope on the β10 polypeptide or α2/β10 heterodimer. Examples of such fragments include Fab and F(ab') fragments generated by enzymatic cleavage of full-length antibodies. Other binding fragments include those generated by recombinant DNA techniques, such as the expression of recombinant plasmids containing nucleic acid sequences encoding antibody variable regions.

Polyclonal antibodies directed toward β10 polypeptide or α2/β10 heterodimer generally are produced in animals (e.g., rabbits or mice) by means of multiple subcutaneous or intraperitoneal injections of β10 polypeptide or α2/β10 heterodimer and an adjuvant. It may be useful to conjugate a β10 polypeptide or α2/β10 heterodimer to a carrier protein that is immunogenic in the species to be immunized, such as keyhole limpet heocyanin, serum, albumin, bovine thyroglobulin, or soybean trypsin inhibitor. Also, aggregating agents such as alum are used to enhance the immune response. After immunization, the animals are bled and the serum is assayed for anti-β10 polypeptide or anti-α2/β10 heterodimer antibody titer.

Monoclonal antibodies directed toward β10 polypeptide or α2/β10 heterodimer are produced using any method which provides for the production of antibody molecules by continuous cell lines in culture. Examples of suitable methods for preparing monoclonal antibodies include the hybridoma methods of Kohler et al., *Nature,* 256:495-497 (1975) and the human B-cell hybridoma method, Kozbor, *J. Immunol.,* 133: 3001 (1984); Brodeur et al., Monoclonal Antibody Production Techniques and Applications, pp. 51-63 (Marcel Dekker, Inc., New York, 1987). Also provided by the invention are hybridoma cell lines which produce monoclonal antibodies reactive with β10 polypeptide or α2/β10 heterodimer of this invention.

Monoclonal antibodies of the invention may be modified for use as therapeutics. One embodiment is a "chimeric" antibody in which a portion of the heavy and/or light chain is identical with or homologous to a corresponding sequence in antibodies derived from a particular species or belonging to a particular antibody class or subclass, while the remainder of the chain(s) is identical with or homologous to a corresponding sequence in antibodies derived from another species or belonging to another antibody class or subclass. Also included are fragments of such antibodies, so long as they exhibit the desired biological activity. See, U.S. Pat. No. 4,816,567; Morrison et al., *Proc. Natl. Acad. Sci.,* 81:6851-6855 (1985).

In another embodiment, a monoclonal antibody of the invention is a "humanized" antibody. Methods for humanizing non-human antibodies are well known in the art. See U.S. Pat. Nos. 5,585,089, and 5,693,762. Generally, a humanized antibody has one or more amino acid residues introduced into it from a source which is non-human. Humanization can be performed, for example, using methods described in the art (Jones et al., *Nature* 321:522-525 (1986); Riechmann et al., *Nature,* 332:323-327 (1988); Verhoeyen et al., *Science* 239: 1534-1536 (1988)), by substituting at least a portion of a rodent complementarity-determining region (CDR) for the corresponding regions of a human antibody.

Also encompassed by the invention are human antibodies which bind β10 polypeptide or α2/β10 heterodimer. Using transgenic animals (e.g., mice) that are capable of producing a repertoire of human antibodies in the absence of endogenous immunoglobulin production such antibodies are produced by immunization with a β10 polypeptide or α2/β10 heterodimer antigen (i.e., having at least 6 contiguous amino acids), optionally conjugated to a carrier. See, for example, Jakobovits et al., *Proc. Natl. Acad. Sci.,* 90:2551-2555 (1993); Jakobovits et al., *Nature* 362:255-258 (1993); Bruggermann et al., *Year in Immuno.,* 7:33 (1993). In one method, such transgenic animals are produced by incapacitating the endogenous loci encoding the heavy and light immunoglobulin chains therein, and inserting loci encoding human heavy and light chain proteins into the genome thereof. Partially modified animals, that is those having less than the full complement of modifications, are then cross-bred to obtain an animal having all of the desired immune system modifications. When administered an immunogen, these transgenic animals produce antibodies with human (rather than e.g., murine) amino acid sequences, including variable regions which are immunospecific for these antigens. See PCT application nos. PCT/US96/05928 and PCT/US93/06926. Additional methods are described in U.S. Pat. No. 5,545,807, PCT application nos. PCT/US91/245, PCT/GB89/01207, and in EP 546073B1 and EP 546073A1. Human antibodies may also be produced by the expression of recombinant DNA in host cells or by expression in hybridoma cells as described herein.

In an alternative embodiment, human antibodies can be produced from phage-display libraries (Hoogenboom et al., *J. Mol. Biol.* 227:381 (1991); Marks et al., *J. Mol. Biol.* 222:581 (1991). These processes mimic immune selection through the display of antibody repertoires on the surface of filamentous bacteriophage, and subsequent selection of phage by their binding to an antigen of choice. One such technique is described in PCT Application no. PCT/US98/17364, which describes the isolation of high affinity and functional agonistic antibodies for MPL- and msk-receptors using such an approach.

Chimeric, CDR grafted, and humanized antibodies are typically produced by recombinant methods. Nucleic acids encoding the antibodies are introduced into host cells and expressed using materials and procedures described herein. In a preferred embodiment, the antibodies are produced in mammalian host cells, such as CHO cells. Monoclonal (e.g., human) antibodies may be produced by the expression of recombinant DNA in host cells or by expression in hybridoma cells as described herein.

The anti-β10 polypeptide antibodies or anti-α2/β10 heterodimer antibodies of the invention may be employed in any known assay method, such as competitive binding assays, direct and indirect sandwich assays, and immunoprecipitation assays (Sola, Monoclonal Antibodies: A Manual of Techniques, pp. 147-158, CRC Press, Inc., 1987) for the detection and quantitation of β10 polypeptide or α2/β10 heterodimer. The antibodies will bind the β10 polypeptide or α2/β10 heterodimer with an affinity which is appropriate for the assay method being employed.

For diagnostic applications, in certain embodiments, anti-β10 polypeptide antibodies or anti-α2/β10 heterodimer antibodies may be labeled with a detectable moiety. The detectable moiety can be any one which is capable of producing, either directly or indirectly, a detectable signal. For example, the detectable moiety may be a radioisotope, such as $^3H$, $^{14}C$, $^{32}P$, $^{35}S$, or $^{125}I$, a fluorescent or chemiluminescent compound, such as fluorescein isothiocyanate, rhodamine, or luciferin; or an enzyme, such as alkaline phosphatase, α-galactosidase, or horseradish peroxidase (Bayer et al., *Meth. Enz.*, 184:138-163 (1990).

Competitive binding assays rely on the ability of a labeled standard (e.g., a β10 polypeptide or α2/β10 heterodimer or an immunologically reactive portion thereof) to compete with the test sample analyte (a β10 polypeptide or α2/β10 heterodimer) for binding with a limited amount of anti-β10 polypeptide antibody or anti-α2/β10 heterodimer antibody. The amount of β10 polypeptide or α2/β10 heterodimer in the test sample is inversely proportional to the amount of standard that becomes bound to the antibodies. To facilitate determining the amount of standard that becomes bound, the antibodies typically are insolubilized before or after the competition, so that the standard and analyte that are bound to the antibodies may conveniently be separated from the standard and analyte which remain unbound.

Sandwich assays typically involve the use of two antibodies, each capable of binding to a different immunogenic portion, or epitope, of the protein to be detected and/or quantitated. In a sandwich assay, the test sample analyte is typically bound by a first antibody which is immobilized on a solid support, and thereafter a second antibody binds to the analyte, thus forming an insoluble three part complex. See, e.g., U.S. Pat. No. 4,376,110. The second antibody may itself be labeled with a detectable moiety (direct sandwich assays) or may be measured using an anti-immunoglobulin antibody that is labeled with a detectable moiety (indirect sandwich assays). For example, one type of sandwich assay is an enzyme-linked immunosorbent assay (ELISA), in which case the detectable moiety is an enzyme.

The selective binding agents, including anti-β10 polypeptide antibodies or anti-α2/β10 heterodimer antibodies, also are useful for in vivo imaging. An antibody labeled with a detectable moiety may be administered to an animal, preferably into the bloodstream, and the presence and location of the labeled antibody in the host is assayed. The antibody may be labeled with any moiety that is detectable in an animal, whether by nuclear magnetic resonance, radiology, or other detection means known in the art.

Selective binding agents of the invention, including antibodies, may be used as therapeutics. These therapeutic agents are generally agonists or antagonists, in that they either enhance or reduce, respectively, at least one of the biological activities of a β10 polypeptide or α2/β10 heterodimer according to this invention. In one embodiment, antagonist antibodies of the invention are antibodies or binding fragments thereof which are capable of specifically binding to a β10 polypeptide or α2/β10 heterodimer and which are capable of inhibiting or eliminating the functional activity of a β10 polypeptide or α2/β10 heterodimer in vivo or in vitro. In preferred embodiments, the selective binding agent, e.g., an antagonist antibody, will inhibit the functional activity of a β10 polypeptide or α2/β10 heterodimer by at least about 50%, and preferably by at least about 80%. In another embodiment, the selective binding agent may be an antibody that is capable of interacting with a β10 polypeptide or α2/β10 heterodimer binding partner (a ligand or receptor) thereby inhibiting or eliminating β10 polypeptide or α2/β10 heterodimer activity in vitro or in vivo. Selective binding agents, including agonist and antagonist anti-β10 polypeptide antibodies or anti-α2/β10 heterodimer antibodies, are identified by screening assays which are well known in the art.

The invention also relates to a kit comprising β10 polypeptide or α2/β10 heterodimer selective binding agents (such as antibodies) and other reagents useful for detecting β10 polypeptide or α2/β10 heterodimer levels in biological samples. Such reagents may include, a detectable label, blocking serum, positive and negative control samples, and detection reagents.

β10 polypeptide or α2/β10 heterodimer of this invention can also be used to clone β10 polypeptide or α2/β10 heterodimer receptor(s), using an "expression cloning" strategy. Radiolabeled (125-Iodine) β10 polypeptide or α2/β10 heterodimer or "affinity/activity-tagged" β10 polypeptide or α2/β10 heterodimer (such as an Fc fusion or an alkaline phosphatase fusion) can be used in binding assays to identify a cell type or cell line or tissue that expresses β10 polypeptide or α2/β10 heterodimer receptor(s). RNA isolated from such cells or tissues would be converted to cDNA, cloned into a mammalian expression vector, and transfected into mammalian cells (for example, COS, 293) to create an expression library. Radiolabeled or tagged β10 polypeptide or α2/β10 heterodimer would then be used as an affinity ligand to identify and isolate the subset of cells in this library expressing the β10 polypeptide or α2/β10 heterodimer receptor(s) on their surface. DNA would be isolated from these cells and transfected into mammalian cells to create a secondary expression library in which the fraction of cells expressing β10 polypeptide or α2/β10 heterodimer receptor(s) would be many-fold higher than in the original library. This enrichment process would be repeated iteratively until a single recombinant clone containing a β10 polypeptide or α2/β10 heterodimer receptor is isolated. Isolation of the β10 polypeptide or α2/β10 heterodimer receptor(s) would be very useful in terms of being able to identify or develop novel agonists and antagonists of the β10 polypeptide or α2/β10 heterodimer signaling pathway(s). Such agonists and antagonists would include soluble β10 polypeptide or α2/β10 heterodimer receptor(s), anti-β10 polypeptide-receptor(s) antibodies or anti-α2/β10 heterodimer(s)-receptor(s) antibodies, small molecules or antisense oligonucleotides, and they could be used in the diagnosis and/or treatment of one or more of the diseases/disorders listed below.

Assaying for Other Modulators of β10 Polypeptide or α2/β10 Heterodimer Activity

In some situations, it may be desirable to identify molecules that are modulators, i.e., agonists or antagonists, of the activity of a β10 polypeptide or α2/β10 heterodimer of this invention. Natural or synthetic molecules that modulate the β10 polypeptide or α2/β10 heterodimer may be identified using one or more screening assays, such as those described herein. Such molecules may be administered either in an ex vivo manner, or in an in vivo manner by injection, or by oral delivery, implantation device, or the like.

"Test molecule(s)" refers to the molecule(s) that is/are under evaluation for the ability to modulate (i.e., increase or decrease) the activity of a β10 polypeptide or α2/β10 heterodimer of this invention. Most commonly, a test molecule will interact directly with the polypeptide or heterodimer. However, it is also contemplated that a test molecule may also modulate β10 polypeptide or α2/β10 heterodimer activity indirectly, such as by affecting β10 gene expression, or by binding to a β10 polypeptide or α2/β10 heterodimer binding partner (e.g., receptor or ligand). In one embodiment, a test molecule will bind to a β10 polypeptide or α2/β10 heterodimer with an affinity constant of at least about $10^{-6}$ M, preferably about $10^{-8}$ M, more preferably about $10^{-9}$ M, and even more preferably about $10^{-10}$ M.

Methods for identifying compounds which interact with β10 polypeptides or α2/β10 heterodimers of this invention are encompassed by the present invention. In certain embodiments, a β10 polypeptide or α2/β10 heterodimer is incubated with a test molecule under conditions which permit the interaction of the test molecule with the polypeptide, and the extent of the interaction can be measured. The test molecule(s) can be screened in a substantially purified form or in a crude mixture.

In certain embodiments, a β10 polypeptide or α2/β10 heterodimer agonist or antagonist may be a protein, peptide, carbohydrate, lipid, or small molecular weight molecule which interacts with the β10 polypeptide or α2/β10 heterodimer to regulate its activity. Molecules which regulate β10 polypeptide or α2/β10 heterodimer expression include nucleic acids which are complementary to nucleic acids encoding a β10 polypeptide of this invention, or are complementary to nucleic acids sequences which direct, control or influence the expression of the β10 polypeptide or α2/β10 heterodimer and which act as anti-sense regulators of expression.

Once a set of test molecules has been identified as interacting with a β10 polypeptide or α2/β10 heterodimer the molecules may be further evaluated for their ability to increase or decrease β10 polypeptide or α2/β10 heterodimer activity. The measurement of the interaction of test molecules with β10 polypeptides or α2/β10 heterodimers may be carried out in several formats, including cell-based binding assays, membrane binding assays, solution-phase assays and immunoassays. In general, test molecules are incubated with a β10 polypeptide or α2/β10 heterodimer for a specified period of time, and β10 polypeptide or α2/β10 heterodimer activity is determined by one or more assays for measuring biological activity.

The interaction of test molecules with β10 polypeptides or α2/β10 heterodimers according to this invention may also be assayed directly using polyclonal or monoclonal antibodies in an immunoassay. Alternatively, modified forms of β10 polypeptides or α2/β10 heterodimers containing epitope tags as described herein may be used in immunoassays.

In the event that β10 polypeptides or α2/β10 heterodimers display biological activity through an interaction with a binding partner (e.g., a receptor or a ligand), a variety of in vitro assays may be used to measure the binding of a β10 polypeptide or α2/β10 heterodimer to the corresponding binding partner (such as a selective binding agent, receptor, or ligand). These assays may be used to screen test molecules for their ability to increase or decrease the rate and/or the extent of binding of a β10 polypeptide or α2/β10 heterodimer to its binding partner. In one assay, a β10 polypeptide or α2/β10 heterodimer is immobilized in the wells of a microtiter plate. Radiolabeled β10 polypeptide or α2/β10 heterodimer binding partner (for example, iodinated β10 polypeptide or α2/β10 heterodimer binding partner) and the test molecule(s) can then be added either one at a time (in either order) or simultaneously to the wells. After incubation, the wells can be washed and counted, using a scintillation counter, for radioactivity to determine the extent to which the binding partner bound to the β10 polypeptide or α2/β10 heterodimer. Typically, the molecules will be tested over a range of concentrations, and a series of control wells lacking one or more elements of the test assays can be used for accuracy in the evaluation of the results. An alternative to this method involves reversing the "positions" of the proteins, i.e., immobilizing β10 polypeptide or α2/β10 heterodimer binding partner to the microtiter plate wells, incubating with the test molecule and radiolabeled β10 polypeptide or α2/β10 heterodimer and determining the extent of β10 polypeptide or α2/β10 heterodimer binding. See, for example, chapter 18, *Current Protocols in Molecular Biology*, Ausubel et al., eds., John Wiley & Sons, New York, N.Y. (1995).

As an alternative to radiolabeling, a β10 polypeptide or α2/β10 heterodimer or its respective binding partner may be conjugated to biotin and the presence of biotinylated protein can then be detected using streptavidin linked to an enzyme, such as horseradish peroxidase (HRP) or alkaline phosphatase (AP), that can be detected colorometrically, or by fluorescent tagging of streptavidin. An antibody directed to a β10 polypeptide or α2/β10 heterodimer or to a β10 polypeptide or α2/β10 heterodimer binding partner and conjugated to biotin may also be used and can be detected after incubation with enzyme-linked streptavidin linked to AP or HRP.

A β10 polypeptide or α2/β10 heterodimer or a β10 polypeptide or α2/β10 heterodimer binding partner can also be immobilized by attachment to agarose beads, acrylic beads or other types of such inert solid phase substrates. The substrate-protein complex can be placed in a solution containing the complementary protein and the test compound. After incubation, the beads can be precipitated by centrifugation, and the amount of binding between a β10 polypeptide or α2/β10 heterodimer and its respective binding partner can be assessed using the methods described herein. Alternatively, the substrate-protein complex can be immobilized in a column, and the test molecule and complementary protein are passed through the column. The formation of a complex between a β10 polypeptide or α2/β10 heterodimer and its respective binding partner can then be assessed using any of the techniques set forth herein, i.e., radiolabeling, antibody binding, or the like.

Another in vitro assay that is useful for identifying a test molecule which increases or decreases the formation of a complex between a β10 polypeptide or α2/β10 heterodimer and a corresponding β10 polypeptide or α2/β10 heterodimer binding partner is a surface plasmon resonance detector system such as the BIAcore assay system (Pharmacia, Piscataway, N.J.). The BIAcore system may be carried out using the manufacturer's protocol. This assay essentially involves the covalent binding of either a β10 polypeptide, α2/β10 heterodimer, β10 polypeptide binding partner or α2/β10 heterodimer binding partner to a dextran-coated sensor chip which is located in a detector. The test compound and the other complementary protein can then be injected, either simultaneously or sequentially, into the chamber containing the sensor chip. The amount of complementary protein that binds can be assessed based on the change in molecular mass which is physically associated with the dextran-coated side of the sensor chip; the change in molecular mass can be measured by the detector system.

In some cases, it may be desirable to evaluate two or more test compounds together for their ability to increase or decrease the formation of a complex between β10 polypeptide or α2/β10 heterodimer and a corresponding β10 polypeptide or α2/β10 heterodimer binding partner. In these cases, the assays set forth herein can be readily modified by adding such additional test compound(s) either simultaneous with, or subsequent to, the first test compound. The remainder of the steps in the assay are as set forth herein.

In vitro assays such as those described herein may be used advantageously to screen large numbers of compounds for effects on complex formation by the β10 polypeptide or α2/β10 heterodimer and a corresponding β10 polypeptide or α2/β10 heterodimer binding partner. The assays may be automated to screen compounds generated in phage display, synthetic peptide, and chemical synthesis libraries.

Compounds which increase or decrease the formation of a complex between a β10 polypeptide or α2/β10 heterodimer and a corresponding β10 polypeptide or α2/β10 heterodimer binding partner may also be screened in cell culture using cells and cell lines expressing either β10 polypeptide or α2/β10 heterodimer and a corresponding β10 polypeptide or α2/β10 heterodimer binding partner. Cells and cell lines may be obtained from any mammal, but preferably will be from human or other primate, canine, or rodent sources. The binding of a β10 polypeptide or α2/β10 heterodimer to cells expressing the corresponding β10 polypeptide or α2/β10 heterodimer binding partner at the surface is evaluated in the presence or absence of test molecules, and the extent of binding may be determined by, for example, flow cytometry using a biotinylated antibody to a β10 polypeptide or α2/β10 heterodimer binding partner. Cell culture assays can be used advantageously to further evaluate compounds that score positive in protein binding assays described herein.

Cell cultures can also be used to screen the impact of a drug candidate. For example, drug candidates may decrease or increase the expression of the β10 gene. In certain embodiments, the amount of β10 polypeptide or α2/β10 heterodimer that is produced may be measured after exposure of the cell culture to the drug candidate. In certain embodiments, one may detect the actual impact of the drug candidate on the cell culture. For example, the overexpression of a particular gene may have a particular impact on the cell culture. In such cases, one may test a drug candidate's ability to increase or decrease the expression of the gene or its ability to prevent or inhibit a particular impact on the cell culture. In other examples, the production of a particular metabolic product such as a fragment of a polypeptide, may result in, or be associated with, a disease or pathological condition. In such cases, one may test a drug candidate's ability to decrease the production of such a metabolic product in a cell culture.

Therapeutic/Diagnostic Applications of β10 Polypeptides, α2/β10 Heterodimers and Nucleic Acids Biological function is anticipated for a β10 polypeptide or an α2/β10 heterodimer similar to that of the glycoprotein hormones FAS, TSH, FSH, LH and CG, which, among other things, are known to act as growth factors in promoting the development (proliferation, differentiation) of prolactin producing cells, the thyroid gland and the gonads. These glycoproteins also act as endocrine hormones in their role as regulators of placental, thyroidal and gonadal function. FAS plays a role in stimulating prolactin secretion from decidual cells in the placenta, TSH plays a major role in the regulation of basal metabolism via the thyroid gland, and FSH, LH and CG play critical roles in male and female fertility, as well as in pregnancy. As such, a β10 polypeptide or an α2/β10 heterodimer may also play roles in the regulation of basal metabolism, the development/function of the gonads, fertility and pregnancy.

As shown in the example further below, β10 polypeptide is expressed in brain, liver, fetal liver, stomach, pituitary, colon, small intestine, thyroid gland, adrenal gland, pancreas, skin, peripheral blood leucocytes, spleen, testis and placenta. The fact that β10 is expressed in many of the organs and tissues that make up the endocrine system suggests an important role for a β10 polypeptide or an α2/β10 heterodimer in the regulation and coordination of one or more endocrine system functions. The endocrine system is known to exert major control over metabolism, physiological responses to stress, and the development and function of reproductive organs.

The expression of β10 in pituitary, pancreas, adrenal gland, thyroid gland, stomach, small intestine, colon and liver indicates a possible role for a β10 polypeptide or an α2/β10 heterodimer in the common function of these organs or tissues, namely, metabolism and energy/nutritional homeostasis (i.e., energy balance, basal metabolic rate, digestion, glucose homeostasis, distribution of body fat, general growth).

The expression of β10 in the pituitary and adrenal glands indicates a possible role for a β10 polypeptide or an α2/β10 heterodimer in one of the critical functions subserved by these two important organs, namely, the body's ability to cope with a variety of environmental and physiological stresses (for example, infection, fever, inflammation, fasting, high and low blood pressure, anxiety, shock). Consistent with these possible functions for a β10 polypeptide or an α2/β10 heterodimer is the expression of β10 in cells and organs known to be important components of the immune system (peripheral blood leucocytes, spleen, small intestine).

In addition, the expression of β10 in pituitary, testis and placenta indicates a possible role for a β10 polypeptide or an α2/β10 heterodimer in the shared function of these organs, specifically, fertility and pregnancy.

β10 polypeptide or an α2/β10 heterodimer may also act as a growth factor involved in the regeneration (proliferation and differentiation) of tissues or specialized cell types present in brain, liver, stomach, pituitary, colon, small intestine, thyroid gland, adrenal gland, pancreas, skin, peripheral blood leucocytes, spleen, testis and placenta.

Consistent with the three major areas of potential β10 polypeptide or an α2/β10 heterodimer function, i.e., (1) metabolism and energy/nutritional homeostasis, (2) physiological responses to stress (including immune system function) and (3) fertility and pregnancy, is the fact that α2, which forms a heterodimer with β10, is expressed (see Example 2 below) in many of the same organs/tissues (anterior pituitary, placenta, pancreas, adrenal cortex, intestinal crypts and gall bladder mucosa) that play important roles in these 3 major areas.

Based on the above described potential functions, β10 polypeptide or an α2/β10 heterodimer may be useful for the treatment and/or diagnosis of metabolic or energy/nutritional homeostasic disorders. Examples of such disorders include, but are not limited to, obesity, wasting syndromes (for example, cancer associated cachexia), myopathies, gastrointestinal disorders, diabetes, growth failure, hypercholesterolemia, atherosclerosis and aging. Other diseases involving metabolic or energy/nutritional homeostasic disorders are encompassed within the therapeutic and diagnostic utilities that are part of the invention.

Based on the above described potential functions, β10 polypeptide or an α2/β10 heterodimer may be useful for the treatment and/or diagnosis of disorders related to physiological responses to stress (including immune system functions). Examples of such disorders include, but are not limited to, hypertension, immune system dysfunction (for example, excessive inflammation, autoimmune disease, susceptibility to infection such as AIDS, poor wound healing, psoriasis, asthma, arthritis and allergies), shock, anxiety, and high or low blood pressure. Other diseases involving physiological responses to stress, including, but not limited to, immune system functions, are also encompassed within the therapeutic and diagnostic utilities that are part of the invention.

Based on the above described potential functions, β10 polypeptide or an α2/β10 heterodimer may be useful for the treatment and/or diagnosis of disorders related to pregnancy and/or the development and function of reproductive organs. Examples of such disorders include, but are not limited to, infertility, fertility (contraception), impotence, endometriosis, menopause, miscarriage, pre-term labor and delivery. Other diseases involving pregnancy and/or the development and function of reproductive organs are also encompassed within the therapeutic and diagnostic utilities that are part of the invention.

Based on the fact that the β10 polypeptide or an α2/β10 heterodimer is likely to have hormone/growth-factor activities, β10 polypeptide or an α2/β10 heterodimer may be useful for the treatment and/or diagnosis of disorders that could be treated by increasing cell proliferation and/or differentiation. Examples of such disorders include, but are not limited to, tissue damage/degeneration (such as caused by cancer treatments, infections, autoimmune diseases), aging and wound healing. Other diseases that could be treated by increasing cell proliferation and/or differentiation are also encompassed within the therapeutic and diagnostic utilities that are part of the invention.

Based on the fact that the β10 polypeptide or an α2/β10 heterodimer is likely to have hormone/growth-factor activities, β10 polypeptide or an α2/β10 heterodimer may be useful for the treatment and/or diagnosis of disorders that could be treated by decreasing cell proliferation and/or differentiation. Examples of such disorders include, but are not limited to, cancers, hyperplasias and hypertrophies. Other diseases that could be treated by decreasing cell proliferation and/or differentiation are also encompassed within the therapeutic and diagnostic utilities that are part of the invention.

Other diseases caused or mediated by undesirable levels of β10 polypeptide or an α2/β10 heterodimer are encompassed within the therapeutic and diagnostic utilities that are part of the invention. By way of illustration, such undesirable levels include excessively elevated levels and sub-normal levels.

Transgenic mice were made that overexpressed mouse α2 alone, mouse β10 alone or the mouse α2/β10 heterodimer (see example 6). Only those transgenics over expressing the α2/β10 heterodimer showed distinct phenotypic differences as compared to control mice. The α2/β10 overexpressor transgenic mice exhibited a phenotype characterized by bilateral thyroid enlargement with multiple follicular papillary adenomas and resulting hyperthyroidism, as indicated by elevated serum T4 levels. Other phenotypic changes were felt to be related to the systemic hyperthyroid state, and included moderate hepatomegaly, hepatocellular hyperplasia, and slightly decreased serum cholesterol levels, bilateral renal hypertrophy, and a mild to moderate leukocytosis with a predominance of lymphocytes (see example 6). Thus in a normal mouse setting α2/β10 clearly has a thyroid stimulating hormone (TSH) like activity. Due to the high level of amino acid conservation between mouse α2 and human α2 [88.5% identity and 90.4% similarity for the predicted mature forms (ie. without signal peptide)], the high level of amino acid conservation between mouse β10 and human β10 [93.4% identity and 97.2% similarity for the predicted mature forms (ie. without signal peptide)], and the very high level of similarity between mouse thyroid gland biology and human thyroid gland biology, it is anticipated that human α2/β10 heterodimer has the same thyroid stimulating hormone (TSH) like activity as that found for the mouse α2/β10 heterodimer. In addition to TSH-like activity, α2/β10 may have other, distinct, biological effects in different physiological settings (i.e., disease conditions), as described in greater detail further herein.

TSH influences basal metabolism by regulating the production of thyroid hormones and is used clinically for enhancing the detection and treatment of thyroid carcinoma; see McEvoy, G.(ed.), *AHFS Drug Information,* pp. 2041-2042, American Society of Health-System Pharmacists, Inc., Bethesda, Md. (1998). In addition, diagnostic tests for measuring TSH levels in the blood are commonly used for determining the functional status of the thyroid gland when thyroid gland disorder is suspected. It is likely that human α2/β10 will have similar clinical utilities as TSH and will be useful for the treatment and diagnosis of thyroid gland related diseases and disorders. In addition, human α2/β10 may have other therapeutic and diagnostic uses which are described herein. It is reasonable to surmise that human α2/β10 selective binding agents, for example, antibodies, will have similar clinical utilities to TSH selective binding agents and will therefore be useful for the treatment and diagnosis of thyroid gland related diseases and disorders. In addition, human α2/β10 selective binding agents may have other therapeutic and diagnostic uses as described herein.

Compositions and Administration

Therapeutic compositions are within the scope of the present invention. Such pharmaceutical compositions may comprise a therapeutically effective amount of a β10 polypeptide, α2/β10 heterodimer or a β10 nucleic acid molecule in admixture with a pharmaceutically or physiologically acceptable formulation agent selected for suitability with the mode of administration. Pharmaceutical compositions may comprise a therapeutically effective amount of one or more β10 polypeptide or α2/β10 heterodimer selective binding agents in admixture with a pharmaceutically or physiologically acceptable formulation agent selected for suitability with the mode of administration.

Acceptable formulation materials preferably are nontoxic to recipients at the dosages and concentrations employed.

The pharmaceutical composition may contain formulation materials for modifying, maintaining or preserving, for example, the pH, osmolarity, viscosity, clarity, color, isotonicity, odor, sterility, stability, rate of dissolution or release, adsorption or penetration of the composition. Suitable formulation materials include, but are not limited to, amino acids (such as glycine, glutamine, asparagine, arginine or lysine), antimicrobials, antioxidants (such as ascorbic acid, sodium sulfite or sodium hydrogen-sulfite), buffers (such as borate, bicarbonate, Tris-HCl, citrates, phosphates, other organic acids), bulking agents (such as mannitol or glycine), chelating agents (such as ethylenediamine tetraacetic acid (EDTA)), complexing agents (such as caffeine, polyvinylpyrrolidone, beta-cyclodextrin or hydroxypropyl-beta-cyclodextrin), fillers, monosaccharides, disaccharides, and other carbohydrates (such as glucose, mannose, or dextrins), proteins (such as serum albumin, gelatin or immunoglobulins), coloring, flavoring and diluting agents, emulsifying agents, hydrophilic polymers (such as polyvinylpyrrolidone), low molecular weight polypeptides, salt-forming counterions (such as sodium), preservatives (such as benzalkonium chloride, benzoic acid, salicylic acid, thimerosal, phenethyl alcohol, methylparaben, propylparaben, chlorhexidine, sorbic acid or hydrogen peroxide), solvents (such as glycerin, propylene glycol or polyethylene glycol), sugar alcohols (such as mannitol or sorbitol), suspending agents, surfactants or wetting agents (such as pluronics, PEG, sorbitan esters, polysorbates such as polysorbate 20, polysorbate 80, triton, tromethamine, lecithin, cholesterol, tyloxapal), stability enhancing agents (sucrose or sorbitol), tonicity enhancing agents (such as alkali metal halides (preferably sodium or potassium chloride), mannitol sorbitol), delivery vehicles, diluents, excipients and/or pharmaceutical adjuvants. (*Remington's Pharmaceutical Sciences*, 18$^{th}$ Edition, A. R. Gennaro, ed., Mack Publishing Company [1990]).

The optimal pharmaceutical composition will be determined by one skilled in the art depending upon, for example, the intended route of administration, delivery format, and desired dosage. See for example, Remington's Pharmaceutical Sciences, supra. Such compositions may influence the physical state, stability, rate of in vivo release, and rate of in vivo clearance of β10 polypeptide or α2/β10 heterodimer molecule.

The primary vehicle or carrier in a pharmaceutical composition may be either aqueous or non-aqueous in nature. For example, a suitable vehicle or carrier may be water for injection, physiological saline solution, or artificial cerebrospinal fluid, possibly supplemented with other materials common in compositions for parenteral administration. Neutral buffered saline or saline mixed with serum albumin are further exemplary vehicles. Other exemplary pharmaceutical compositions comprise Tris buffer of about pH 7.0-8.5, or acetate buffer of about pH 4.0-5.5, which may further include sorbitol or a suitable substitute therefor. In one embodiment of the present invention, β10 polypeptide or α2/β10 heterodimer compositions may be prepared for storage by mixing the selected composition having the desired degree of purity with optional formulation agents (*Remington's Pharmaceutical Sciences, supra*) in the form of a lyophilized cake or an aqueous solution. Further, the β10 polypeptide or α2/β10 heterodimer product may be formulated as a lyophilizate using appropriate excipients such as sucrose.

The pharmaceutical compositions of this invention can be selected for parenteral delivery. Alternatively, the compositions may be selected for inhalation or for delivery through the digestive tract, such as orally. The preparation of such pharmaceutically acceptable compositions is within the skill of the art.

The formulation components are present in concentrations that are acceptable to the site of administration. For example, buffers are used to maintain the composition at physiological pH or at slightly lower pH, typically within a pH range of from about 5 to about 8.

When parenteral administration is contemplated, the therapeutic compositions for use in this invention may be in the form of a pyrogen-free, parenterally acceptable aqueous solution comprising the desired β10 polypeptide or α2/β10 heterodimer molecule in a pharmaceutically acceptable vehicle. A particularly suitable vehicle for parenteral injection is sterile distilled water in which a β10 polypeptide or α2/β10 heterodimer molecule is formulated as a sterile, isotonic solution, properly preserved. Yet another preparation can involve the formulation of the desired molecule with an agent, such as injectable microspheres, bio-erodible particles, polymeric compounds (polylactic acid, polyglycolic acid), or beads, or liposomes, that provides for the controlled or sustained release of the product which may then be delivered as a depot injection. Hyaluronic acid may also be used, and this may have the effect of promoting sustained duration in the circulation. Other suitable means for the introduction of the desired molecule include implantable drug delivery devices.

In one embodiment, a pharmaceutical composition may be formulated for inhalation. For example, a β10 polypeptide or α2/β10 heterodimer molecule may be formulated as a dry powder for inhalation. β10 polypeptide, α2/β10 heterodimer or β10 nucleic acid molecule inhalation solutions may also be formulated with a propellant for aerosol delivery. In yet another embodiment, solutions may be nebulized. Pulmonary administration is further described in PCT application no. PCT/US94/001875, which describes pulmonary delivery of chemically modified proteins.

It is also contemplated that certain formulations may be administered orally. In one embodiment of the present invention, β10 polypeptide or α2/β10 heterodimer molecules which are administered in this fashion can be formulated with or without those carriers customarily used in the compounding of solid dosage forms such as tablets and capsules. For example, a capsule may be designed to release the active portion of the formulation at the point in the gastrointestinal tract when bioavailability is maximized and pre-systemic degradation is minimized. Additional agents can be included to facilitate absorption of the β10 polypeptide or α2/β10 heterodimer molecule. Diluents, flavorings, low melting point waxes, vegetable oils, lubricants, suspending agents, tablet disintegrating agents, and binders may also be employed.

Another pharmaceutical composition may involve an effective quantity of β10 polypeptide or α2/β10 heterodimer molecules in a mixture with non-toxic excipients which are suitable for the manufacture of tablets. By dissolving the tablets in sterile water, or other appropriate vehicle, solutions can be prepared in unit dose form. Suitable excipients include, but are not limited to, inert diluents, such as calcium carbonate, sodium carbonate or bicarbonate, lactose, or calcium phosphate; or binding agents, such as starch, gelatin, or acacia; or lubricating agents such as magnesium stearate, stearic acid, or talc.

Additional pharmaceutical compositions will be evident to those skilled in the art, including formulations involving β10 polypeptides or α2/β10 heterodimers in sustained- or controlled-delivery formulations. Techniques for formulating a variety of other sustained- or controlled-delivery means, such as liposome carriers, bio-erodible microparticles or porous beads and depot injections, are also known to those skilled in the art. See for example, PCT/US93/00829 which describes controlled release of porous polymeric microparticles for the delivery of pharmaceutical compositions. Additional examples of sustained-release preparations include semipermeable polymer matrices in the form of shaped articles, e.g. films, or microcapsules. Sustained release matrices may include polyesters, hydrogels, polylactides (U.S. Pat. No. 3,773,919, EP 58,481), copolymers of L-glutamic acid and gamma ethyl-L-glutamate (Sidman et al., *Biopolymers*, 22:547-556 (1983)), poly (2-hydroxyethyl-methacrylate) (Langer et al., *J. Biomed. Mater. Res.*, 15:167-277 (1981) and Langer, *Chem. Tech.*, 12:98-105 (1982)), ethylene vinyl acetate (Langer et al., supra) or poly-D(−)-3-hydroxybutyric acid (EP 133,988). Sustained-release compositions also may include liposomes, which can be prepared by any of several methods known in the art. See e.g., Eppstein et al., *Proc. Natl. Acad. Sci. USA*, 82:3688-3692 (1985); EP 36,676; EP 88,046; EP 143,949.

The pharmaceutical composition to be used for in vivo administration typically must be sterile. This may be accomplished by filtration through sterile filtration membranes. Where the composition is lyophilized, sterilization using these methods may be conducted either prior to, or following, lyophilization and reconstitution. The composition for parenteral administration may be stored in lyophilized form or in solution. In addition, parenteral compositions generally are placed into a container having a sterile access port, for example, an intravenous solution bag or vial having a stopper pierceable by a hypodermic injection needle.

Once the pharmaceutical composition has been formulated, it may be stored in sterile vials as a solution, suspension, gel, emulsion, solid, or a dehydrated or lyophilized powder. Such formulations may be stored either in a ready-to-use form or in a form (e.g., lyophilized) requiring reconstitution prior to administration.

In a specific embodiment, the present invention is directed to kits for producing a single-dose administration unit. The kits may each contain both a first container having a dried protein and a second container having an aqueous formulation. Also included within the scope of this invention are kits containing single and multi-chambered pre-filled syringes (e.g., liquid syringes and lyosyringes).

An effective amount of a pharmaceutical composition to be employed therapeutically will depend, for example, upon the therapeutic context and objectives. One skilled in the art will appreciate that the appropriate dosage levels for treatment will thus vary depending, in part, upon the molecule delivered, the indication for which the β10 polypeptide or α2/β10 heterodimer molecule is being used, the route of administration, and the size (body weight, body surface or organ size) and condition (the age and general health) of the patient. Accordingly, the clinician may titer the dosage and modify the route of administration to obtain the optimal therapeutic effect. A typical dosage may range from about 0.1 µg/kg to up to about 100 mg/kg or more, depending on the factors mentioned above. In other embodiments, the dosage may range from 0.1 µg/kg up to about 100 mg/kg; or 1 µg/kg up to about 100 mg/kg; or 5 µg/kg up to about 100 mg/kg.

The frequency of dosing will depend upon the pharmacokinetic parameters of the β10 polypeptide or α2/β10 heterodimer molecule in the formulation used. Typically, a clinician will administer the composition until a dosage is reached that achieves the desired effect. The composition may therefore be administered as a single dose, or as two or more doses (which may or may not contain the same amount of the desired molecule) over time, or as a continuous infusion via implantation device or catheter. Further refinement of the appropriate dosage is routinely made by those of ordinary skill in the art and is within the ambit of tasks routinely performed by them. Appropriate dosages may be ascertained through use of appropriate dose-response data.

The route of administration of the pharmaceutical composition is in accord with known methods, e.g. oral, injection by intravenous, intraperitoneal, intracerebral (intra-parenchymal), intracerebroventricular, intramuscular, intra-ocular, intraarterial, intraportal, or intralesional routes, or by sustained release systems or implantation device. Where desired, the compositions may be administered by bolus injection or continuously by infusion, or by implantation device.

Alternatively or additionally, the composition may be administered locally via implantation of a membrane, sponge, or other appropriate material on to which the desired molecule has been absorbed or encapsulated. Where an implantation device is used, the device may be implanted into any suitable tissue or organ, and delivery of the desired molecule may be via diffusion, timed release bolus, or continuous administration.

In some cases, it may be desirable to use pharmaceutical compositions according to this invention in an ex vivo manner. In such instances, cells, tissues, or organs that have been removed from the patient are exposed to pharmaceutical compositions after which the cells, tissues and/or organs are subsequently implanted back into the patient.

In other cases, a β10 polypeptide or α2/β10 heterodimer of this invention can be delivered by implanting certain cells that have been genetically engineered, using methods such as those described herein, to express and secrete the polypeptide or heterodimer. Such cells may be animal or human cells, and may be autologous, heterologous, or xenogeneic. Optionally, the cells may be immortalized. In order to decrease the chance of an immunological response, the cells may be encapsulated to avoid infiltration of surrounding tissues. The encapsulation materials are typically biocompatible, semi-permeable polymeric enclosures or membranes that allow the release of the protein product(s) but prevent the destruction of the cells by the patient's immune system or by other detrimental factors from the surrounding tissues.

Additional embodiments of the present invention relate to cells and methods (e.g., homologous recombination and/or other recombinant production methods) for both the in vitro production of therapeutic polypeptides and for the production and delivery of therapeutic polypeptides by gene therapy or cell therapy. Homologous and other recombination methods may be used to modify a cell that contains a normally transcriptionally silent β10 gene, or an under expressed gene, and thereby produce a cell which expresses therapeutically efficacious amounts of β10 polypeptide or α2/β10 heterodimer.

Homologous recombination is a technique originally developed for targeting genes to induce or correct mutations in transcriptionally active genes (Kucherlapati, *Prog. in Nucl. Acid Res. & Mol. Biol.*, 36:301, 1989). The basic technique was developed as a method for introducing specific mutations into specific regions of the mammalian genome (Thomas et al., *Cell*, 44:419-428, 1986; Thomas and Capecchi, *Cell*, 51:503-512, 1987; Doetschman et al., *Proc. Natl. Acad. Sci.*, 85:8583-8587, 1988) or to correct specific mutations within defective genes (Doetschman et al., *Nature*, 330:576-578, 1987). Exemplary homologous recombination techniques are described in U.S. Pat. No. 5,272,071 (EP 9193051, EP Publication No. 505500; PCT/US90/07642, International Publication No. WO 91/09955).

Through homologous recombination, the DNA sequence to be inserted into the genome can be directed to a specific region of the gene of interest by attaching it to targeting DNA. The targeting DNA is a nucleotide sequence that is complementary (homologous) to a region of the genomic DNA. Small pieces of targeting DNA that are complementary to a specific region of the genome are put in contact with the parental strand during the DNA replication process. It is a general property of DNA that has been inserted into a cell to hybridize, and therefore, recombine with other pieces of endogenous DNA through shared homologous regions. If this complementary strand is attached to an oligonucleotide that contains a mutation or a different sequence or an additional nucleotide, it too is incorporated into the newly synthesized strand as a result of the recombination. As a result of the proofreading function, it is possible for the new sequence of DNA to serve as the template. Thus, the transferred DNA is incorporated into the genome.

Attached to these pieces of targeting DNA are regions of DNA which may interact with or control the expression of a β10 polypeptide, e.g., flanking sequences. For example, a promoter/enhancer element, a suppresser, or an exogenous transcription modulatory element is inserted in the genome of the intended host cell in proximity and orientation sufficient to influence the transcription of DNA encoding the desired β10 polypeptide. The control element controls a portion of the DNA present in the host cell genome. Thus, the expression of the desired β10 polypeptide or α2/β10 heterodimer may be achieved not by transfection of DNA that encodes the β10 gene itself, but rather by the use of targeting DNA (containing regions of homology with the endogenous gene of interest) coupled with DNA regulatory segments that provide the endogenous gene sequence with recognizable signals for transcription of the β10 gene.

In an exemplary method, the expression of a desired targeted gene in a cell (i.e., a desired endogenous cellular gene) is altered via homologous recombination into the cellular genome at a preselected site, by the introduction of DNA which includes at least a regulatory sequence, an exon and a splice donor site. These components are introduced into the chromosomal (genomic) DNA in such a manner that this, in effect, results in the production of a new transcription unit (in which the regulatory sequence, the exon and the splice donor site present in the DNA construct are operatively linked to the endogenous gene). As a result of the introduction of these components into the chromosomal DNA, the expression of the desired endogenous gene is altered.

Altered gene expression, as described herein, encompasses activating (or causing to be expressed) a gene which is normally silent (unexpressed) in the cell as obtained, as well as increasing the expression of a gene which is not expressed at physiologically significant levels in the cell as obtained. The embodiments further encompass changing the pattern of regulation or induction such that it is different from the pattern of regulation or induction that occurs in the cell as obtained, and reducing (including eliminating) the expression of a gene which is expressed in the cell as obtained.

One method by which homologous recombination can be used to increase, or cause, β10 polypeptide or α2/β10 heterodimer production from a cell's endogenous β10 gene involves first using homologous recombination to place a recombination sequence from a site-specific recombination system (e.g., Cre/loxP, FLP/FRT) (Sauer, *Current Opinion In Biotechnology*, 5:521-527, 1994; Sauer, *Methods In Enzymology*, 225:890-900, 1993) upstream (that is, 5' to) of the cell's endogenous genomic β10 polypeptide coding region. A plasmid containing a recombination site homologous to the site that was placed just upstream of the genomic β10 polypeptide coding region is introduced into the modified cell line along with the appropriate recombinase enzyme. This recombinase causes the plasmid to integrate, via the plasmid's recombination site, into the recombination site located just upstream of the genomic β10 polypeptide coding region in the cell line (Baubonis and Sauer, *Nucleic Acids Res.,* 21:2025-2029, 1993; O'Gorman et al., *Science,* 251:1351-1355, 1991). Any flanking sequences known to increase transcription (e.g., enhancer/promoter, intron, translational enhancer), if properly positioned in this plasmid, would integrate in such a manner as to create a new or modified transcriptional unit resulting in de novo or increased β10 polypeptide or α2/β10 heterodimer production from the cell's endogenous β10 gene.

A further method to use the cell line in which the site specific recombination sequence had been placed just upstream of the cell's endogenous genomic β10 polypeptide coding region is to use homologous recombination to introduce a second recombination site elsewhere in the cell line's genome. The appropriate recombinase enzyme is then introduced into the two-recombination-site cell line, causing a recombination event (deletion, inversion, translocation) (Sauer, *Current Opinion In Biotechnology, supra,* 1994; Sauer, *Methods In Enzymology, supra,* 1993) that would create a new or modified transcriptional unit resulting in de novo or increased β10 polypeptide or α2/β10 heterodimer production from the cell's endogenous β10 gene.

An additional approach for increasing, or causing, the expression of the β10 polypeptide from a cell's endogenous β10 gene involves increasing, or causing, the expression of a gene or genes (e.g., transcription factors) and/or decreasing the expression of a gene or genes (e.g., transcriptional repressors) in a manner which results in de novo or increased β10 polypeptide production from the cell's endogenous β10 gene. This method includes the introduction of a non-naturally occurring polypeptide (e.g., a polypeptide comprising a site specific DNA binding domain fused to a transcriptional factor domain) into the cell such that de novo or increased β10 polypeptide or α2/β10 heterodimer production from the cell's endogenous β10 gene results.

The present invention further relates to DNA constructs useful in the method of altering expression of a target gene. In certain embodiments, the exemplary DNA constructs comprise: (a) one or more targeting sequences; (b) a regulatory sequence; (c) an exon; and (d) an unpaired splice-donor site. The targeting sequence in the DNA construct directs the integration of elements (a)-(d) into a target gene in a cell such that the elements (b)-(d) are operatively linked to sequences of the endogenous target gene. In another embodiment, the DNA constructs comprise: (a) one or more targeting sequences, (b) a regulatory sequence, (c) an exon, (d) a splice-donor site, (e) an intron, and (f) a splice-acceptor site, wherein the targeting sequence directs the integration of elements (a)-(f) such that the elements of (b)-(f) are operatively linked to the endogenous gene. The targeting sequence is homologous to the preselected site in the cellular chromosomal DNA with which homologous recombination is to occur. In the construct, the exon is generally 3' of the regulatory sequence and the splice-donor site is 3' of the exon.

If the sequence of a particular gene is known, such as the nucleic acid sequence of the β10 gene presented herein, a piece of DNA that is complementary to a selected region of the gene can be synthesized or otherwise obtained, such as by appropriate restriction of the native DNA at specific recognition sites bounding the region of interest. This piece serves as a targeting sequence(s) upon insertion into the cell and will hybridize to its homologous region within the genome. If this hybridization occurs during DNA replication, this piece of DNA, and any additional sequence attached thereto, will act as an Okazaki fragment and will be incorporated into the newly synthesized daughter strand of DNA. The present invention, therefore, includes nucleotides encoding a β10 polypeptide, which nucleotides may be used as targeting sequences.

β10 polypeptide or α2/β10 heterodimer cell therapy, e.g., the implantation of cells producing β10 polypeptides or α2/β10 heterodimers is also contemplated. This embodiment involves implanting cells capable of synthesizing and secreting a biologically active form of the β10 polypeptide or α2/β10 heterodimer. Such β10 polypeptide or α2/β10 heterodimer-producing cells can be cells that are natural producers of β10 polypeptides or α2/β10 heterodimers or may be recombinant cells whose ability to produce β10 polypeptides or α2/β10 heterodimers has been augmented by transformation with a gene encoding the desired β10 polypeptide or with a gene augmenting the expression of β10 polypeptide or α2/β10 heterodimer. Such a modification may be accomplished by means of a vector suitable for delivering the gene as well as promoting its expression and secretion. In order to minimize a potential immunological reaction in patients being administered a β10 polypeptide or α2/β10 heterodimer as may occur with the administration of a polypeptide of a foreign species, it is preferred that the natural cells producing β10 polypeptide or α2/β10 heterodimer be of human origin and produce human β10 polypeptide or α2/β10 heterodimer. Likewise, it is preferred that the recombinant cells producing β10 polypeptide or α2/β10 heterodimer be transformed with an expression vector containing a gene encoding a human β10 polypeptide.

Implanted cells may be encapsulated to avoid the infiltration of surrounding tissue. Human or non-human animal cells may be implanted in patients in biocompatible, semipermeable polymeric enclosures or membranes that allow the release of β10 polypeptide or α2/β10 heterodimer but that prevent the destruction of the cells by the patient's immune system or by other detrimental factors from the surrounding tissue. Alternatively, the patient's own cells, transformed to produce β10 polypeptides or α2/β10 heterodimers ex vivo, may be implanted directly into the patient without such encapsulation.

Techniques for the encapsulation of living cells are known in the art, and the preparation of the encapsulated cells and their implantation in patients may be routinely accomplished. For example, Baetge et al. (WO95/05452; PCT/US94/09299) describe membrane capsules containing genetically engineered cells for the effective delivery of biologically active molecules. The capsules are biocompatible and are easily retrievable. The capsules encapsulate cells transfected with recombinant DNA molecules comprising DNA sequences coding for biologically active molecules operatively linked to promoters that are not subject to down regulation in vivo upon implantation into a mammalian host. The devices provide for the delivery of the molecules from living cells to specific sites within a recipient. In addition, see U.S. Pat. Nos. 4,892,538, 5,011,472, and 5,106,627. A system for encapsulating living cells is described in PCT Application no. PCT/US91/00157 of Aebischer et al. See also, PCT Application no. PCT/US91/00155 of Aebischer et al., Winn et al., *Exper. Neurol.*, 113: 322-329 (1991), Aebischer et al., *Exper. Neurol.*, 111:269-275 (1991); and Tresco et al., ASAIO, 38:17-23 (1992).

In vivo and in vitro gene therapy delivery of β10 polypeptides or α2/β10 heterodimers is also envisioned. One example of a gene therapy technique is to use the β10 gene (either genomic DNA, cDNA, and/or synthetic DNA) encoding a β10 polypeptide which may be operably linked to a constitutive or inducible promoter to form a "gene therapy DNA construct". The promoter may be homologous or heterologous to the endogenous gene, provided that it is active in the cell or tissue type into which the construct will be inserted. Other components of the gene therapy DNA construct may optionally include, DNA molecules designed for site-specific integration (e.g., endogenous sequences useful for homologous recombination), tissue-specific promoter, enhancer(s) or silencer(s), DNA molecules capable of providing a selective advantage over the parent cell, DNA molecules useful as labels to identify transformed cells, negative selection systems, cell specific binding agents (as, for example, for cell targeting), cell-specific internalization factors, and transcription factors to enhance expression by a vector as well as factors to enable vector manufacture.

A gene therapy DNA construct can then be introduced into cells (either ex vivo or in vivo) using viral or non-viral vectors. One means for introducing the gene therapy DNA construct is by means of viral vectors as described herein. Certain vectors, such as retroviral vectors, will deliver the DNA construct to the chromosomal DNA of the cells, and the gene can integrate into the chromosomal DNA. Other vectors will function as episomes, and the gene therapy DNA construct will remain in the cytoplasm.

In yet other embodiments, regulatory elements can be included for the controlled expression of the β10 gene in the target cell. Such elements are turned on in response to an appropriate effector. In this way, a therapeutic polypeptide can be expressed when desired. One conventional control means involves the use of small molecule dimerizers or rapalogs (as described in WO9641865 (PCT/US96/099486); WO9731898 (PCT/US97/03137) and WO9731899 (PCT/US95/03157) used to dimerize chimeric proteins which contain a small molecule-binding domain and a domain capable of initiating biological process, such as a DNA-binding protein or transcriptional activation protein. The dimerization of the proteins can be used to initiate transcription of the transgene.

An alternative regulation technology uses a method of storing proteins expressed from the gene of interest inside the cell as an aggregate or cluster. The gene of interest is expressed as a fusion protein that includes a conditional aggregation domain which results in the retention of the aggregated protein in the endoplasmic reticulum. The stored proteins are stable and inactive inside the cell. The proteins can be released, however, by administering a drug (e.g., small molecule ligand) that removes the conditional aggregation domain and thereby specifically breaks apart the aggregates or clusters so that the proteins may be secreted from the cell. See, *Science* 287:816-817, and 826-830 (2000).

Other suitable control means or gene switches include, but are not limited to, the following systems. Mifepristone (RU486) is used as a progesterone antagonist. The binding of a modified progesterone receptor ligand-binding domain to the progesterone antagonist activates transcription by forming a dimer of two transcription factors which then pass into the nucleus to bind DNA. The ligand binding domain is modified to eliminate the ability of the receptor to bind to the natural ligand. The modified steroid hormone receptor system is further described in U.S. Pat. No. 5,364,791; WO9640911, and WO9710337.

Yet another control system uses ecdysone (a fruit fly steroid hormone) which binds to and activates an ecdysone receptor (cytoplasmic receptor). The receptor then translocates to the nucleus to bind a specific DNA response element (promoter from ecdysone-responsive gene). The ecdysone receptor includes a transactivation domain/DNA-binding domain/ligand-binding domain to initiate transcription. The ecdysone system is further described in U.S. Pat. No. 5,514,578; WO9738117; WO9637609; and WO9303162.

Another control means uses a positive tetracycline-controllable transactivator. This system involves a mutated tet repressor protein DNA-binding domain (mutated tet R-4 amino acid changes which resulted in a reverse tetracycline-regulated transactivator protein, i.e., it binds to a tet operator in the presence of tetracycline) linked to a polypeptide which activates transcription. Such systems are described in U.S. Pat. Nos. 5,464,758; 5,650,298 and 5,654,168.

Additional expression control systems and nucleic acid constructs are described in U.S. Pat. Nos. 5,741,679 and 5,834,186, to Innovir Laboratories Inc.

In vivo gene therapy may be accomplished by introducing the gene encoding a β10 polypeptide into cells via local injection of a β10 nucleic acid molecule or by other appropriate viral or non-viral delivery vectors. Hefti, *Neurobiology*, 25:1418-1435 (1994). For example, a nucleic acid molecule encoding a β10 polypeptide of this invention may be contained in an adeno-associated virus (AAV) vector for delivery to the targeted cells (e.g., Johnson, International Publication No. WO95/34670; International Application No. PCT/US95/07178). The recombinant AAV genome typically contains AAV inverted terminal repeats flanking a DNA sequence encoding a β10 polypeptide operably linked to functional promoter and polyadenylation sequences.

Alternative suitable viral vectors include, but are not limited to, retrovirus, adenovirus, herpes simplex virus, lentivirus, hepatitis virus, parvovirus, papovavirus, poxvirus, alphavirus, coronavirus, rhabdovirus, paramyxovirus, and papilloma virus vectors. U.S. Pat. No. 5,672,344 describes an in vivo viral-mediated gene transfer system involving a recombinant neurotrophic HSV-1 vector. U.S. Pat. No. 5,399,346 provides examples of a process for providing a patient with a therapeutic protein by the delivery of human cells which have been treated in vitro to insert a DNA segment encoding a therapeutic protein. Additional methods and materials for the practice of gene therapy techniques are described in U.S. Pat. No. 5,631,236 involving adenoviral vectors; U.S. Pat. No. 5,672,510 involving retroviral vectors; and U.S. Pat. No. 5,635,399 involving retroviral vectors expressing cytokines.

Nonviral delivery methods include, but are not limited to, liposome-mediated transfer, naked DNA delivery (direct injection), receptor-mediated transfer (ligand-DNA complex), electroporation, calcium phosphate precipitation, and microparticle bombardment (e.g., gene gun). Gene therapy materials and methods may also include the use of inducible promoters, tissue-specific enhancer-promoters, DNA sequences designed for site-specific integration, DNA sequences capable of providing a selective advantage over the parent cell, labels to identify transformed cells, negative selection systems and expression control systems (safety measures), cell-specific binding agents (for cell targeting), cell-specific internalization factors, and transcription factors to enhance expression by a vector as well as methods of vector manufacture. Such additional methods and materials for the practice of gene therapy techniques are described in U.S. Pat. No. 4,970,154 involving electroporation techniques; WO96/40958 involving nuclear ligands; U.S. Pat. No. 5,679,559 describing a lipoprotein-containing system for gene delivery; U.S. Pat. No. 5,676,954 involving liposome carriers; U.S. Pat. No. 5,593,875 concerning methods for calcium phosphate transfection; and U.S. Pat. No. 4,945,050 wherein biologically active particles are propelled at cells at a speed whereby the particles penetrate the surface of the cells and become incorporated into the interior of the cells.

It is also contemplated that β10 gene therapy or cell therapy can further include the delivery of one or more additional polypeptide(s) in the same or a different cell(s). Such cells may be separately introduced into the patient, or the cells may be contained in a single implantable device, such as the encapsulating membrane described above, or the cells may be separately modified by means of viral vectors.

A means to increase endogenous β10 polypeptide expression in a cell via gene therapy is to insert one or more enhancer elements into the β10 polypeptide promoter, where the enhancer element(s) can serve to increase transcriptional activity of the β10 gene. The enhancer element(s) used will be selected based on the tissue in which one desires to activate the gene(s); enhancer elements known to confer promoter activation in that tissue will be selected. For example, if a gene encoding a β10 polypeptide is to be "turned on" in T-cells, the lck promoter enhancer element may be used. Here, the functional portion of the transcriptional element to be added may be inserted into a fragment of DNA containing the β10 polypeptide promoter (and optionally, inserted into a vector and/or 5' and/or 3' flanking sequence(s), etc.) using standard cloning techniques. This construct, known as a "homologous recombination construct", can then be introduced into the desired cells either ex vivo or in vivo.

Gene therapy can also be used to decrease β10 polypeptide or α2/β10 heterodimer expression by modifying the nucleotide sequence of the endogenous promoter(s). Such modification is typically accomplished via homologous recombination methods. For example, a DNA molecule containing all or a portion of the promoter of the β10 gene(s) selected for inactivation can be engineered to remove and/or replace pieces of the promoter that regulate transcription. For example the TATA box and/or the binding site of a transcriptional activator of the promoter may be deleted using standard molecular biology techniques; such deletion can inhibit promoter activity thereby repressing the transcription of the corresponding β10 gene. The deletion of the TATA box or the transcription activator binding site in the promoter may be accomplished by generating a DNA construct comprising all or the relevant portion of the β10 polypeptide promoter(s) (from the same or a related species as the β10 gene(s) to be regulated) in which one or more of the TATA box and/or transcriptional activator binding site nucleotides are mutated via substitution, deletion and/or insertion of one or more nucleotides. As a result, the TATA box and/or activator binding site has decreased activity or is rendered completely inactive. The construct will typically contain at least about 500 bases of DNA that correspond to the native (endogenous) 5' and 3' DNA sequences adjacent to the promoter segment that has been modified. The construct may be introduced into the appropriate cells (either ex vivo or in vivo) either directly or via a viral vector as described herein. Typically, the integration of the construct into the genomic DNA of the cells will be via homologous recombination, where the 5' and 3' DNA sequences in the promoter construct can serve to help integrate the modified promoter region via hybridization to the endogenous chromosomal DNA.

Other Uses of the Nucleic Acids and Polypeptides of this Invention

Nucleic acid molecules of the present invention (including those that do not themselves encode biologically active polypeptides) may be used to map the locations of the β10 gene and related genes on chromosomes. Mapping may be done by techniques known in the art, such as PCR amplification and in situ hybridization.

β10 nucleic acid molecules (including those that do not themselves encode biologically active polypeptides), may be useful as hybridization probes in diagnostic assays to test, either qualitatively or quantitatively, for the presence of a β10 DNA or corresponding RNA in mammalian tissue or bodily fluid samples.

The β10 polypeptides or α2/β10 heterodimers may be used (simultaneously or sequentially) in combination with one or more cytokines, growth factors, antibiotics, anti-inflammatories, and/or chemotherapeutic agents as is appropriate for the indication being treated.

Other methods may also be employed where it is desirable to inhibit the activity of one or more β10 polypeptides or α2/β10 heterodimers of this invention. Such inhibition may be effected by nucleic acid molecules which are complementary to and hybridize to expression control sequences (triple helix formation) or to β10 mRNA. For example, antisense DNA or RNA molecules, which have a sequence that is complementary to at least a portion of the selected β10 gene(s) can be introduced into the cell. Anti-sense probes may be designed by available techniques using the sequence of the β10 polypeptide disclosed herein. Typically, each such antisense molecule will be complementary to the start site (5' end) of each selected β10 gene. When the antisense molecule then hybridizes to the corresponding β10 mRNA, translation of this mRNA is prevented or reduced. Anti-sense inhibitors provide information relating to the decrease or absence of a β10 polypeptide or α2/β10 heterodimer in a cell or organism.

Alternatively, gene therapy may be employed to create a dominant-negative inhibitor of one or more β10 polypeptides or α2/β10 heterodimers. In this situation, the DNA encoding a mutant polypeptide of each selected β10 polypeptide can be prepared and introduced into the cells of a patient using either viral or non-viral methods as described herein. Each such mutant is typically designed to compete with endogenous polypeptide or heterodimer in its biological role.

In addition, a β10 polypeptide or α2/β10 heterodimer of this invention, whether biologically active or not, may be used as an immunogen, that is, the polypeptide contains at least one epitope to which antibodies may be raised. Selective binding agents that bind to a β10 polypeptide or α2/β10 heterodimer (as described herein) may be used for in vivo and in vitro diagnostic purposes, including, but not limited to, use in labeled form to detect the presence of β10 polypeptide or α2/β10 heterodimer in a body fluid or cell sample. The antibodies may also be used to prevent, treat, or diagnose a number of diseases and disorders, including those recited herein. The antibodies may bind to a β10 polypeptide or α2/β10 heterodimer so as to diminish or block at least one activity characteristic of a β10 polypeptide or α2/β10 heterodimer, or may bind to a polypeptide to increase at least one activity characteristic of a β10 polypeptide or α2/β10 heterodimer (including by increasing the pharmacokinetics of a β10 polypeptide or α2/β10 heterodimer).

cDNA encoding human β10 polypeptide in *E. coli* was deposited with the American Type Culture Collection (ATCC), 10801 University Boulevard, Manassas, Va. 20110-2209, on Dec. 28, 1999, under accession number PTA-1210.

The following examples are intended for illustration purposes only, and should not be construed as limiting the scope of the invention in any way.

Example 1

DNA Encoding Human Beta-10

The amino acid sequence of CG-(chorionic gonadotropin)-β-subunit was Blasted against an, in house generated, Virtual Protein database derived from public human genomic sequences present in GenBank. A virtual protein containing a 45 amino acid region with significant homology to the carboxy half of CG-β was identified. The short (135 base pair) region of human genomic sequence that encoded the 45 amino acid stretch came from an over 160 kilobase pair GenBank human genomic DNA sequence (accession # AL049871). By analyzing an 8 kilobase pair stretch of genomic sequence just 5' of the 135 base pair sequence, a region having significant homology (and containing a frameshift) to the N-terminal half of CG-β was identified. The nucleotide sequence of this novel gene was compiled from the genomic sequences. The amino acid sequence of this compiled gene had significant homology to the four known human glycoprotein hormone β-subunit polypeptides and had an N-terminal predicted signal peptide, consistent with this novel human gene being a new β-like member of the glycoprotein hormone family. There was a 4.5-kb intron located between the two putative N-terminal half and C-terminal half coding exons. Intron spanning PCR (see *Tissue Expression, Beta-10* section below) of cDNAs from various tissues sources revealed that β10 was expressed in numerous tissues including pituitary.

The full coding region (ATG to TGA stop codon) and some of the 3'UTR (untranslated region) of β10 was cloned as one fragment by PCR using the following reaction mix and PCR conditions:

Template: ten microliters of Human Pituitary Marathon Ready cDNA (Clontech Laboratories, Inc., Palo Alto, Calif.; catalog no. 7424-1).

```
Forward primer:
5'-ATGAAGCTGGCATTCCTCTTCCTT-3'.      (SEQ ID NO: 4)

Reverse primer:
5'-GCATGTGCTGCTCACACAGGT-3'.         (SEQ ID NO: 5)
```

Final concentration of each primer: 1.0 micromolar.

Final concentration of dNTPs: 200 micromolar.

Five units of Pfu polymerase (Stratagene, La Jolla, Calif.).

Ten microliters of 10×Pfu reaction buffer (Stratagene, La Jolla, Calif.).

Ten microliters of GC melt (Clontech Laboratories, Inc., Palo Alto, Calif.; Advantage GC cDNA PCR kit; catalog no. K1907-1).

Final reaction volume: 100 microliters.

Cycling conditions: 94° C. for sixty seconds followed by 45 cycles of 94° C. (ten seconds), 60° C. (twenty seconds), 72° C. (ninety seconds), and then at the end of the 45th cycle an incubation at 72° C. for seven minutes, then an additional 10 cycles of 94° C. (ten seconds), 60° C. (twenty seconds), 72° C. (ninety seconds), and then at the end of the additional 10th cycle an incubation at 72° C. for seven minutes.

The PCR reaction was run on an agarose gel, and a single band was seen. This DNA band was cloned into pPCR-Script AMP (Stratagene). The sequence of the insert in one of the resulting clones is that of SEQ ID NO: 2 which contains the full coding region (ATG to TGA stop codon) and some of the 3'UTR (untranslated region) of β10.

The following is a list and description of β10 sequences from publicly available databases:

GenBank Accession # AL049871: 170 kilobase pairs of human genomic sequence. No exons, genes or homologies are identified in this record and the full coding region sequence of β10 is broken up by an intronic sequence.

GenBank Accession # AL118555: 126 kilobase pairs of human genomic sequence. No exons, genes or homologies are identified in this record and the full coding region sequence of β10 is broken up by an intronic sequence.

Example 2

Tissue Expression, Beta-10

Using a PCR fragment as a probe, it was not possible to obtain a hybridization signal on various Human Multiple Tissue Northern Blots (Clontech Inc., Palo Alto, Calif.). Intron spanning PCR was used to determine the expression pattern of beta-10 as described below.

For the Human Sure-RACE Panels (OriGene Technologies, Inc., Rockville, Md.; catalog no. HRAA-101) the cDNA samples represented brain, heart, kidney, spleen, liver, colon, lung, small intestine, muscle, stomach, testis, placenta, pituitary, thyroid gland, adrenal gland, pancreas, ovary, uterus, prostate, peripheral blood leucocytes, fetal brain, fetal liver, fat and mammary gland. Each cDNA sample was in a separate tube in the form of a dried down pellet of DNA. The reaction mixture was composed as follows:

```
Forward primer:
5'-CTGCAGGTGCCTTCGGATC-3';      (SEQ ID NO: 6)

Reverse primer:
5'-GCATGTGCTGCTCACACAGGT-3';    (SEQ ID NO: 5)
```

Amount of each primer: 0.5 picomoles;
Final concentration of dNTPs: 200 micromolar;
2.5 microliters of GC melt (Clontech Laboratories, Inc., Palo Alto, Calif.; Advantage GC cDNA PCR kit; catalog no. K1907-1);
2.5 units of Taq (Boehringer Mannheim, Indianapolis, Ind.; PCR Core Kit; catalog no. 1578 553);
2.5 microliters of 10x PCR-reaction buffer (Boehringer Mannheim, Indianapolis, Ind.; PCR Core Kit; catalog no. 1578 553);

For each cDNA sample the above reaction mixture was made up to a volume of 25 microliters, and 20 microliters of this mixture was added to the dried down cDNA pellet. The PCR conditions were as follows: 94° C. for sixty seconds, followed by 5 cycles of 94° C. (ten seconds) and 72° C. (forty seconds), followed by 5 cycles of 94° C. (ten seconds)and 70° C. (forty seconds), followed by 35 cycles of 94° C. (ten seconds)and 68° C. (forty seconds), and then followed by 68° C. for seven minutes.

PCR products were then analyzed by agarose gel electrophoresis. The correct size PCR product of 293 base pairs, indicating expression of $\beta 10$, was found in colon, small intestine, testis, pituitary and fetal liver.

For the Human Rapid-Scan Plate (OriGene Technologies, Inc., Rockville Md.; catalog no. HSCA-101) the cDNA samples represented brain, heart, kidney, spleen, liver, colon, lung, small intestine, muscle, stomach, testis, placenta, salivary gland, thyroid gland, adrenal gland, pancreas, ovary, uterus, prostate, skin, peripheral blood leucocytes, bone marrow, fetal brain and fetal liver. Each cDNA sample was in a separate tube in the form of a dried down pellet of DNA.

The reaction mixture that was utilized was as follows:

```
Forward primer:
5'-CTGCAGGTGCCTTCGGATC-3';      (SEQ ID NO: 6)

Reverse primer:
5'-GCATGTGCTGCTCACACAGGT-3';    (SEQ ID NO: 5)
```

Amount of each primer: 0.5 picomoles;
Final concentration of dNTPs: 200 micromolar;
2.5 microliters of GC melt (Clontech Laboratories, Inc., Palo Alto, Calif.; Advantage GC cDNA PCR kit; catalog no. K1907-1);
2.5 units of Taq (Boehringer Mannheim, Indianapolis, Ind.; PCR Core Kit; catalog no. 1578 553);
2.5 microliters of 10×PCR-reaction buffer (Boehringer Mannheim, Indianapolis, Ind.; PCR Core Kit; catalog no. 1578 553);

For each cDNA sample the above reaction mixture was made up to a volume of 25 microliters, and then 20 microliters of this mixture was added to the dried down cDNA pellet. The PCR conditions were as follows: 94° C. for sixty seconds followed by 5 cycles of 94° C. (ten seconds), 72° C. (forty seconds) and then followed by 5 cycles of 94° C. (ten seconds), 70° C. (forty seconds) and then followed by 35 cycles of 94° C. (ten seconds), 68° C. (forty seconds) and then followed by 68° C. for seven minutes.

PCR products were then analyzed by agarose gel electrophoresis. The correct size PCR product of 293 base pairs, indicating expression of $\beta 10$, was found in brain, spleen, liver, colon, stomach, placenta, thyroid gland, adrenal gland, pancreas, skin and peripheral blood leucocytes.

Combining the expression results from the Human Sure-RACE Panels and the Human Rapid-Scan Plate indicated that $\beta 10$ is expressed in brain, liver, fetal liver, stomach, pituitary, colon, small intestine, thyroid gland, adrenal gland, pancreas, skin, peripheral blood leucocytes, spleen, testis and placenta.

Example 3

Tissue Expression, $\alpha 2$

Northern analysis was carried out to determine the expression pattern of alpha-2. The probe for the Northerns was a 390-base pair PCR product (corresponding to nucleotides 56-445 of SEQ ID NO: 1 from WO99/41377). This PCR product was generated via a 466-base pair PCR intermediate as follows:

PCR was first used to clone a 466-base pair fragment of alpha-2 from human testis cDNA using the following reaction mixture and PCR conditions:

Template: ten microliters of Human Testis Marathon Ready cDNA (Clontech Laboratories, Inc., Palo Alto, Calif.; catalog no. 7414-1);

```
Forward primer:
5'-GAGACATCTCCCCACTGTGTTT-3';   (SEQ ID NO: 7)

Reverse primer:
5'-GTTTCCCCCAACAGAATGTCAA-3';   (SEQ ID NO: 8)
```

Final concentration of each primer: 1.0 micromolar;
Final concentration of dNTPs: 200 micromolar;
Five units of Pfu polymerase;
Final reaction volume: 100 microliters;
Cycling conditions: 94° C. for sixty seconds followed by 35 cycles of 94° C. (ten seconds), 60° C. (thirty seconds), 72° C. (sixty seconds), and then at the end of the 35th cycle an incubation at 72° C. for five minutes.

The PCR reaction was run on an agarose gel, and four distinct bands were seen. The multiple bands arose from PCR amplification of contaminating human genomic DNA present in the Human Testis Marathon Ready cDNA. The 466-base pair PCR product was isolated from the agarose gel and cloned. A plasmid clone containing the 466-base pair sequence was used as a template for generating the 390-base pair PCR fragment using the following reaction mix and PCR conditions:

Template: ten picograms of the plasmid clone containing the above mentioned 466-base pair sequence;

```
Forward primer:
5'-ATGCCTATGGCGTCCCCTCAAAC-3';         (SEQ ID NO: 9)

Reverse primer:
5'-CTAGTAGCGAGAGAGGCGACACATGTCA-3';    (SEQ ID NO: 10)
```

Final concentration of each primer: 1.0 micromolar.
Final concentration of dNTPs: 200 micromolar;
Ten units of Taq polymerase;
Final reaction volume: 100 microliters;
Cycling conditions: 94° C. for sixty seconds, followed by 35 cycles of 94° C. (ten seconds), 68° C. (sixty seconds), and then at the end of the 35th cycle an incubation at 68° C. for six minutes.

The 390-base pair PCR product was then purified by agarose gel electrophoresis. This PCR fragment was labeled with $^{32}P$ and hybridized to various Clontech Human Multiple Tissue Northern Blots (tissues/cells represented were: pancreas, adrenal medulla, thyroid, adrenal cortex, testis, thymus, small intestine, stomach, spleen, prostate, ovary, colon, peripheral blood leucocytes, brain, heart, skeletal muscle, kidney, liver, placenta and lung) and to a Northern blot made with pituitary mRNA using high stringency conditions as follows:

Hybridization was for one hour at 68° C. using Clontech "ExpressHyb Hybridization Solution". The blots were washed in 2×SSC, 0.1% SDS at room temperature twice, for twenty minutes each time. The blots were then washed in 0.1×SSC, 0.1% SDS at 50° C. for ten minutes, and then exposed to film.

A strong signal representing a single band was obtained in the pancreas mRNA lane and the pituitary mRNA lane. A significantly weaker signal was seen in the placenta mRNA lane.

In situ hybridization was done to further determine sites of α2 gene expression. A panel of normal embryonic (E10.5 through E18.5) and adult mouse tissues and adult rhesus monkey tissues were fixed in 4% paraformaldehyde, embedded in paraffin, and sectioned at 5 micrometers. Prior to in situ hybridization, tissues were permeabilized with 0.2M HCL, followed by digestion with Proteinase K and acetylation with triethanolamine and acetic anhydride. Sections were hybridized overnight at 55° C. with a $^{33}p$-labeled antisense RNA probe complementary to either the mouse or human (for rhesus tissues) α2 sequence and with sense (control) probes. The antisense and sense $^{33}p$-labeled RNA probes were obtained by in vitro transcription of plasmid DNAs containing either the mouse α2 cDNA (bacterial clone no. 1224990 from the public WashU-HHMI Mouse EST Project) or the human α2 cDNA (plasmid clone containing the above described PCR generated 390-base pair human α2 coding region sequence).

Following hybridization, sections were washed in buffer, treated with RNaseA to remove unhybridized probe, and then subjected to a high stringency wash in 0.1×SSC at 55° C. Slides were dipped in Kodak NTB2 emulsion, exposed at 4° C. for two-three weeks, developed, and then counterstained. Sections were examined with darkfield and standard illumination to allow simultaneous evaluation of tissue morphology and hybridization signal. The following tissues were then examined:

Mouse tissues: Brain (1 sagittal, 2 coronal sections); GI tract (esophagus, stomach, duodenum, jejunum, ileum, proximal & distal colon); pituitary; liver; lung; heart; spleen; thymus; lymph nodes; kidney; adrenal; bladder; pancreas; salivary gland; male and female reproductive organs (ovary, oviduct and uterus in the female; testis, epididymus, prostate, seminal vesicle and vas deferens in the male); BAT & WAT (subcutaneous, peri-renal); bone (femur); skin; breast; and skeletal muscle.

Rhesus tissues: adrenal gland; liver; gall bladder; intestine; pancreas; and salivary gland.

Both mouse and human antisense probes produced positive signal detectable above a very low level of background seen with the sense strand controls. In the embryonic mouse, no signal was observed in any major organs from E8.5 through E18.5. At E15.5 and E18.5, signal was present over scattered cells adjacent to some of the developing bones of the head and teeth. In the adult mouse, a moderate level of signal was present in the adrenal cortex. A lower level of signal was detectable in the anterior and intermediate lobes of the pituitary as well as in intestinal epithelium at the level of the crypts. In addition, grain density was slightly above background in developing sperm within the seminiferous tubules of the testis and in granulosa cells surrounding developing follicles in the ovary.

In rhesus tissues, moderate signal was noted in the adrenal cortex, gall bladder epithelium, and in the intestinal epithelium primarily at the level of the crypts.

Combining the expression results from the α2 Northerns and the α2 in situ analysis indicates that α2 is expressed in anterior pituitary, placenta, pancreas, adrenal cortex, intestinal crypts and gall bladder mucosa.

Example 4

Antibodies against α2

Rabbit polyclonal antibodies were generated against α2 by immunizing rabbits with peptide CSPRYSVLVASGYRHN (SEQ ID NO: 28) that had been conjugated to Keyhole Limpet Hemocyanin (cat#77605 Pierce Inc., Rockford, Ill.). The peptide was synthesized with a C-terminal amide so rather than the C-terminus being COOH the C-terminus was $CONH_2$. The RYSVLVASGYRHN portion of the peptide sequence is totally conserved between human and mouse α2. This region was chosen so that the antibodies would be able to bind to human α2 and mouse α2. The antibodies were affinity purified from rabbit serum over a column (SulfoLink Kit, cat# 44895, Pierce Inc., Rockford, Ill.) to which the peptide antigen (SEQ ID NO: 28) had been attached. Western blot analysis of conditioned media harvested from 293 cells that had been transfected with either a human α2-polyHis-tag mammalian expression vector or a human alpha-subunit-polyHis-tag mammalian expression vector demonstrated that these affinity purified polyclonal antibodies had high specificity for α2 polypeptide and did not cross react with alpha-subunit.

Example 5

DNA Encoding Mouse Beta-10

Various human Beta-10 cDNA probes were used to probe a mouse genomic 129SvJ BAC library arrayed on high density filters (catalog#FBAC-4431, Genome Systems, St. Louis, Mo.). The mouse BAC clone in plate#218-well#β22 was obtained (catalog# FBAC-4432, Genome Systems, St. Louis, Mo.). A 10-kb HindIII sub-fragment from this BAC clone hybridized strongly to a human Beta-10 cDNA probe. This 10-kb HindIII fragment was subcloned into pBluescriptII-KS(−) and fully sequenced. Computational analysis of this 10-kb mouse genomic sequence was used to identify two exons encoding the mouse ortholog of human Beta-10.

Primers were designed from this electronic sequence to clone the mouse Beta-10 cDNA as follows:

Template: twenty microliters of mouse testis Marathon Ready cDNA (Clontech Laboratories, Inc., Palo Alto, Calif.; catalog no. 7455-1).

Forward primer:
(SEQ ID NO: 14)
5'-ATTACTAGTTCCACCATGAAGTTGGTATACCTTGTCCTT-3';

Reverse primer:
(SEQ ID NO: 15)
5'-TTAATAATCGATCGTCAGATGGTCTCACACTCAGTG-3';

Final concentration of each primer: 1.0 micromolar.
PCR kit: Expand High Fidelity PCR System (catalog#1732641, Boehringer Mannheim Corporation, Indianapolis, Ind.).
Final reaction volume: 50 microliters;
Cycling conditions: 94° C. for sixty seconds, followed by 55 cycles of 94° C. (ten seconds), 65° C. (twenty seconds), 72° C. (forty seconds), and then at the end of the 55th cycle an incubation at 72° C. for seven minutes.

The 0.4-kb PCR product was then purified by agarose gel electrophoresis and cloned into pCR2.1 (Invitrogen Inc., Carlsbad, Calif.). A clone containing the full coding region cDNA of mouse Beta-10 (SEQ ID NO: 12) was identified by sequencing.

Example 6

Production and Analysis of Transgenic Mice Over Expressing α2 Alone, β10 Alone and Co-Expressing α2 and β10.

Transgenic mice over expressing α2 alone, β10 alone and co-expressing α2 and β10 from the human apolipoprotein E promoter were generated essentially as previously described (Simonet et al, 1997, Cell vol 89 p309-319). This human apoE promoter vector directs high level, liver specific, gene expression in transgenic mice, and has been previously used to generate transgenic mice having high levels of transgene encoded secreted protein in their circulation. For all phenotypic analyses described below the non-transgenic controls were mice that were produced during the same series of microinjections as the transgenic expressors in question.

Genomic (ie. containing α2 and β10 exons and introns) transgenes were used for generating transgenics to maximize expression. Additionally, in all cases a Kozak site (CCACC) was engineered just 5' of the start site ATG.

The human apoE promoter expression vector contains the HCR (liver specific enhancer element) followed by the apoE promoter and first intron (in apoE 5'UTR) and then by the SV40 polyA-signal/terminator. There are unique SpeI and SfiI (compatible with PvuI) sites for directional cloning of genes in between the apoE promoter-first intron and the SV40 polyA-signal/terminator regions of the vector.

The following procedure was used to generate the "mouse genomic α2 human apoE expression vector transgene":

Pools of the BAC Mouse ES (129SvJ) Genomic Screening Kit (catalog#BDTW-7460, Genome Systems, St. Louis, Mo.) were screened by PCR using mouse α2 specific primers. The mouse BAC clone in plate#44-well#H19 was obtained (catalog# FBAC-4432, Genome Systems, St. Louis, Mo.). A 12-kb XbaI sub-fragment from this BAC clone hybridized strongly to a mouse α2 cDNA probe. This 12-kb XbaI fragment was subcloned into pBluescriptII-KS(−)(Stratagene Inc, La Jolla, Calif.) and fully sequenced. Computational analysis of this 12-kb mouse genomic sequence was used to identify the three α2 coding exons.

Primers were designed to amplify the complete mouse genomic α2 coding sequence (start ATG to stop TAG; SEQ ID NO: 18) as follows:

Template: 5 nanograms of the 12-kb XbaI pBluescriptII-KS (−) clone DNA.

Forward primer:
(SEQ ID NO: 16)
5'-CCGCACTAGTTCCACCATGCCCATGGCACCACGAGT-3';

Reverse primer:
(SEQ ID NO: 17)
5'-GCGGCGTTCGATCGCTAGTAGCGGGAGAAACGGCACATATC-3';

Final concentration of each primer: 1.0 micromolar.
PCR kit: Pfu DNA Polymerase kit (Stratagene, La Jolla, Calif.).
Final reaction volume: 50 microliters;
Cycling conditions: 94° C. for sixty seconds, followed by 40 cycles of 94° C. (ten seconds), 60° C. (twenty seconds), 72° C. (180 seconds), and then at the end of the 40th cycle an incubation at 72° C. for four minutes.

The 0.8-kb PCR product was purified by agarose gel electrophoresis, cut with SpeI and PvuI and cloned into SpeI-SfiI cut human apoE expression vector. A clone containing the accurate full genomic coding region mouse α2 was identified by sequencing. DNA from this "mouse genomic α2 human apoE expression vector transgene" clone was digested with ClaI and ApaLI; the 4-kb band was purified by gel electrophoresis and used to generated transgenic mice as previously described (Simonet et al, 1997, Cell vol 89 p309-319). Transgenic mice were identified by PCR as follows:

Template: ear punch DNA.

Forward primer:
5'-GCCTCTAGAAAGAGCTGGGAC-3';      (SEQ ID NO: 19)

Reverse primer:
5'-CGCCGTGTTCCATTTATGAGC-3';      (SEQ ID NO: 20)

Final concentration of each primer: 1.0 micromolar.
PCR kit: Ready-to-Go PCR Beads (Amersham Pharmacia Biotech Inc., Piscataway, N.J.).
Final reaction volume: 25 microliters;
Cycling conditions: 30 cycles of 94° C. (sixty seconds), 62° C. (twenty seconds), 72° C. (30 seconds).

Upon electrophoresis of the PCR product the presence of the 0.37-kb band indicated that the particular mouse was transgenic.

Transgenics over expressing α2 were identified by Western blot of plasma (using the affinity purified anti-α2 polyclonal antibody described above in Example 4) obtained from the various PCR identified transgenics. Six α2 overexpressors (#s 7, 8, 26, 28, 156 and 186) as well as six non-transgenic control mice (#s 10, 11, 12, 18, 20, 21) were phenotypically analyzed. All mice were injected with 50 mg/kg BrdU one hour prior to harvest, radiographed, and sacrificed. Mice were sacrificed at 12 weeks of age. No significant findings were noted during necropsy.

For all mice, body and selected organ weights were taken, blood was drawn for hematology and serum chemistries, and organs were harvested for histologic analysis and BrdU labeling.

H&E stained sections of liver, gall bladder, spleen, lung, brain, pituitary, heart, kidney, adrenal, stomach, small intestine, pancreas, cecum, colon, mesenteric lymph node, skin, mammary gland, trachea, esophagus, thyroid, parathyroid, salivary gland, urinary bladder, ovary or testis, uterus or prostate and seminal vesicle, bone, and bone marrow were examined.

There were no biologically meaningful differences in the mean or individual animal organ weights, hematology values, clinical chemistry values or histologic findings between the α2 overexpressor transgenic mice and the non-transgenic control mice. In other words the α2 overexpressor transgenic mice did not have a phenotype.

The following procedure was used to generate the "mouse genomic β10 human apoE expression vector transgene".

Primers were designed to amplify the complete mouse genomic β10 coding sequence (start ATG to stop TGA; SEQ ID NO: 23) as follows:

Template: 10 nanograms of the mouse genomic β10 10-kb HindIII pBluescriptII-KS(−) clone DNA described in example 5.

```
Forward primer:
                                       (SEQ ID NO: 21)
5'-ATTACTAGTTCCACCATGAAGTTGGTATACCTTGTCCTT-3';

Reverse primer:
                                       (SEQ ID NO: 22)
5'-TTAATAATCGATCGTCAGATGGTCTCACACTCAGTG-3';
```

Final concentration of each primer: 1.0 micromolar.
PCR kit: PfuTurbo DNA Polymerase kit (Stratagene, La Jolla, Calif.).
Final reaction volume: 50 microliters;
Cycling conditions: 92° C. for sixty seconds, followed by 15 cycles of 92° C. (ten seconds), 65° C. (twenty seconds), 68° C. (four minutes).

The 3-kb PCR product was purified by agarose gel electrophoresis, cut with SpeI and PvuI and cloned into SpeI-SfiI cut human apoE expression vector. A "mouse genomic β10 human apoE expression vector transgene" clone containing the accurate full genomic coding region mouse β10 was identified by sequencing.

The following procedure was then used to generate the combined "mouse genomic β10 mouse genomic α2 human apoE expression vector transgene".

"Mouse genomic β10 human apoE expression vector transgene" clone DNA was cut with HindIII and SacII, and the ends were made blunt with DNA polymerase I Large (Klenow) Fragment (New England Biolabs, Beverly, MA). The 5.6-kb fragment was gel purified and cloned into HincII cut pBluescript II KS(−). A clone with the 5.6-kb "mouse genomic β10 human apoE expression cassette" in the orientation that has the SV40 polyA-signal/terminator region of the cassette next to HindIII site in the pBluescript II KS(−) polylinker was identified. DNA from this clone was cut with HindIII and SacII, and ligated to the 3.4-kb HindIII-SacII "mouse genomic α2 human apoE expression cassette" that had been isolated from the "mouse genomic α2 human apoE expression vector transgene" clone described above. The final 11.8-kb "mouse genomic β10 mouse genomic α2 human apoE expression vector transgene" construct consists of the "mouse genomic β10 human apoE expression cassette" and the "mouse genomic α2 human apoE expression cassette" cloned in tandem (ie. both in the same transcriptional orientation) into pBluescript II KS(−). In this construct β10 and α2 each have their own HCR/apoE promoter and SV40 polyA-signal/terminator for expression purposes.

DNA from this "mouse genomic β10 mouse genomic α2 human apoE expression vector transgene" clone was digested with BssHII; the 9-kb band was purified by gel electrophoresis and used to generated transgenic mice as previously described (Simonet et al, 1997, Cell vol 89 p309-319).

Mice transgenic for the "mouse genomic α2 human apoE expression cassette" were identified by PCR as follows:
Template: ear punch DNA.

```
Forward primer:
5'-CCAGTGTGATATGTGCCGTTTC-3';     (SEQ ID NO: 24)

Reverse primer:
5'-GAAGAGCGCAGAGCTCGGTA-3';       (SEQ ID NO: 25)
```

Final concentration of each primer: 1.0 micromolar.
PCR kit: Ready-to-Go PCR Beads (Amersham Pharmacia Biotech Inc., Piscataway, N.J.).
Final reaction volume: 25 microliters;
Cycling conditions: 94° C. for sixty seconds, followed by 35 cycles of 94° C. (ten seconds), 60° C. (twenty seconds), 72° C. (forty seconds), and then at the end of the 35th cycle an incubation at 72° C. for seven minutes.

The forward primer [5'-CCAGTGTGATATGTGC-CGTTTC-3' (SEQ ID NO: 24)] for this PCR is located in the $3^{rd}$ α2 coding exon (this exon contains the stop codon).

The reverse primer [5'-GAAGAGCGCAGAGCTCGGTA-3' (SEQ ID NO: 25)] for this PCR is located in the SV40 polyA-signal/terminator region.

Upon electrophoresis of the PCR product the presence of the 0.31-kb band indicated that the particular mouse was transgenic for the "mouse genomic α2 human apoE expression cassette". Those mouse numbers were: 25, 45, 53, 76, 94, 95, and 113.

Mice transgenic for the "mouse genomic β10 human apoE expression cassette" were identified by PCR as follows:
Template: ear punch DNA.

```
Forward primer:
5'-TGGAGTCGATCCTTTCTACACCTA-3';   (SEQ ID NO: 26)

Reverse primer:
5'-AGAGCGCAGAGCTCGGTAC-3';        (SEQ ID NO: 27)
```

Final concentration of each primer: 1.0 micromolar.
PCR kit: Ready-to-Go PCR Beads (Amersham Pharmacia Biotech Inc., Piscataway, N.J.).
Final reaction volume: 25 microliters;
Cycling conditions: 94° C. for sixty seconds, followed by 35 cycles of 94° C. (ten seconds), 60° C. (twenty seconds), 72° C. (forty seconds), and then at the end of the 35th cycle an incubation at 72° C. for seven minutes.

The forward primer [5'-TGGAGTCGATCCTTTCTA-CACCTA-3' (SEQ ID NO: 26)] for this PCR is located in the 2nd β10 coding exon (this exon contains the stop codon).

The reverse primer [5'-AGAGCGCAGAGCTCGGTAC-3' (SEQ ID NO: 27)] for this PCR is located in the SV40 polyA-signal/terminator region.

Upon electrophoresis of the PCR product the presence of the 0.37-kb band indicated that the particular mouse was transgenic for the "mouse genomic β10 human apoE expression cassette". Those mouse numbers were: 25, 31, 45, 53, 76, 94, 95, and 113. Of note, mouse #31 which was positive by PCR for the "mouse genomic β10 human apoE expression cassette" was negative by PCR for the "mouse genomic α2 human apoE expression cassette".

Mouse #76 and #113 died shortly after the PCR genotyping. The remaining six transgenics [#s 25 (female), 31 (male), 45 (female), 53 (male), 94 (male), and 95 (male)] as well as five non-transgenic control mice [#s 17 (male), 18 (female), 19 (female), 20 (male) and 21 (male)] were necropsied at 7 weeks of age for subsequent phenotypical analysis. All mice were injected with 50 mg/kg BrdU one hour prior to harvest, radiographed, and sacrificed. Upon necropsy abnormally large thyroid glands were found in some of the transgenic mice. As part of the necropsy, mice were weighed, blood was drawn for hematology and serum chemistries, and liver, spleen, kidney, heart, and thymus were weighed. Sections of liver, gall bladder, spleen, lung, brain, pituitary, heart, kidney, adrenal, thymus, stomach, small intestine, pancreas, cecum, colon, mesenteric lymph node, skin, mammary gland, trachea, esophagus, thyroid, parathyroid, salivary gland, urinary bladder, ovary or testis, uterus or prostate and seminal vesicle, bone, and bone marrow were harvested for histologic analysis.

Northern blot analysis was used to determine the levels of α2 and β10 mRNA in the livers of all of the transgenic and non-transgenic control mice as described below.

Total RNA was isolated from liver samples, quantitated and 10 micrograms of total RNA for each mouse was electrophoresed in a formaldehyde denaturation agarose gel and transferred to a Nylon membrane. This was done in duplicate to generate 2 Northern blots for probing. Ethidium Bromide staining of the agarose gels revealed virtually equal loading of RNA across all wells and between both gels. One Northern blot was probed with a random primed β32 labelled probe encompassing the full coding region of the α2 cDNA (from ATG to TAG) to assess α2 expression. The second Northern blot was probed with a random primed β32 labelled probe encompassing the full coding region of the β10 cDNA (from ATG to TGA) to assess β10 expression.

Hybridization was for one hour at 65° C. in "ExpressHyb Hybridization Solution" (Clontech, Palo Alto, Calif.). The blots were washed in 2× SSC, 0.1% SDS at room temperature twice, for twenty minutes each time. The blots were then washed in 0.1×SSC, 0.1% SDS at 50° C. for ten minutes, and then exposed to film.

The results of the Northern analysis are as follows:
For the non-transgenic control mice no signal was found for either α2 or β10.
For transgenic mouse #94 (male) no signal was found for either α2 or β10.
For transgenic mice #s 25 (female) and 45 (female) a strong signal was found for both α2 and β10.
For transgenic mouse #95 (male) a moderate signal was found for both α2 and β10.
For transgenic mouse #53 (male) a moderate signal was found for α2 and a weaker signal for β10.
For transgenic mouse #31 (male) a moderate signal was found for β10 but no signal was found for α2, indicating that mouse #31 overexpressed only β10 and not α2. The level of β10 expression in mouse #31 was significantly greater than that found in mouse #53. The expression results for transgenic mouse #31 are consistent with the PCR genotyping described above which for #31 was positive for the "mouse genomic β10 human apoE expression cassette" but negative for the "mouse genomic α2 human apoE expression cassette". The data for mouse #31 indicates that the "mouse genomic α2 human apoE expression cassette" region of the "mouse genomic β10 mouse genomic α2 human apoE expression vector transgene" DNA was truncated at some point during the microinjection process resulting in a mouse which overexpresses β10 but not α2. Shearing/truncation of transgene DNA during the process of creating transgenic mice has been reported previously in the transgenic literature.

H&E and BrdU stained sections of liver, gall bladder, spleen, lung, brain, pituitary, heart, kidney, adrenal, thymus, stomach, small intestine, pancreas, cecum, colon, mesenteric lymph node, skin, mammary gland, trachea, esophagus, thyroid, parathyroid, salivary gland, urinary bladder, ovary or testis, uterus or prostate and seminal vesicle, bone, and bone marrow from the 4 α2/β10 overexpressors (#s 25, 45, 53 and 95), the 5 non-transgenic control mice (#s 17, 18, 19, 20 and 21), and transgenic mouse #31, which only overexpressed β10 but not α2, were examined.

Immunohistochemical staining for BrdU was done on 4 μm thick paraffin embedded sections using an automated DPC Mark 5 Histochemical Staining System (Diagnostic Products Corp, Randolph, N.J.). Deparaffinized tissue sections were digested with 0.1 protease and then treated with 2N hydrochloric acid. Sections were blocked with CAS BLOCK (Zymed Laboratories, San Francisco, Calif.), incubated with a rat anti-BrdU monoclonal antibody (Accurate Chemical and Scientific, Westbury, N.Y.). The primary antibody was detected with a biotinylated rabbit anti-rat immunoglobulin polyclonal antibody (Dako, Carpinteria, Calif.). Sections were then quenched with 3% hydrogen peroxide, and reacted with an avidin-biotin complex tertiary (Vector Laboratories). The staining reaction was visualized with diaminobenzidine (DAB, Dako Carpinteria, Calif.) and sections were counterstained with hematoxylin.

All four α2/β10 overexpressors exhibited hepatomegaly (6.75±0.68% BW vs. 4.98±0.29% BW in non-transgenic control mice, p=0.0011) and renal hypertrophy (2.23±0.21% BW vs. 1.75±0.12% BW in non-transgenic control mice, p=0.0033). α2/β10 overexpressor mice also had a slightly lower mean body weight than their non-transgenic control counterparts; this difference was not statistically significant. α2/β10 overexpressor mice #s 45 and 53 also exhibited moderate splenomegaly. Transgenic mouse #31, which only overexpressed β10 and not α2, had normal liver, kidney and spleen weights.

All four α2/β10 overexpressor mice had elevated serum T4 levels (23.1±5.4 micrograms/dl vs. 5.0±0.7 micrograms/dl in non-transgenic control mice, p=0.0001) and transgenic mice #s 25 and 45 had a modest circulating lymphocytosis. Transgenic mouse #31, which only overexpressed β10 and not α2, had normal serum T4 levels and lymphocyte counts. Individual serum T4 values for each mouse are as follows: #17 (5.0 micrograms/dl), #18 (4.8 micrograms/dl), #19 (6.3 micrograms/dl), #20 (4.4 micrograms/dl), #21 (4.7 micrograms/dl), #25 (28.5 micrograms/dl), #45 (26.9 micrograms/dl), #53 (18.2 micrograms/dl), #95 (18.7 micrograms/dl), and #31 (3.2 micrograms/dl).

H&E and BrdU stained sections of liver, gall bladder, spleen, lung, brain, pituitary, heart, kidney, adrenal, thymus, stomach, small intestine, pancreas, cecum, colon, mesenteric lymph node, skin, mammary gland, trachea, esophagus, thyroid, parathyroid, salivary gland, urinary bladder, ovary or testis, uterus or prostate and seminal vesicle, bone, and bone marrow from the four α2/β10 overexpressor mice, the 5 non-transgenic control mice, and mouse #31, which only overexpressed β10 and not α2, were examined. Histologically, all four α2/β10 overexpressor mice exhibited bilaterally enlarged thyroid glands containing multiple follicular papillary adenomas. All four α2/β10 overexpressor mice also exhibited mild to moderate hepatocellular hyperplasia with an increase in hepatocellular BrdU labeling vs. the non-transgenic mice. Transgenic mouse #31 had none of these features.

In summary, the four α2/β10 overexpressor transgenic mice exhibited a phenotype characterized by bilateral thyroid enlargement with multiple follicular papillary adenomas and resulting hyperthyroidism, as indicated by elevated serum T4 levels. Other phenotypic changes were felt to be related to the systemic hyperthyroid state, and included moderate hepatomegaly, hepatocellular hyperplasia, and slightly decreased serum cholesterol levels, bilateral renal hypertrophy, and a mild to moderate leukocytosis with a predominance of lymphocytes.

Transgenic mice over expressing mouse α2 and not β10 (#s 7, 8, 26, 28, 156 and 186), described above, had no phenotype and transgenic mouse #31 over expressing β10 and not α2 had no phenotype. This indicates that the hyperthyroid phenotype found in all four α2/β10 overexpressor transgenic mice (#s 25, 45, 53 and 95) can be attributed to the α2/β10 heterodimeric hormone described in the present invention.

What is claimed:

1. An antibody that specifically binds a polypeptide comprising one or more of:
   (a) the amino acid sequence set forth in SEQ ID NO:3; and
   (b) the amino acid sequence set forth in SEQ ID NO:3, further comprising an amino-terminal methionine,
   wherein the antibody is a humanized antibody.

2. An antibody that specifically binds a polypeptide comprising one or more of:
   (a) the amino acid sequence set forth in SEQ ID NO:3; and
   (b) the amino acid sequence set forth in SEQ ID NO:3, further comprising an amino-terminal methionine,
   wherein the antibody is a human antibody.

3. An antibody that specifically binds a polypeptide comprising one or more of:
   (a) the amino acid sequence set forth in SEQ ID NO:3; and
   (b) the amino acid sequence set forth in SEQ ID NO:3, further comprising an amino-terminal methionine,
   wherein the antibody is a chimeric antibody.

4. An antibody that specifically binds a polypeptide comprising one or more of:
   (a) the amino acid sequence set forth in SEQ ID NO:3; and
   (b) the amino acid sequence set forth in SEQ ID NO:3, further comprising an amino-terminal methionine,
   wherein the antibody is a CDR-grafted antibody.

5. A variable region fragment of the antibody of claim 1, 2, 3 or 4.

6. The variable region fragment of claim 5 wherein the variable region fragment is a Fab or a Fab' fragment.

7. An antibody of claim 1, 2, 3 or 4 further comprising a detectable label.

8. A hybridoma that produces an antibody according to claim 1, 2, 3 or 4.

* * * * *

SEQUENCE LISTING

```
<160> NUMBER OF SEQ ID NOS: 32

<210> SEQ ID NO 1
<211> LENGTH: 130
<212> TYPE: PRT
<213> ORGANISM: Homo sapiens

<400> SEQUENCE: 1

Met Lys Leu Ala Phe Leu Phe Leu Gly Pro Met Ala Leu Leu Leu Leu
1               5                   10                  15

Ala Gly Tyr Gly Cys Val Leu Gly Ala Ser Ser Gly Asn Leu Arg Thr
            20                  25                  30

Phe Val Gly Cys Ala Val Arg Glu Phe Thr Phe Leu Ala Lys Lys Pro
        35                  40                  45

Gly Cys Arg Gly Leu Arg Ile Thr Thr Asp Ala Cys Trp Gly Arg Cys
    50                  55                  60

Glu Thr Trp Glu Lys Pro Ile Leu Glu Pro Pro Tyr Ile Glu Ala His
65                  70                  75                  80

His Arg Val Cys Thr Tyr Asn Glu Thr Lys Gln Val Thr Val Lys Leu
                85                  90                  95

Pro Asn Cys Ala Pro Gly Val Asp Pro Phe Tyr Thr Tyr Pro Val Ala
            100                 105                 110

Ile Arg Cys Asp Cys Gly Ala Cys Ser Thr Ala Thr Thr Glu Cys Glu
        115                 120                 125

Thr Ile
    130

<210> SEQ ID NO 2
<211> LENGTH: 390
<212> TYPE: DNA
<213> ORGANISM: Homo sapiens

<400> SEQUENCE: 2
atgaagctgg cattcctctt ccttggcccc atggccctcc tccttctggc tggctatggc      60
tgtgtcctcg gtgcctccag tgggaacctg cgcacctttg tgggctgtgc cgtgagggag     120
tttactttcc tggccaagaa gccaggctgc aggggccttc ggatcaccac ggatgcctgc     180
tggggtcgct gtgagacctg ggagaaaccc attctggaac cccctatat tgaagcccat      240 catcgagtct gtacctacaa cgagaccaaa caggtgactg tcaagctgcc caactgtgcc     300
ccgggagtcg accccttcta cacctatccc gtggccatcc gctgtgactg cggagcctgc     360
tccactgcca ccacggagtg tgagaccatc                                      390

<210> SEQ ID NO 3
<211> LENGTH: 106
<212> TYPE: PRT
<213> ORGANISM: Homo sapiens
```

<400> SEQUENCE: 3

```
Ala Ser Ser Gly Asn Leu Arg Thr Phe Val Gly Cys Ala Val Arg Glu
1               5                   10                  15

Phe Thr Phe Leu Ala Lys Lys Pro Gly Cys Arg Gly Leu Arg Ile Thr
            20                  25                  30

Thr Asp Ala Cys Trp Gly Arg Cys Glu Thr Trp Glu Lys Pro Ile Leu
        35                  40                  45

Glu Pro Pro Tyr Ile Glu Ala His His Arg Val Cys Thr Tyr Asn Glu
    50                  55                  60

Thr Lys Gln Val Thr Val Lys Leu Pro Asn Cys Ala Pro Gly Val Asp
65                  70                  75                  80

Pro Phe Tyr Thr Tyr Pro Val Ala Ile Arg Cys Asp Cys Gly Ala Cys
                85                  90                  95

Ser Thr Ala Thr Thr Glu Cys Glu Thr Ile
            100                 105
```

<210> SEQ ID NO 4
<211> LENGTH: 24
<212> TYPE: DNA
<213> ORGANISM: Homo sapiens

<400> SEQUENCE: 4
atgaagctgg cattcctctt cctt                                      24

<210> SEQ ID NO 5
<211> LENGTH: 21
<212> TYPE: DNA
<213> ORGANISM: Homo sapiens

<400> SEQUENCE: 5
gcatgtgctg ctcacacagg t                                         21

<210> SEQ ID NO 6
<211> LENGTH: 19
<212> TYPE: DNA
<213> ORGANISM: Homo sapiens

<400> SEQUENCE: 6
ctgcaggtgc cttcggatc                                            19

<210> SEQ ID NO 7
<211> LENGTH: 22
<212> TYPE: DNA
<213> ORGANISM: Homo sapiens

<400> SEQUENCE: 7
gagacatctc cccactgtgt tt                                        22

<210> SEQ ID NO 8
<211> LENGTH: 22
<212> TYPE: DNA
<213> ORGANISM: Homo sapiens

<400> SEQUENCE: 8
gtttccccca acagaatgtc aa                                        22

<210> SEQ ID NO 9
<211> LENGTH: 23
<212> TYPE: DNA
<213> ORGANISM: Homo sapiens

<400> SEQUENCE: 9

```
atgcctatgg cgtccctca aac                                              23

<210> SEQ ID NO 10
<211> LENGTH: 28
<212> TYPE: DNA
<213> ORGANISM: Homo sapiens

<400> SEQUENCE: 10
ctagtagcga gagaggcgac acatgtca                                        28

<210> SEQ ID NO 11
<211> LENGTH: 130
<212> TYPE: PRT
<213> ORGANISM: Mus musculus

<400> SEQUENCE: 11

Met Lys Leu Val Tyr Leu Val Leu Gly Ala Val Ala Leu Leu Leu Leu
1               5                   10                  15

Gly Gly Pro Asp Ser Val Leu Ser Ser Ser Gly Asn Leu His Thr
            20                  25                  30

Phe Val Gly Cys Ala Val Arg Glu Phe Thr Phe Met Ala Lys Lys Pro
        35                  40                  45

Gly Cys Arg Gly Leu Arg Ile Thr Thr Asp Ala Cys Trp Gly Arg Cys
    50                  55                  60

Glu Thr Trp Glu Lys Pro Ile Leu Glu Pro Pro Tyr Ile Glu Ala Tyr
65                  70                  75                  80

His Arg Val Cys Thr Tyr Asn Glu Thr Arg Gln Val Thr Val Lys Leu
                85                  90                  95

Pro Asn Cys Ala Pro Gly Val Asp Pro Phe Tyr Thr Tyr Pro Met Ala
            100                 105                 110

Val Arg Cys Asp Cys Gly Ala Cys Ser Thr Ala Thr Thr Glu Cys Glu
        115                 120                 125

Thr Ile
    130

<210> SEQ ID NO 12
<211> LENGTH: 393
<212> TYPE: DNA
<213> ORGANISM: Mus musculus

<400> SEQUENCE: 12
atgaagttgg tataccttgt ccttggtgca gtggccctcc ttctcctggg tggccctgac     60
tctgtcctca gcagctccag tgggaacctg cacttttg tgggctgtgc tgtgagggaa     120
ttcactttca tggccaagaa gccaggctgc aggggacttc ggatcaccac agatgcctgc    180
tggggccgct gcgagacctg ggagaaaccc atcctggagc ctccctacat tgaagcctat    240
catcgagtgt gtacatacaa tgagaccaga caggtgacag tgaagctgcc taactgtgcc    300
cctggagtcg atcctttcta cacctaccct atggctgtcc gatgtgactg tggggcgtgt    360
tccactgcca ccactgagtg tgagaccatc tga                                 393

<210> SEQ ID NO 13
<211> LENGTH: 106
<212> TYPE: PRT
<213> ORGANISM: Mus musculus

<400> SEQUENCE: 13

Ser Ser Ser Gly Asn Leu His Thr Phe Val Gly Cys Ala Val Arg Glu
1               5                   10                  15
```

```
Phe Thr Phe Met Ala Lys Lys Pro Gly Cys Arg Gly Leu Arg Ile Thr
            20                  25                  30

Thr Asp Ala Cys Trp Gly Arg Cys Glu Thr Trp Glu Lys Pro Ile Leu
        35                  40                  45

Glu Pro Pro Tyr Ile Glu Ala Tyr His Arg Val Cys Thr Tyr Asn Glu
    50                  55                  60

Thr Arg Gln Val Thr Val Lys Leu Pro Asn Cys Ala Pro Gly Val Asp
65                  70                  75                  80

Pro Phe Tyr Thr Tyr Pro Met Ala Val Arg Cys Asp Cys Gly Ala Cys
                85                  90                  95

Ser Thr Ala Thr Thr Glu Cys Glu Thr Ile
            100                 105
```

```
<210> SEQ ID NO 14
<211> LENGTH: 39
<212> TYPE: DNA
<213> ORGANISM: Artificial Sequence
<220> FEATURE:
<223> OTHER INFORMATION: Oligopeptide
<220> FEATURE:
<221> NAME/KEY: misc_feature
<223> OTHER INFORMATION: Oligonucleotide

<400> SEQUENCE: 14
attactagtt ccaccatgaa gttggtatac cttgtcctt                          39

<210> SEQ ID NO 15
<211> LENGTH: 36
<212> TYPE: DNA
<213> ORGANISM: Artificial Sequence
<220> FEATURE:
<223> OTHER INFORMATION: Oligonucleotide
<220> FEATURE:
<221> NAME/KEY: misc_feature
<223> OTHER INFORMATION: Oligonucleotide

<400> SEQUENCE: 15
ttaataatcg atcgtcagat ggtctcacac tcagtg                             36

<210> SEQ ID NO 16
<211> LENGTH: 36
<212> TYPE: DNA
<213> ORGANISM: Artificial Sequence
<220> FEATURE:
<223> OTHER INFORMATION: Oligonucleotide
<220> FEATURE:
<221> NAME/KEY: misc_feature
<223> OTHER INFORMATION: Oligonucleotide

<400> SEQUENCE: 16
ccgcactagt tccaccatgc ccatggcacc acgagt                             36

<210> SEQ ID NO 17
<211> LENGTH: 41
<212> TYPE: DNA
<213> ORGANISM: Artificial Sequence
<220> FEATURE:
<223> OTHER INFORMATION: Oligonucleotide
<220> FEATURE:
<221> NAME/KEY: misc_feature
<223> OTHER INFORMATION: Oligonucleotide

<400> SEQUENCE: 17
gcggcgttcg atcgctagta gcgggagaaa cggcacatat c                       41
```

<210> SEQ ID NO 18
<211> LENGTH: 815
<212> TYPE: DNA
<213> ORGANISM: Mus musculus

<400> SEQUENCE: 18

```
atgcccatgg caccacgagt cttgctcctt tgcctgctgg gcctggcagt cactgaaggg      60
catagcccag agacagccat cccaggctgc cacttgcacc gtgagtaact ctgcttgggg     120
agcggatgga cgggtaaccc ggccagcacg gccttcaccg gctgctccct tctctgcttc     180
cagccttcaa tgtgacggtg cgcagtgatc gcctcggcac ttgccagggc tcccacgtgg     240
cacaggcctg tgtaggacac tgtgagtcta gtgctttccc ttcccggtac tctgtgctgg     300
tggccagtgg ctatcggcac aacatcacct cttcctccca gtgctgcacc atcagcagcc     360
tcagaaaggt aaggggcctg agcctgatgg agcgtgaggg tggggaccca ggggcctgag     420
cctgatggag cgtgagggtg gggacccagg ggtccgaacc tgacctggtg tgagggtggg     480
gacccaggag cccgaacctg accaggtatg agggtgggga cccaggggcc cgaacctgac     540
cggggtgtaa gggtggggtc ccccaggggc ccgaacctga ccgggccata agggtgggga     600
cccccagggg cccgaacctg accaggtgtg agggtgagga cccaggggtt cgaacctgat     660 ggggggcgtga gggtggggtg gaatgggaac aaacttgggt cctcctccaa caggtgaggg     720
tgtggctgca gtgcgtgggg aaccagcgtg gggagcttga gatctttact gcaagggcct     780
gccagtgtga tatgtgccgt ttctcccgct actag                                 815
```

<210> SEQ ID NO 19
<211> LENGTH: 21
<212> TYPE: DNA
<213> ORGANISM: Homo sapiens

<400> SEQUENCE: 19

```
gcctctagaa agagctggga c                                                 21
```

<210> SEQ ID NO 20
<211> LENGTH: 21
<212> TYPE: DNA
<213> ORGANISM: Homo sapiens

<400> SEQUENCE: 20

```
cgccgtgttc catttatgag c                                                 21
```

<210> SEQ ID NO 21
<211> LENGTH: 39
<212> TYPE: DNA
<213> ORGANISM: Artificial Sequence
<220> FEATURE:
<223> OTHER INFORMATION: Oligonucleotide
<220> FEATURE:
<221> NAME/KEY: misc_feature
<223> OTHER INFORMATION: Oligonucleotide

<400> SEQUENCE: 21

```
attactagtt ccaccatgaa gttggtatac cttgtcctt                              39
```

<210> SEQ ID NO 22
<211> LENGTH: 36
<212> TYPE: DNA
<213> ORGANISM: Artificial Sequence
<220> FEATURE:
<223> OTHER INFORMATION: Oligonucleotide
<220> FEATURE:
<221> NAME/KEY: misc_feature
<223> OTHER INFORMATION: Oligonucleotide

<400> SEQUENCE: 22
ttaataatcg atcgtcagat ggtctcacac tcagtg                                    36

<210> SEQ ID NO 23
<211> LENGTH: 2985
<212> TYPE: DNA
<213> ORGANISM: Mus musculus

<400> SEQUENCE: 23

| | | | | | |
|---|---|---|---|---|---|
| atgaagttgg | tataccttgt | ccttggtgca | gtggccctcc | ttctcctggg | tggccctgac | 60 |
| tctgtcctca | gcagctccag | tgggaacctg | cacactttg | tgggctgtgc | tgtgagggaa | 120 |
| ttcactttca | tggccaagaa | gccaggctgc | aggggacttc | ggatcaccac | agatgcctgc | 180 |
| tggggccgct | gcgagacctg | ggaggtgagt | agtccaaggg | gcttgggtgg | cagtgtcctc | 240 |
| ggggacaggg | ccttgatttc | aagctcacag | tttcacgatg | gaggggaagc | tggcatacct | 300 |
| gccctgccct | ctgggctcta | aaaagctgat | cacacaatta | tttggcttct | tccatatggt | 360 |
| ctgaaaacca | tgatgatggt | tttttccaga | ggactgttga | ggttggtaat | gtaatttcca | 420 |
| tggttctgtt | tgggagccat | ccctaggagg | gtgggtgcta | ctatttaccc | attgtagaga | 480 |
| tcacaggaaa | ggagtcgaga | gggaatggct | tcgaagtcag | agagagtcag | tgcaaagttg | 540 |
| gaaatgaatt | cttggtccaa | acctgtgacc | acatctcctt | cctgtatttt | ctcagctgtg | 600 |
| aggaagtcag | gcagttaccc | agaagaaccc | ggaagctgca | tgctgagaga | ggcgtagtcc | 660 |
| caggctctgc | cacgactgtt | tccctttgt | cccagtccag | tgtgagatct | ggtctgtccc | 720 |
| tttataccca | gttctgtctg | gactttcatt | tttagagtgg | gtgcatacat | ctcaaagctg | 780 |
| gcttaactag | aaagtgttcg | tggtgtccag | ctgagctgac | tcttgctgaa | aatggtgacg | 840 |
| tctcagtgac | ctgagcttca | aagatggcag | atttagcaaa | attaaagcca | aagaacctc | 900 |
| cccacaccga | aatcaaccaa | ccaactcaaa | acaccattaa | cccccttcca | cctcagaccc | 960 |
| tccccacaat | ctgaagtgaa | gtgaaattaa | aaaaaaaaaa | gttaggggac | tcagataaat | 1020 |
| ttgaattcag | atcaataaca | caattttttt | ggcctaagcc | caccccaaat | attgcatgag | 1080 |
| acagatttat | aaaataaaaa | aattgaaata | caaagttaat | tgagtacgca | atttttctag | 1140 |
| aatcccagaa | tgctgagagt | cagaagacag | aatggagaga | gaaacggaac | ttctcctccc | 1200 |
| ggcccttgag | aaggacaggt | ctctgttttt | ataatattga | agctggatt | catcttgagc | 1260 |
| tggcttgcct | gtcatctata | ggtgtacaca | cacacacatg | tgtatgtgtg | tgtgcctatg | 1320 |
| cacatatgta | cttatgtatg | tatatatgta | tatctcttga | ttctatgtac | ctgcgtgcat | 1380 |
| tatctatata | cgtgtatgcc | tgtgcataca | tctaagcacg | tagctatgta | tagatgtatg | 1440 |
| tatcatctat | ctgatttccc | tacttaacat | tattattatt | ttttggattg | gaacaaaggg | 1500 |
| actgttccct | gaatgattat | tgttattgat | tcgttactac | atccttatac | ttgcgctcat | 1560 |
| aagagccatt | gactacttgt | attgagccct | gacctttcgc | cagggcttgt | gcactgcaca | 1620 |
| catcacctca | tctagctcca | tgacaatgct | agcaaaggtt | ttttttttt | tttattcctt | 1680 |
| atagaagagg | gaacaagggc | ttggaagagt | taagagcttc | ccctaggtct | ccagcagcag | 1740 |
| taaagcaggc | aggcatagtg | gggctgactg | cagactctgg | gtctctctct | actgatctct | 1800 |
| acgttctcta | acagaatcat | ctttgaagtc | aaggtttata | aaaggcaaag | ggaggaagtg | 1860 |
| aactaacccct | ccagtcatta | gagcagaata | ttcaggaagc | tccctggccc | tgctgtcttt | 1920 |
| tgtggattca | gttacaagta | gttccttgcag | aagtcctggg | taccaggctg | gctgggtact | 1980 |
| ggagaatagt | ggctgaccta | acggagctcg | gtctccacat | taggagcaat | gtcacacaaa | 2040 |

```
gatacaggag atggcatgtg gaaatggaga aacacagcaa accagccoct aaaccagaac    2100 cacacaggaa gggactaggg agcgccaggg cttggaggtg ggttgaagcg atttaaaata    2160
gcatcagaaa atgccgctct ggattgggtg agatttgaac agaatcctaa gagcttggtg    2220
ataggtgtgt gtgtgtgtgt gtgtgtgtgt gtgtgtgtgt gtgtgtgtgt gtggtgttct    2280
gggcagaggg aacagcagat acaaagaccc tcagtttggg ttctgaagca gcatagagac    2340
cactgtgact ggagctggag accgtgttgg caaggtcagg gccatagctg acatgtcaga    2400
agtaagagta cgggcagaaa atacagggac ttgagaagaa tcctagtgtc tgtgtttacc    2460
ctgagggaga tggaaaacta ccggggtttg agcagcggtg agccaggact gacttgtatt    2520
ttaaaaggct cattcgtgct gtaaacattt tgtaggggta atggtaggag aagggagacc    2580
agcatttact aaatatttac caagtgcatc ctgtgttctg tgggctttcg tggaagctcg    2640
ggacatggta atgagcaaag taacttcctg ctttcaggag tgtattcgta gtgggaggag    2700
tcagtacgta agtaaccagc cagtgatgac tggcaccaag aacaggaagc ggatgctgta    2760
ttctaacatt tttcctgttt tttacccttg ggatagaaac ccatcctgga gcctccctac    2820
attgaagcct atcatcgagt gtgtacatac aatgagacca gacaggtgac agtgaagctg    2880
cctaactgtg cccctggagt cgatcctttc tacacctacc ctatggctgt ccgatgtgac    2940 tgtgggcgt gttccactgc caccactgag tgtgagacca tctga                    2985

<210> SEQ ID NO 24
<211> LENGTH: 22
<212> TYPE: DNA
<213> ORGANISM: Mus musculus

<400> SEQUENCE: 24
ccagtgtgat atgtgccgtt tc                                                22

<210> SEQ ID NO 25
<211> LENGTH: 20
<212> TYPE: DNA
<213> ORGANISM: Simian virus 40

<400> SEQUENCE: 25
gaagagcgca gagctcggta                                                   20

<210> SEQ ID NO 26
<211> LENGTH: 24
<212> TYPE: DNA
<213> ORGANISM: Mus musculus

<400> SEQUENCE: 26
tggagtcgat cctttctaca ccta                                              24

<210> SEQ ID NO 27
<211> LENGTH: 19
<212> TYPE: DNA
<213> ORGANISM: Simian virus 40

<400> SEQUENCE: 27
agagcgcaga gctcggtac                                                    19

<210> SEQ ID NO 28
<211> LENGTH: 16
<212> TYPE: PRT
<213> ORGANISM: Artificial Sequence
<220> FEATURE:
<223> OTHER INFORMATION: Oligopeptide
```

<220> FEATURE:
<221> NAME/KEY: misc_feature
<223> OTHER INFORMATION: Oligopeptide

<400> SEQUENCE: 28

Cys Ser Pro Arg Tyr Ser Val Leu Val Ala Ser Gly Tyr Arg His Asn
1               5                   10                  15

<210> SEQ ID NO 29
<211> LENGTH: 108
<212> TYPE: PRT
<213> ORGANISM: Artificial Sequence
<220> FEATURE:
<223> OTHER INFORMATION: Oligopeptide

<400> SEQUENCE: 29

Trp Gly Gln Glu Ala Val Ile Pro Gly Cys His Leu His Pro Phe Asn
1               5                   10                  15

Val Thr Val Arg Ser Asp Arg Gln Gly Thr Cys Gln Gly Ser His Val
                20                  25                  30

Ala Gln Ala Cys Val Gly His Cys Glu Ser Ser Ala Phe Pro Ser Arg
            35                  40                  45

Tyr Ser Val Leu Val Ala Ser Gly Tyr Arg His Asn Ile Thr Ser Val
        50                  55                  60

Ser Gln Cys Cys Thr Ile Ser Gly Leu Lys Lys Val Lys Val Gln Leu
65                  70                  75                  80

Gln Cys Val Gly Ser Arg Arg Glu Glu Leu Glu Ile Phe Thr Ala Arg
                85                  90                  95

Ala Cys Gln Cys Asp Met Cys Arg Leu Ser Arg Tyr
            100                 105

<210> SEQ ID NO 30
<211> LENGTH: 324
<212> TYPE: DNA
<213> ORGANISM: Artificial Sequence
<220> FEATURE:
<223> OTHER INFORMATION: Oligopeptide

<400> SEQUENCE: 30
tggggccagg aggcagtcat cccaggctgc cacttgcacc ccttcaatgt gacagtgcga     60
agtgaccgcc aaggcacctg ccagggctcc cacgtggcac aggcctgtgt gggccactgt    120
gagtccagcg ccttcccttc tcggtactct gtgctggtgg ccagtggtta ccgacacaac    180
atcacctccg tctctcagtg ctgcaccatc agtggcctga agaaggtcaa agtacagctg    240
cagtgtgtgg ggagccggag ggaggagctc gagatcttca cggccagggc ctgccagtgt    300
gacatgtgtc gcctctctcg ctac                                           324

<210> SEQ ID NO 31
<211> LENGTH: 106
<212> TYPE: PRT
<213> ORGANISM: Artificial Sequence
<220> FEATURE:
<223> OTHER INFORMATION: Oligopeptide

<400> SEQUENCE: 31

Gln Glu Ala Val Ile Pro Gly Cys His Leu His Pro Phe Asn Val Thr
1               5                   10                  15

Val Arg Ser Asp Arg Gln Gly Thr Cys Gln Gly Ser His Val Ala Gln
                20                  25                  30

Ala Cys Val Gly His Cys Glu Ser Ser Ala Phe Pro Ser Arg Tyr Ser
            35                  40                  45

```
Val Leu Val Ala Ser Gly Tyr Arg His Asn Ile Thr Ser Val Ser Gln
     50              55                  60

Cys Cys Thr Ile Ser Gly Leu Lys Lys Val Lys Val Gln Leu Gln Cys
 65              70                  75                  80

Val Gly Ser Arg Arg Glu Glu Leu Glu Ile Phe Thr Ala Arg Ala Cys
             85                  90                  95

Gln Cys Asp Met Cys Arg Leu Ser Arg Tyr
            100             105

<210> SEQ ID NO 32
<211> LENGTH: 318
<212> TYPE: DNA
<213> ORGANISM: Artificial Sequence
<220> FEATURE:
<223> OTHER INFORMATION: Oligopeptide

<400> SEQUENCE: 32
caggaggcag tcatcccagg ctgccacttg cacccttca atgtgacagt gcgaagtgac        60
cgccaaggca cctgccaggg ctcccacgtg gcacaggcct gtgtgggcca ctgtgagtcc      120
agcgccttcc cttctcggta ctctgtgctg gtggccagtg gttaccgaca caacatcacc      180
tccgtctctc agtgctgcac catcagtggc ctgaagaagg tcaaagtaca gctgcagtgt      240
gtggggagcc ggagggagga gctcgagatc ttcacggcca gggcctgcca gtgtgacatg      300
tgtcgcctct ctcgctac                                                    318
```